US011926624B2

(12) United States Patent
Duvvuru

(10) Patent No.: US 11,926,624 B2
(45) Date of Patent: Mar. 12, 2024

(54) SYNTHESIS OF COELENTERAZINE SYNTHESIS INTERMEDIATE

(71) Applicant: INTERNATIONAL PAPER COMPANY, Memphis, TN (US)

(72) Inventor: Rajagopala Reddy Duvvuru, Hyderabad (IN)

(73) Assignee: INTERNATIONAL PAPER COMPANY, Memphis, TN (US)

(*) Notice: Subject to any disclaimer, the term of this patent is extended or adjusted under 35 U.S.C. 154(b) by 140 days.

(21) Appl. No.: 17/355,792

(22) Filed: Jun. 23, 2021

(65) Prior Publication Data

US 2021/0332044 A1 Oct. 28, 2021

Related U.S. Application Data

(60) Division of application No. 16/851,962, filed on Apr. 17, 2020, now Pat. No. 11,078,200, which is a continuation-in-part of application No. 16/457,788, filed on Jun. 28, 2019, now Pat. No. 11,008,326, which is a continuation of application No. 16/457,732, filed on Jun. 28, 2019.

(60) Provisional application No. 62/845,189, filed on May 8, 2019, provisional application No. 62/753,024, filed on Oct. 30, 2018, provisional application No. 62/692,502, filed on Jun. 29, 2018, provisional application No. 62/692,485, filed on Jun. 29, 2018.

(51) Int. Cl.
C07D 471/04 (2006.01)

(52) U.S. Cl.
CPC .................. C07D 471/04 (2013.01)

(58) Field of Classification Search
CPC .................................. C07D 471/04
See application file for complete search history.

(56) References Cited

U.S. PATENT DOCUMENTS

| | | | |
|---|---|---|---|
| 2,681,032 A | 6/1954 | Shaw |
| 3,675,654 A | 7/1972 | Baker |
| 3,702,610 A | 11/1972 | Sheppard |
| 3,731,685 A | 5/1973 | Eidus |
| 3,759,261 A | 9/1973 | Wang |
| 3,918,454 A | 11/1975 | Korodi |
| 3,952,746 A | 4/1976 | Summers |
| 4,022,211 A | 5/1977 | Timmons |
| 4,192,311 A | 3/1980 | Felfoldi |
| 4,231,370 A | 11/1980 | Mroz |
| 4,705,513 A | 11/1987 | Sheldon |
| 4,738,674 A | 4/1988 | Todd |
| 4,931,051 A | 6/1990 | Castello |
| 4,963,368 A | 10/1990 | Antrim |
| 5,447,689 A | 9/1995 | Gibboni |
| 5,947,943 A | 9/1999 | Lee |
| 5,952,311 A | 9/1999 | Kraus |
| 6,060,261 A | 5/2000 | Ryufuku |
| 6,066,774 A | 5/2000 | Roe |
| 6,113,886 A | 9/2000 | Bryan |
| 6,152,358 A | 11/2000 | Bryan |
| 6,416,960 B1 | 7/2002 | Bryan |
| 6,521,304 B1 | 2/2003 | Kajiyama |
| 7,595,319 B2 | 9/2009 | Berg |
| 8,546,147 B2 | 10/2013 | Giuliani |
| 8,642,281 B2 | 2/2014 | Inouye |
| 8,647,887 B2 | 2/2014 | Trowell et al. |
| 9,151,739 B2 | 10/2015 | Inouye |
| 10,273,463 B2 | 4/2019 | Petersen |
| 11,505,787 B2 | 11/2022 | Petersen et al. |
| 2004/0172000 A1 | 9/2004 | Roe |
| 2004/0209255 A1 | 10/2004 | Koster |
| 2005/0133387 A1 | 6/2005 | Cohen |
| 2006/0053505 A1 | 3/2006 | Bryan |
| 2006/0069362 A1 | 3/2006 | Odorzynski et al. |
| 2007/0026209 A1 | 2/2007 | MacDonald |
| 2010/0004613 A1 | 1/2010 | Cohen |
| 2011/0224638 A1 | 9/2011 | Cohen |
| 2012/0035070 A1 | 2/2012 | Inouye et al. |
| 2012/0157948 A1 | 6/2012 | Nhan et al. |
| 2012/0232272 A1 | 9/2012 | Inouye et al. |
| 2013/0088853 A1 | 4/2013 | Kingsley |
| 2013/0243741 A1 | 9/2013 | Bossmann |
| 2014/0045761 A1 | 2/2014 | Gibson |
| 2016/0108375 A1 | 4/2016 | Petersen |
| 2017/0274114 A1 | 9/2017 | Song |
| 2017/0335368 A1 | 11/2017 | Jiang et al. |
| 2019/0203187 A1 | 7/2019 | Petersen |
| 2020/0002344 A1 | 1/2020 | Duvvuru et al. |
| 2020/0085990 A1 | 3/2020 | Gao et al. |
| 2020/0239471 A1 | 7/2020 | Duvvuru |
| 2021/0070762 A1 | 3/2021 | Duvvuru et al. |

FOREIGN PATENT DOCUMENTS

| | | |
|---|---|---|
| CA | 2347436 A1 | 5/2000 |
| CA | 2420454 C | 12/2008 |
| CN | 101203199 A | 6/2008 |

(Continued)

OTHER PUBLICATIONS

Lu Yueting et al: "Efficient synthesis and antioxidant activity of coelenterazine analogues", Tetrahedron Letters, vol. 55, No. 45, 2014, pp. 6212-6215. Organic Preparations and Procedures International: The New Journal for Organic Synthesis; Synthesis of Coelenterazine Maciej Adamczyk a , Donald D. Johnson a , Phillip G. Mattingly a , You Pan a & Rajarathnam E. Reddy Department of Chemistry (9NM, Bldg AP20) Diagnostics Division , Abbott Lab. Semi-synthetic aequorins with improved sensitivity to Ca2+ ions Osamu Shimomura, et al., 1989.

Adamczyk, M., et al., "Synthesis of 3,7-dihydroimidazo[1,2a]pyrazine-3-ones and their chemiluminescent properties," Tetrahedron 59(41):8129-8142, Oct. 2003.

(Continued)

*Primary Examiner* — Paul V Ward

(74) *Attorney, Agent, or Firm* — Thomas W. Barnes, III

(57) ABSTRACT

Disclosed herein are synthesis methods for coelenterazine and intermediates. Also disclosed are articles including the coelenterazine and coelenterazine derivatives. Representative absorbent articles include disposable diapers and adult incontinence products.

6 Claims, No Drawings

(56) References Cited

FOREIGN PATENT DOCUMENTS

| | | |
|---|---|---|
| CN | 102432614 A | 5/2012 |
| CN | 102641187 A | 8/2012 |
| CN | 103209665 A | 7/2013 |
| CN | 103720539 A | 4/2014 |
| CN | 203724329 U | 7/2014 |
| CN | 105968114 A | 9/2016 |
| CN | 106999313 A | 8/2017 |
| EP | 0203715 A2 | 12/1986 |
| EP | 1393702 A1 | 3/2004 |
| JP | 2000500568 | 1/2000 |
| JP | 2001309968 A | 11/2001 |
| JP | 2001522644 A | 11/2001 |
| JP | 2004245818 | 9/2004 |
| JP | 2005304826 A | 11/2005 |
| JP | 2008104850 | 5/2008 |
| JP | 2011030792 A | 2/2011 |
| JP | 2016050296 A1 | 4/2016 |
| JP | 2017536865 | 12/2017 |
| WO | WO-199719353 A1 | 5/1997 |
| WO | WO-199923985 A | 5/1999 |
| WO | WO-2000065083 A1 | 11/2000 |
| WO | WO-200222183 A2 | 3/2002 |
| WO | WO-2010003038 A2 | 1/2010 |
| WO | WO-2010027556 A1 | 3/2010 |
| WO | WO-2010085844 A1 | 8/2010 |
| WO | WO-2016060850 A1 | 4/2016 |

OTHER PUBLICATIONS

Adamczyk, M., et al., "Synthesis of Coelenterazine," Organic Preparations and Procedures International 33(5):477-485, 2001.
Bhanja, C., and S. Chakroborty, "Synthon Disconnection Strategy for the Synthesis Design of 'Coelenterazine'—A Bioluminescent Marine Natural Product Used in Bioassays," Journal of Chemical and Pharmaceutical Research 4(5):2614-2625, 2012.
Communication dated Nov. 19, 2020, issued in European Application No. 15851372.1, filed Oct. 1, 2015, 6 pages.
Communication Pursuant to Article 94(3) EPC dated Aug. 27, 2019, issued in European Application No. 15851372.1, filed Oct. 1, 2015, 5 pages.
Extended European Search Report dated Jun. 4, 2018, issued in European Application No. 15851372.1, filed Oct. 1, 2015, 8 pages.
First Office Action dated Aug. 26, 2020, issued in Indian Patent Application No. 201717015226, filed Oct. 1, 2015, 5 pages.
First Office Action dated Aug. 22, 2018, issued in Chilean Application No. 2017000937, filed Apr. 13, 2017, with partial English translation from associate, 8 pages.
First Office Action dated Dec. 9, 2019, issued in Chinese Application No. 201580061908.6, filed Oct. 1, 2015, with partial English translation, 38 pages.
Huang, L., and J. Linlan, "The Synthesis and Evolution of Luciferin," Biotechnology Bulletin, No. 3, pp. 38-41, Jun. 2006.
International Preliminary Report on Patentability dated Apr. 27, 2017, issued in International Application No. PCT/US2015/053400, filed Oct. 1, 2015, 10 pages.
International Search Report and Written Opinion dated Mar. 25, 2020, issued in International Application No. PCT/US2019/040012, filed Jun. 28, 2019, 19 pages.
International Search Report and Written Opinion dated Sep. 18, 2019, issued in International Application No. PCT/US2019/040016, filed Jun. 28, 2019, 13 pages.
International Search Report dated Dec. 28, 2015, issued in International Application No. PCT/US2015/053400, filed Oct. 1, 2015, 2 pages.
Invitation to Pay Fees with Partial International Search Report and Written Opinion dated Nov. 6, 2019, issued in International Application No. PCT/US2019/040012, dated Jun. 28, 2019, 14 pages.

Keenan, M., et al., "Highly Efficient and Flexible Total Synthesis of Coelenterazine," Chemical Communications 323-324, 1997.
Li Lixia et. al, The Establishment of ATP Bioluminescent Detection Technique and the Feasibility Analysis of its Application, Food Science and Technology, vol. 37, No. 1, pp. 275-278, Jan. 20, 2012.
Mosrin Marc et al: "Regio- and Chemoselective Multiple Functionalization of Chloropyrazine Derivatives. Application to the Synthesis of Coelenterazine", Organic Letters, American Chemical Society, US, vol. 11, No. 15, Jun. 8, 2009 (Jun. 8, 2009), pp. 3406-3409.
Nakamura, H., et al., "Synthesis of 3,5-disubstituted 2-aminopyrazines by Palladium-Mediated Cross-Couplings and Its Use for Preparing Chemi- and/or Bio-Luminescent Compounds," ECHET 96 Article 055, <https://www.ch.ic.ac.uk/ectoc/echet96/papers/055/index.htm> [retrieved May 2, 2018], 3 pages.
Nishihara, R., et al., "Bioluminescent Coelenterazine Derivatives With Imidazopyrazinone C-6 Extended Substitution," ChemComm 51(2):391-394, Jan. 2015.
Nishihara, R., et al., "Electronic Supplementary Information for Bioluminescent Coelenterazine Derivatives with Imidazopyrazinone C-6 Extended Substitution," ChemComm 51(2):S1-S31, Jan. 2015.
Notice of Grounds of Rejection dated Aug. 27, 2019, issued in Japanese Application No. 2017-520490, filed Oct. 1, 2015, with English translation from associate, 6 pages.
Oba, Y., et al., "Biosynthesis of coelenterazine in the deep-sea copepod, Metridia pacifica," Biochemical and Biophysical Research Communications 390(3):684-688, Dec. 2009.
Second Office Action dated Aug. 20, 2020, issued in Chinese Patent Application No. 201580061908.6, filed Oct. 1, 2015, with partial English translation, 28 pages.
Second Office Action dated May 28, 2019, issued in Chilean Application No. 2017000937, filed Apr. 13, 2017, with partial English translation from associate, 5 pages.
Shimomura O et al: "Semi-Synthetic Aequorins With Improved Sensitivity to CA2+ Ions", Biochemical Journal, Published by Portland Press on Behalf of the Biochemical Society, vol. 261, No. 3, Aug. 1, 1989 (Aug. 1, 1989), pp. 913-920.
Teranishi, K., and O. Shimomura, "Solubilizing Coelenterazine in Water with Hydroxypropyl-β-cyclodextrin," Biosci Biotechnol Biochem. 61(7):1219-1220, Jul. 1997.
Victor M. Gonzalez, Jr., "Synthesis, Luminescence, and Applications of Coelenterazine and its Analogs," Feb. 2007, Abstract, 8 pages.
Gealageas, Ronan et al., Bioluminescent properties of obelin and aequorin with novel coelenterazine analogues, Analytical and Bioanalytical Chemistry, 2014, 406(11), pp. 2695-2707.
Huet, Francois et al., Ethyl Diethoxyacetate, e-EROS Encyclopedia of Reagents for Organic Synthesis, 2001.
Maciej Adamczyk et al; "Synthesis of Coelenterazine", Organic Preparations and Procedures International: The New Journal for Organic Synthesis, vol. 33, No. 5, Oct. 1, 2001, pp. 477-485.
Phakhodee, Wong et al., Suzuki-Miyaura coupling for general synthesis of dehydrocoelenterazine applicable for 6-position analogs directing toward bioluminescence studies, Tetrahedron, 2011, 67(6), pp. 1150-1157.
Vece, V., and G. Vuocolo, "Multicomponent Synthesis of Novel Coelenterazine Derivatives Substituted at the C-3 Position," Tetrahedron 71:8781-8785, 2015.
Takashi Hirano, et al., Chemi- and Bioluminescence of Coelenterazine Analogues Possessing an Adamantylmethyl Group, Tetrahedron, vol. 53, No. 38. pp. I12903-I12916, 1997.
Guadalupe Gonzalez-Trueba, et al., Synthesis of Coelenterazine, Analytical Biochemistry 240, pp. 308-310 (1996), Article No. 0365.
Huang Tao, Organic Chemistry Experiments, 2nd Ed., May 31, 1998, p. 167.
Qizheng, Yao, Pharmaceutical Synthesis Reaction, China Medical Science Press, Sep. 30, 2012, p. 475.
Shrestha, T.B., et al., "Strategies for Large-Scale Synthesis of Coelenterazine for In Vivo Applications," Synthesis 46:0646-0652, 2014.

SYNTHESIS OF COELENTERAZINE SYNTHESIS INTERMEDIATE

This application is a divisional application of U.S. application Ser. No. 16/851,962, filed on Apr. 17, 2020, which is a continuation-in-part application of U.S. application Ser. No. 16/457,788, filed on Jun. 28, 2019, which claims the benefit of U.S. Provisional Application No. 62/845,189, filed May 8, 2019, and U.S. Provisional Application No. 62/692,485, filed Jun. 29, 2018; and which also claims the benefit of U.S. application Ser. No. 16/457,732, filed Jun. 28, 2019, which claims the benefit the benefit of U.S. Provisional Application No. 62/753,024, filed Oct. 30, 2018, and U.S. Provisional Application No. 62/692,502, filed Jun. 29, 2018; each of which applications is expressly incorporated herein by reference in its entirety.

BACKGROUND

Personal care absorbent products, such as infant diapers, adult incontinent pads, and feminine care products, typically contain a fluid absorbent core. Many absorbent articles include the fluid absorbent core disposed between a top sheet and a back sheet. The top sheet can be formed from a fluid-permeable material adapted to promote fluid transfer into the absorbent core, such as upon a liquid insult, usually with minimal fluid retention by the top sheet. U.S. southern pine fluff pulp is commonly used in the absorbent core, generally in the form of a fibrous matrix, and sometimes in conjunction with a superabsorbent polymer (SAP) dispersed throughout the fibrous matrix. This fluff pulp is recognized worldwide as the preferred fiber for absorbent products, based on factors such as the fluff pulp's high fiber length, fiber coarseness, and its relative ease of processing from a wet-laid and dried pulp sheet to an air-laid web. The raw material for this type of cellulosic fluff pulp is Southern Pine (e.g., Loblolly Pine, *Pinus taeda* L.). The raw material is renewable, and the pulp is easily biodegradable. Compared to SAP, these fibers are inexpensive on a per mass basis but tend to be more expensive on per unit of liquid held basis. These fluff pulp fibers mostly absorb within the interstices between fibers. For this reason, a fibrous matrix readily releases acquired liquid on application of pressure. The tendency to release acquired liquid can result in significant skin wetness during use of an absorbent product that includes a core formed exclusively from cellulosic fibers. Such products also tend to leak the acquired liquid because liquid is not effectively retained in such a fibrous absorbent core.

SAPs are water-swellable, generally water-insoluble absorbent materials having a high absorbent capacity for fluids. They are used in absorbent articles like baby diapers or adult incontinent products to absorb and hold body fluids. SAP, upon absorption of fluids, swells and becomes a gel holding more than its weight of such fluids. The SAPs in common use are mostly derived from acrylic acid. Acrylic acid-based polymers also comprise a meaningful portion of the cost structure of diapers and incontinent pads. SAPs are designed to have high gel strength (as demonstrated by high absorbency under load or AUL). The high gel strength (upon swelling) of currently used SAP particles helps them to retain significant void space between particles, which is helpful for rapid fluid uptake. However, this high "void volume" simultaneously results in significant interstitial (between particles) liquid in the product in the saturated state. When there is interstitial liquid the "rewet" value or "wet feeling" of an absorbent product is compromised.

Some absorbent articles, such as diapers or adult incontinence pads, also include an acquisition and distribution layer (ADL) for the collection, and uniform and timely distribution of fluid from a fluid insult to the absorbent core. An ADL is usually placed between the top sheet and the absorbent core, and normally takes the form of composite fabric with most likely the top-one third of the fabric having low density (higher denier fiber) with relatively large voids and higher void volume for the effective acquisition of the presented fluid, even at relatively higher discharge rates. The middle one-third of the composite fabric of the ADL is usually made of higher density (low denier) fibers with smaller voids, while the lower one-third of the fabric is made of even higher density (lower and smaller denier) fibers and yet with finer voids. The higher density portions of the composite have more and finer capillaries and hence develop greater capillary pressure, thus moving greater volumes of fluid to the outer regions of the structure thus enabling the proper channelization and distribution of the fluid in an evenly fashion to allow the absorbent core to take up all of the liquid insult in a time bound manner to allow SAP within the absorbent core to hold and to gel the insult neither too slow nor too fast. The ADL provides for more rapid liquid acquisition (minimizing flooding in the target zone), and ensures more rapid transport and thorough distribution of the fluid into the absorbent core.

As noted above, the absorbent core is adapted to retain fluid, and as such may consist of one or more layers, such as layers to acquire, distribute, and/or store fluid. In many cases, a matrix of cellulose fibers, such as in the form of an air-laid pad and/or non-woven web, is used in (or as) the absorbent core of absorbent articles. In some cases, the different layers may consist of one or more different types of cellulose fibers, such as cross-linked cellulose fibers. The absorbent core may also include one or more fluid retention agents, such as one or more SAPs, distributed throughout the fiber matrix, usually as particles. Advances in SAP technology have allowed the design of absorbent core configurations in which fluff pulp contributes less to the absorbent capability of the core and more to providing a matrix structure in which the SAP is stably held. Fluff pulp fibers also provide fluid distribution functionality, to direct fluid to the SAP. However, it has been found that these structural and fluid distribution functions may be provided, in some configurations, by synthetic fibers, leading to the development of absorbent cores containing both fluff pulp fibers and synthetic fibers, and even "fluff-less" absorbent cores containing no fluff pulp fibers. These configurations may offer the advantage of being less physically bulky, without sacrificing absorbency.

The back sheet is typically formed from a fluid-impermeable material to form a barrier to prevent retained fluid from escaping.

Whatever the structure, when the absorbent article is wet from one or more liquid insults, the chances for the fluid coming in contact with the skin increases profoundly, and if left unchanged for a long time can result in diaper rash for infants or dermatitis problem in adults, thereby posing a skin wellness hazard. However, in general, the only way to know whether the diaper or the incontinent pad is dry or wet is to physically inspect it. During day time this may not pose a significant problem because a caregiver can check the diapers or adult incontinent products as many times as desired. However, inspections during night time can be a discomfort to the baby as well as to the adult, disturbing their sleep. Moreover, frequent night time inspections, such as several times in a single night, can disrupt the wearer's sleeping pattern, which poses health hazard to baby as well as the adult patient.

In addition, it is typical that an article of clothing, such as pants, pajamas, and/or undergarments, is worn over the diaper or absorbent article. Accordingly, even absorbent articles that incorporate different types of wetness and/or moisture indicators pose difficulties in timely discovery of an insult.

As a result, there it typically a time lapse between the insult and its discovery. If this time period is prolonged, then there exists the possibility of developing diaper rash, skin irritation, and/or skin flaking. These conditions can be very painful for those affected. This is particularly true for babies and those adults in care-giving facilities, and particularly true for night time insults, which can lead to longer periods prior to changing the absorbent article.

Previous moisture indicators incorporated into absorbent articles use color change as a visual indication of wetness detection. Inks that appear, or disappear, based on contact with liquid are popular mechanisms for wetness detection. Fluorescence has also been used for wetness detection, such as by incorporating a compound that fluoresces in the presence of a liquid. The mechanisms for such indicators generally fall into three broad categories: (1) imprinting a moisture indicating pattern on one of the piles of the absorbent article; (2) discrete moisture-indicating strips or layers that are incorporated between the layers of the absorbent article; and (3) a discrete (i.e., not part of the absorbent article's construction) indicating strip that is fastened to the interior of the absorbent article immediately prior to use.

Whatever the mechanism, these visual indicators are deficient in low-light (e.g., night time) situations. Appearing or disappearing inks must be directly visually detected, such that the caregiver can see the absorbent product. In low-light situations, this may require both a light source (e.g., overhead light or flashlight), as well as the removal of covering garments (e.g., pajamas or undergarments). Fluorescent indicators suffer similar issues, in that they require an external light source to excite the fluorescent compound. Such excitation is typically provided by exposing the indicator to UV light (which presents health concerns to the wearer and caregiver) and must be in direct optical communication with the fluorescent compound, which then requires removal of covering garments, blankets, etc. Therefore, the use of visual indicators previously used to detect wetness in absorbent garments suffers many disadvantages in low-light situations, which greatly reduces the usefulness of their indication mechanisms.

There is a need for chemiluminescent materials that can generate light upon exposure to moisture, where the chemiluminescent materials are readily synthesized in large yields and good purity. The present disclosure seeks to fulfill these needs and provides further advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a method of making coelenterazine, including: coupling 4-(5-amino-6-benzylpyrazin-2-yl)phenol (coelenteramine) with 3-(4-(benzyloxy)phenyl)-2-oxopropanal to provide 8-benzyl-2-(4-(benzyloxy)benzyl)-6-(4-hydroxyphenyl)imidazo[1,2-α]pyrazin-3(7H)-one; and deprotecting the 8-benzyl-2-(4-(benzyloxy)benzyl)-6-(4-hydroxyphenyl)imidazo[1,2-α]pyrazin-3(7H)-one to provide 8-benzyl-2-(4-hydroxybenzyl)-6-(4-hydroxyphenyl)imidazo[1,2-α]pyrazin-3(7H)-one (coelenterazine).

In another aspect, the present disclosure features a method of making 3-(4-(benzyloxy)phenyl)-2-oxopropanal, including providing 1-(benzyloxy)-4-(chloromethyl)benzene, and reacting the 1-(benzyloxy)-4-(chloromethyl)benzene in two steps to provide 3-(4-(benzyloxy)phenyl)-2-oxopropanal.

In another aspect, the present disclosure features a method of making coelenterazine, including:
   (a) reacting 3-benzylpyrazin-2-amine (25) with N-bromosuccinimide to provide 3-benzyl-5-bromopyrazin-2-amine (2);
   (b) reacting the 3-benzyl-5-bromopyrazin-2-amine (2) in two sequential steps to provide 4-(5-amino-6-benzylpyrazin-2-yl)phenol (7) (coelenteramine); and
   (c) coupling the 4-(5-amino-6-benzylpyrazin-2-yl)phenol (7) with silyl-protected 1,1-diethoxy-3-(4-hydroxyphenyl)propan-2-one to provide coelenterazine, or a salt thereof.

In yet another aspect, the present disclosure features a method of making coelenterazine, including:
   coupling 4-(5-amino-6-benzylpyrazin-2-yl)phenol (7) with 3-(4-((tert-butyldimethylsilyl)oxy)phenyl)-1,1-diethoxypropan-2-one (23) to provide coelenterazine (16), or a salt thereof;
   wherein the 3-(4-((tert-butyldimethylsilyl)oxy)phenyl)-1,1-diethoxypropan-2-one (23) is synthesized by
      i. reacting 4-hydroxybenzaldehyde (8) with tert-butyldimethylsilyl chloride to provide 4-((tert-butyldimethylsilyl)oxy)benzaldehyde (20a);
      ii. reacting the 4-((tert-butyldimethylsilyl)oxy)benzaldehyde with sodium borohydride to provide (4-((tert-butyldimethylsilyl)oxy)phenyl)methanol (20b);
      iii. reacting the (4-((tert-butyldimethylsilypoxy)phenyl)methanol with methanesulfonyl chloride to provide tert-butyl(4-(chloromethyl)phenoxy)dimethylsilane (21);
      iv. reacting the tert-butyl(4-(chloromethyl)phenoxy)dimethylsilane with magnesium to provide (4-((tert-butyldimethylsilyl)oxy)benzyl)magnesium chloride (22); and
      v. reacting the (4-((tert-butyldimethylsilyl)oxy)benzyl)magnesium chloride with ethyl 2,2-diethoxyacetate to provide the 3-(4-((tert-butyldimethylsilyl)oxy)phenyl)-1,1-diethoxypropan-2-one (23).

In yet another aspect, the present disclosure features a method of making coelenterazine, including:
   coupling 4-(5-amino-6-benzylpyrazin-2-yl)phenol (7) with 1,1-diethoxy-3-(4-hydroxyphenyl)propan-2-one (14) to provide coelenterazine, or a salt thereof.

In yet a further aspect, the present disclosure features a method of making coelenterazine, including:
   (a) reacting 3,5-dibromopyrazin-2-amine and (bromomethyl)benzene in the presence of zinc, iodine, and a first palladium catalyst to provide 3-benzyl-5-bromopyrazin-2-amine (2);
   (b) reacting 3-benzyl-5-bromopyrazin-2-amine (2) in a first step to provide a hydrochloride salt of 3-benzyl-5-(4-methoxyphenyl)pyrazin-2-amine (5), and reacting the hydrochloride salt of 3-benzyl-5-(4-methoxyphenyl)pyrazin-2-amine (5) in a second step to provide 4-(5-amino-6-benzylpyrazin-2-yl)phenol (7); and (c) coupling 4-(5-amino-6-benzylpyrazin-2-yl)phenol (7) with 1,1-diethoxy-3-(4-hydroxyphenyl)propan-2-one (14) to provide coelenterazine (16), or a salt thereof.

In yet another aspect, the present disclosure features a method of making coelenterazine, including:

coupling 4-(5-amino-6-benzylpyrazin-2-yl)phenol (7) with 1,1-diethoxy-3-(4-hydroxyphenyl)propan-2-one (14) for a duration of 16 hours to 28 hours, to provide coelenterazine, or a salt thereof;

wherein the coupling reaction is monitored by reverse phase HPLC and is quenched when 4-(5-amino-6-benzylpyrazin-2-yl)phenol (7) stops depleting, or when coelenterazine starts to decompose.

In yet another aspect, the present disclosure features a method of making coelenterazine, including:

reacting 4-(5-amino-6-benzylpyrazin-2-yl)phenol (7) with 1,1-diethoxy-3-(4-hydroxyphenyl)propan-2-one (14) for a duration of 16 hours to 28 hours to provide crude coelenterazine, or a salt thereof;

triturating crude coelenterazine with ethyl acetate; and isolating a coelenterazine, or salt thereof.

In yet another aspect, the present disclosure features a method of making coelenterazine, including (a) reacting pyrazin-2-amine (24) with benzyl chloride to provide 3-benzylpyrazin-2-amine (25) (e.g., under Grignard conditions, such as by first providing a solution of magnesium, iodine, and ethyl bromide in a solvent before reacting pyrazin-2-amine (24) with benzyl chloride to provide 3-benzylpyrazin-2-amine (25); (b) reacting 3-benzylpyrazin-2-amine (25) with N-bromosuccinimide to provide 3-benzyl-5-bromopyrazin-2-amine (2); (c) reacting the 3-benzyl-5-bromopyrazin-2-amine (2) in two sequential steps to provide 4-(5-amino-6-benzylpyrazin-2-yl)phenol (7) (coelenteramine); and (d)

coupling the 4-(5-amino-6-benzylpyrazin-2-yl)phenol (7) with silyl-protected 1,1-dimethoxy-3-(4-hydroxyphenyl)propan-2-one or silyl-protected 1,1-diethoxy-3-(4-hydroxyphenyl)propan-2-one to provide coelenterazine (16), or a salt thereof.

In another aspect, the present disclosure features a method of making an absorbent article, including incorporating the coelenterazine made according to the methods of the present disclosure into an absorbent article.

In yet another aspect, the present disclosure features an absorbent article, including the coelenterazine synthesized by the methods of the present disclosure.

DETAILED DESCRIPTION

Disclosed herein are synthesis methods for making coelenterazine, in high yield and with good purity. Also disclosed are articles including the coelenterazine and coelenterazine derivatives. Representative absorbent articles include disposable diapers and adult incontinence products.

Chemiluminescence results from a chemical reaction that produces light and therefore provides a lighted indication of moisture that can be seen in low light and/or in the absence of light, and through clothes. Furthermore, chemiluminescence requires no external excitation light, as is required for photoluminescent (e.g., fluorescence) indicators. Accordingly, by generating light upon contact with an aqueous system (e.g., urine), the disclosed embodiments greatly enhance the ability of absorbent articles to indicate the occurrence of an insult in darkened conditions (e.g., at night). Moreover, by generating light that can be seen through clothing, a caregiver may be able to ascertain the occurrence of an insult without having to move or disturb the infant or adult wearer of such an absorbent article, such as during sleep.

The articles provided herein may provide the distinct advantages of insult indication at night and through clothes, which may reduce or even eliminate the need for caregivers to disturb the sleep (e.g., by pulling down clothes and/or shining a light) of one wearing an absorbent article in order to test for an insult. Further, because light (e.g., visible light) is produced by the chemiluminescent systems disclosed herein, there is no need to expose the absorbent article and/or the wearer to UV light in order to determine whether an insult has occurred, allowing health concerns associated with UV radiation to be avoided. Examples of articles including chemiluminescent materials are described, for example, in U.S. application Ser. No. 14/516,255, the disclosure of which is herein incorporated in its entirety.

The articles of the present disclosure provide improved ease with which an insult can be detected, which allows the caregiver to check for an insult more frequently, due to the reduced interruption required. More frequent checks may allow an insult to be detected sooner and the absorbent article changed soon after the insult, thereby reducing the amount of time the insult contacts the wearer's skin, as well as reducing the possibility of fluid from multiple insults contacting the wearer's skin. The skin health and general comfort of the wearer are improved when the length of time that fluid is in contact with the skin is reduced. In some embodiments, the component amounts/ratios can be calibrated so that instead of seeing a peak and then a fade after each of a sequence of insults, once there is sufficient water present in the absorbent article, the luminescence can be maintained at a relatively steady intensity (e.g., the luminescence can vary less than about 30%, less than about 20%, less than about 10%, less than 30%, less than 20%, or less than 10%,) over a period of time (e.g., about 24 hours, about 12 hours, about 6 hours, about 3 hours, about 2 hours, about 1 hour, about 30 minutes, about 15 minutes, 24 hours, 12 hours, 6 hours, 3 hours, 2 hours, 1 hour, 30 minutes, or 15 minutes). As used herein, the word "about" as it relates to a quantity indicates a number within range of minor variation above or below the stated reference number. For example, "about" can refer to a number within a range of 10%, 9%, 8%, 7%, 6%, 5%, 4%, 3%, 2%, or 1% above or below the indicated reference number. In some embodiments, "about" refers to a number within a range of 5% above or below the indicated reference number. In some embodiments, "about" refers to a number within a range of 10% above or below the indicated reference number. In some embodiments, "about" refers to a number within a range of 1% above or below the indicated reference number.

Synthesis of Coelenterazine

In one aspect, the present disclosure features a method of making coelenterazine, including coupling coelenteramine, or a salt thereof, with a protected 1,1-diethoxy-3-(4-hydroxyphenyl)propan-2-one; or coupling coelenteramine, or a salt thereof, with 1,1-diethoxy-3-(4-hydroxyphenyl)propan-2-one (14), to provide coelenterazine, or a salt thereof.

In another aspect, the present disclosure features a method of making coelenterazine, including coupling coelenteramine, or a salt thereof, with a protected 1,1-dimethoxy-3-(4-hydroxyphenyl)propan-2-one (e.g., a silyl-protected 1,1-dimethoxy-3-(4-hydroxyphenyl)propan-2-one), to provide coelenterazine, or a salt thereof.

In another aspect, the present disclosure features a method of making coelenterazine, including coupling 4-(5-amino-6-benzylpyrazin-2-yl)phenol (coelenteramine) with 3-(4-

(benzyloxy)phenyl)-2-oxopropanal to provide 8-benzyl-2-(4-(benzyloxy)benzyl)-6-(4-hydroxyphenyl)imidazo[1,2-α]pyrazin-3(7H)-one; and deprotecting the 8-benzyl-2-(4-(benzyloxy)benzyl)-6-(4-hydroxyphenyl)imidazo[1,2-α]pyrazin-3(7H)-one to provide 8-benzyl-2-(4-hydroxybenzyl)-6-(4-hydroxyphenyl)imidazo[1,2-α]pyrazin-3(7H)-one (coelenterazine).

The coelenteramine can be made via different routes, as outlined below. The methods can provide coelenterazine in good yield and at good purity.

Coelenteramine Synthesis

In some embodiments, the coelenteramine is made by first (a1) reacting 3-benzylpyrazin-2-amine (25) with N-bromosuccinimide to provide 3-benzyl-5-bromopyrazin-2-amine (2), or a salt thereof or by (a2) reacting 3,5-dibromopyrazin-2-amine and (bromomethyl)benzene in the presence of zinc, iodine, and a palladium catalyst to provide the 3-benzyl-5-bromopyrazin-2-amine (2), or a salt thereof. In a step (b), the 3-benzyl-5-bromopyrazin-2-amine (2) is then reacted in two sequential steps to provide 4-(5-amino-6-benzylpyrazin-2-yl)phenol (7) (coelenteramine).

The reaction of (a1) 3-benzylpyrazin-2-amine (25) with N-bromosuccinimide can be carried out in an organic solvent, such as $CHCl_3$ (chloroform) at room temperature (e.g., about 22° C. to 23° C., 22° C. to 23° C., or 22° C.) at atmospheric pressure (i.e., about 1 atm, or 1 atm). Once the reaction is complete, the reaction mixture can be washed with water, and 3-benzyl-5-bromopyrazin-2-amine (2) can be isolated by removing the organic solvent under reduced pressure. In some embodiments, (a1) provides 3-benzyl-5-bromopyrazin-2-amine (2) in a yield of about 60% to about 85% (e.g., 60% to 85%) relative to 3-benzylpyrazin-2-amine (25) and in a purity of at least about 85% (e.g., a purity of about 85% to about 95%, a purity of about 85% to about 100%, a purity of 85% to 95%, or a purity of 85% to 100%). As used herein, it is understood that % yield refers to mole % yield. As used herein, the purity of a given compound (when accompanied by the % yield of the given compound) refers to the weight percent purity relative to the mass of the pure compound calculated based on mole % yield.

In some embodiments, in (a2), the palladium catalyst is bis(triphenylphosphine) palladium(II) dichloride. The palladium catalyst can be present in an amount of about 5 to about 10 mole percent (e.g., 5 to 10 mole percent) relative to 3,5-dibromopyrazin-2-amine. In some embodiments, (a2) includes about 1:2 to about 1:3 molar equivalent (e.g., 1:2 to 1:3 molar equivalent) of 3,5-dibromopyrazin-2-amine to (bromomethyl)benzene. (a2) can provide 3-benzyl-5-bromopyrazin-2-amine (2) in a yield of about 55% to about 75% (e.g., 55% to 75%) relative to the 3,5-dibromopyrazin-2-amine at a purity of about 80% to about 95% (80% to 95%). In some embodiments, (a2) includes reacting 3,5-dibromopyrazin-2-amine and (bromomethyl)benzene for a duration of about 18 hours to about 30 hours (e.g., 18 hours to 30 hours). The reaction of 3,5-dibromopyrazin-2-amine and the (bromomethyl)benzene can occur at a temperature of about 25 to about 40° C. (e.g., 25 to 40° C.) at a pressure of about 1 atm (e.g., 1 atm).

In some embodiments, step (b) includes a first step of reacting the 3-benzyl-5-bromopyrazin-2-amine (2) with 4-methoxyphenyl boronic acid (4) in the presence of a palladium catalyst to provide 3-benzyl-5-(4-methoxyphenyl)pyrazin-2-amine (5), or salt thereof. The palladium catalyst can be a palladium (0) catalyst, for example, tetrakis(triphenylphosphine)palladium(0). The palladium catalyst can be present in an amount of about 5 to about 10 percent by weight (e.g., 5 to 10 percent by weight) relative to the 3-benzyl-5-bromopyrazin-2-amine (2). The first step in (b) can include about 1:1 to about 1:1.3 molar equivalent of the 3-benzyl-5-bromopyrazin-2-amine (2) to 4-methoxyphenyl boronic acid (4). In some embodiments, the 3-benzyl-5-bromopyrazin-2-amine (2) and the 4-methoxyphenyl boronic acid (4) are reacted together for a duration of about 120 minutes to about 300 minutes (e.g., 120 minutes to 300 minutes). The 3-benzyl-5-bromopyrazin-2-amine (2) and the 4-methoxyphenyl boronic acid (4) can be reacted together at a temperature of about 60° C. to about 90° C. (e.g., 60° C. to 90° C.) and at atmospheric pressure (i.e., a pressure of about 1 atm, or 1 atm). The first step in (b) can provide the 3-benzyl-5-(4-methoxyphenyl)pyrazin-2-amine (5), or salt thereof, in a yield of about 60% to about 85% (e.g., 60% to 85%) relative to the 3-benzyl-5-bromopyrazin-2-amine (2) of the product at a purity of about 80 to about 95% (i.e., a yield of 60% to 85% of the 80%-95% pure product). As used here, yield at a given purity range refers to the yield of the product having the described purity range.

Alternatively, in some embodiments, (b) includes a first step of reacting the 3-benzyl-5-bromopyrazin-2-amine (2) with (4-methoxyphenyl)boronic acid in the presence of a palladium catalyst (e.g., a palladium (II) catalyst, such as bis(benzonitrile) palladium(II) dichloride) to provide 3-benzyl-5-(4-methoxyphenyl)pyrazin-2-amine (5) or a salt thereof. The palladium (II) catalyst can be present in an amount of about 5 to about 10 (e.g., 5 to 10) mole percent relative to the 3-benzyl-5-bromopyrazin-2-amine (2). The reaction mixture can further include 1,4-bis(diphenylphosphino)butane, for example, in an amount of about 5 to about 10 (e.g., 5 to 10) mole percent relative to the 3-benzyl-5-bromopyrazin-2-amine (2). In some embodiments, the reaction mixture further includes toluene, aqueous sodium carbonate, and ethanol. The 3-benzyl-5-bromopyrazin-2-amine (2) can be reacted with the (4-methoxyphenyl)boronic acid for a duration of about 200 minutes to about 350 minutes (e.g., 200 to 350 minutes), and/or at a temperature of about 80 to about 110° C. (e.g., 80 to 100° C.) and at a pressure of about 1 atm (e.g., 1 atm). When the palladium (II) catalyst is used, 3-benzyl-5-(4-methoxyphenyl)pyrazin-2-amine (5) can be provided in a yield of about 65% to about 85% (e.g., 65% to 85%) relative to the 3-benzyl-5-bromopyrazin-2-amine (2). The 3-benzyl-5-(4-methoxyphenyl)pyrazin-2-amine (5) can be isolated by diluting the reaction mixture with water and extracting with ethyl acetate. The ethyl acetate extract can be removed from the extract under reduced pressure to provide 3-benzyl-5-(4-methoxyphenyl)pyrazin-2-amine (5).

The 3-benzyl-5-(4-methoxyphenyl)pyrazin-2-amine (5), or salt thereof, regardless of whether obtained with a palladium (0) or palladium (II) catalyst, can be isolated by precipitation of the 3-benzyl-5-(4-methoxyphenyl)pyrazin-2-amine (5) as a hydrochloride salt. Precipitation is advantageous as it can eliminate column chromatography, which can be laborious, costly, and time-consuming; and/or can also increase yield relative to column chromatography. In some embodiments, isolating the 3-benzyl-5-(4-methoxyphenyl)pyrazin-2-amine (5) does not include chromatography (e.g., liquid chromatography), does not include recrystallization, or does not include chromatography and recrystallization. In some embodiments, the reaction mixture from the reaction of 3-benzyl-5-bromopyrazin-2-amine (2) with (4-methoxyphenyl)boronic acid is diluted with aqueous sodium chloride solution (e.g., an about 20% (e.g., 20%) by weight sodium chloride solution) and extracted with ethyl acetate. The ethyl acetate extract can then be treated with HCl aqueous solution (e.g., an about 3N (e.g., 3N) HCl$_{(aq)}$ solution) and the 3-benzyl-5-(4-methoxyphenyl)pyrazin-2-amine hydrochloride salt product (5) can be isolated by filtration with a purity of about 75% to about 95% (e.g., 75% to 95%).

In some embodiments, (b) further includes a second step of deprotecting the 3-benzyl-5-(4-methoxyphenyl)pyrazin-2-amine (5), or salt thereof, to provide the 4-(5-amino-6-benzylpyrazin-2-yl)phenol (7) (coelenteramine). The deprotection can include subjecting the 3-benzyl-5-(4-methoxyphenyl)pyrazin-2-amine (5) to pyridinium chloride. Treatment with pyridinium chloride can proceed at an elevated temperature of about 180 to about 220° C. (e.g., 180 to 220° C., or 200° C.) at atmospheric pressure. In some embodiments, the elevated temperature can cause the pyridinium chloride to separate from the reaction mixture by evaporation from the reaction mixture. Alternatively, in certain embodiments, deprotection can include subjecting the 3-benzyl-5-(4-methoxyphenyl)pyrazin-2-amine (5) to sodium hydride and ethanethiol in N,N'-dimethyl-formamide (DMF). When treated with sodium hydride and ethanethiol in DMF, the reaction mixture can be at a temperature of about 90° C. to about 120° C. (e.g., about 100° C. to 110° C., 90° C. to 120° C., or 100° C. to 110° C.) and/or for a period of about 15 minutes to about 5 hours (e.g., about 30 minutes to about 2 hours, about 30 minutes to about 1 hour, 30 minutes to 2 hours, 30 minutes to 1 hour, or 30 minutes). Once the reaction is complete, the mixture can be cooled to about 30° C. to about 50° C. (e.g., about 35° C. to about 45° C., about 40° C., 35° C. to 45° C., or 40° C.), extracted with water and an organic solvent (e.g., ethyl acetate). The organic layer can then be separated, refluxed, and then cooled to about 5° C. to 20° C. (e.g., about 10° C. to 15° C., 5° C. to 20° C., or 10° C. to 15° C.), the 4-(5-amino-6-benzylpyrazin-2-yl)phenol (7) (coelenteramine) can be isolated by filtration. In both deprotection methods, the coelenteramine can be optionally purified by washing with an aqueous sodium hydroxide/dioxane solution, stirring with activated charcoal/silica, filtration, followed by precipitation by acidification of the filtrate, and isolation of the precipitated product by filtration. The deprotection can provide 4-(5-amino-6-benzylpyrazin-2-yl)phenol (7) (coelenteramine) in a yield of about 90% to about 100% (e.g., 90% to 100%, at least about 95%, at least 95%, at least about 98%, at least 98%, at least about 99%, or at least 99%) at a purity of about 85% to about 100% (e.g., 85% to 100%, about 90%, or 90%) relative to 3-benzyl-5-(4-methoxyphenyl)pyrazin-2-amine (5).

In some embodiments, coelenteramine is synthesized by (a) reacting 3,5-dibromopyrazin-2-amine and (bromomethyl)benzene in the presence of zinc, iodine, and a first palladium catalyst to provide 3-benzyl-5-bromopyrazin-2-amine (2); (b) reacting 3-benzyl-5-bromopyrazin-2-amine (2) with 4-methoxyphenyl boronic acid (4) in the presence of a palladium catalyst in a first step to provide a hydrochloride salt of 3-benzyl-5-(4-methoxyphenyl)pyrazin-2-amine (5), and deprotecting the hydrochloride salt of 3-benzyl-5-(4-methoxyphenyl)pyrazin-2-amine (5) in a second step to provide 4-(5-amino-6-benzylpyrazin-2-yl)phenol (7) (coelenteramine).

In some embodiments, coelenteramine is synthesized by reacting pyrazin-2-amine with benzyl chloride to provide 3-benzylpyrazin-2-amine; reacting 3-benzylpyrazin-2-amine (25) with N-bromosuccinimide to provide 3-benzyl-5-bromopyrazin-2-amine (2); and reacting the 3-benzyl-5-bromopyrazin-2-amine (2) in two sequential steps to provide 4-(5-amino-6-benzylpyrazin-2-yl)phenol (7) (coelenteramine). The two sequential steps for providing coelenteramine from 3-benzyl-5-bromopyrazin-2-amine (2) can include a first step of reacting the 3-benzyl-5-bromopyrazin-2-amine (2) with silyl-protected 4-bromophenol in the presence of magnesium and a palladium catalyst to provide silyl-protected 4-(5-amino-6-benzylpyrazin-2-yl)phenol. In some embodiments, the palladium catalyst is tetrakis(triphenylphosphine)palladium(0), which can be present in an amount of 1 percent or more (e.g., 2 percent or more, 3 percent or more, 4 percent or more, 5 percent or more, 6 percent or more, 7 percent or more, 8 percent or more, or 9 percent or more) and/or 10 percent or less (e.g., 9 percent or less, 8 percent or less, 7 percent or less, 6 percent or less, 5 percent or less, 4 percent or less, 3 percent or less, or 2 percent or less) by weight relative to the 3-benzyl-5-bromopyrazin-2-amine (2). For example, for every 100 grams of 3-benzyl-5-bromopyrazin-2-amine (2), 1 to 10 grams (e.g., 1 gram, 2 grams, 3 grams, or 5 grams) of palladium catalyst can be used. As an example, for every 100 grams of 3-benzyl-5-bromopyrazin-2-amine (2), 1 gram of palladium catalyst can be used. The two sequential steps can include a second step of deprotecting the silyl-protected 4-(5-amino-6-benzylpyrazin-2-yl)phenol to provide the 4-(5-amino-6-benzylpyrazin-2-yl)phenol (7), for example by subjecting the silyl-protected 4-(5-amino-6-benzylpyrazin-2-yl)phenol to aqueous HCl. This synthesis procedure reduces or eliminates the use of: n-butyl lithium-in the first step of the synthesis, by replacing the n-butyl lithium reaction in toluene with benzyl chloride and THF (tetrahydrofuran). Thus, this synthesis presents the ability to scale up the reaction chemistry and can reduce the cost of the synthesis. In addition, the changes can improve the overall safety of the chemistry by replacing highly reactive materials with more stable materials. The omission of boronic acid compounds in the synthesis can greatly reduce the amount of expensive palladium catalyst in the reaction.

In some embodiments, coelenteramine is synthesized by reacting pyrazin-2-amine (24) with benzyl chloride to provide 3-benzylpyrazin-2-amine (25) (e.g., under Grignard conditions, such as by first providing a solution of magnesium, iodine, and ethyl bromide in a solvent before reacting pyrazin-2-amine (24) with benzyl chloride to provide 3-benzylpyrazin-2-amine (25); reacting 3-benzylpyrazin-2-amine (25) with N-bromosuccinimide to provide 3-benzyl-5-bromopyrazin-2-amine (2); reacting 3-benzyl-5-bromopyrazin-2-amine (2) with 4-methoxyphenyl boronic acid (4) in the presence of a palladium catalyst in a first step to provide a hydrochloride salt of 3-benzyl-5-(4-methoxyphenyl)pyrazin-2-amine (5), and deprotecting the hydrochloride salt of 3-benzyl-5-(4-methoxyphenyl)pyrazin-2-amine (5) in a second step to provide 4-(5-amino-6-benzylpyrazin-2-yl)phenol (7) (coelenteramine). In some embodiments, the deprotection of 3-benzyl-5-(4-methoxyphenyl)pyrazin-2-amine (5) includes exposing the 3-benzyl-5-(4-methoxyphenyl)pyrazin-2-amine (5) to an acidic environment, such as HBr in acetic acid, to provide 4-(5-amino-6-benzylpyrazin-2-yl)phenol (7) (coelenteramine).

The reaction of 3-benzylpyrazin-2-amine (25) with N-bromosuccinimide can be carried out in an organic solvent, such as CHCl$_3$ (chloroform) at room temperature (e.g., about 22° C. to 23° C., 22° C. to 23° C., or 22° C.) at atmospheric pressure (i.e., about 1 atm, or 1 atm). Once the reaction is complete, the reaction mixture can be washed with water, and/or an aqueous acid (e.g., HCl$_{(aq)}$, and 3-benzyl-5-bromopyrazin-2-amine (2) can be isolated by removing the organic solvent under reduced pressure. In some embodiments, 3-benzyl-5-bromopyrazin-2-amine (2) is provided in a yield of about 60% to about 85% (e.g., 70-75%) relative to 3-benzylpyrazin-2-amine (25) and in a purity of at least about 85% (e.g., a purity of about 85% to about 95%, a purity of about 85% to about 100%, a purity of 85% to 95%, a purity of 90-95%, or a purity of 85% to 100%).

In some embodiments, the 3-benzyl-5-bromopyrazin-2-amine (2) is reacted with 4-methoxyphenyl boronic acid (4) in the presence of a palladium catalyst to provide 3-benzyl-5-(4-methoxyphenyl)pyrazin-2-amine (5), or salt thereof. The palladium catalyst can be a palladium (0) catalyst, for example, tetrakis(triphenylphosphine)palladium(0), or a palladium (II) catalyst, such as bis(benzonitrile) palladium (II) dichloride. When a palladium (II) catalyst is used, the reaction mixture can further include 1,4-bis(diphenylphosphino)butane, for example, in an amount of about 5 to about 10 (e.g., 5 to 10) mole percent relative to the 3-benzyl-5-bromopyrazin-2-amine (2). The palladium catalyst can be present in an amount of about 5 to about 10 percent by weight (e.g., 5 to 10 percent by weight) relative to the 3-benzyl-5-bromopyrazin-2-amine (2). The first step in (b) can include about 1:1 to about 1:1.3 molar equivalent of the 3-benzyl-5-bromopyrazin-2-amine (2) to 4-methoxyphenyl boronic acid (4). In some embodiments, the 3-benzyl-5-bromopyrazin-2-amine (2) and the 4-methoxyphenyl boronic acid (4) are reacted together for a duration of about 120 minutes to about 300 minutes (e.g., 120 minutes to 300 minutes). The reaction solvent can include 1,4-dioxane and/or water. In some embodiments, the reaction mixture further includes potassium carbonate in an amount of about 75 to about 85 mole percent relative to the 3-benzyl-5-bromopyrazin-2-amine (2). The 3-benzyl-5-bromopyrazin-2-amine (2) and the 4-methoxyphenyl boronic acid (4) can be reacted together for a duration of about 12 to about 36 hours (e.g., about 20 to 24 hours, about 12 to about 24 hours, or about 15 to 24 hours), and/or at a temperature of about 80 to about 110° C. (e.g., 80 to 100° C., or 80 to 85° C.), and/or at atmospheric pressure (i.e., a pressure of about 1 atm, or 1 atm). The 3-benzyl-5-(4-methoxyphenyl)pyrazin-2-amine (5), or salt thereof, can be provided in a yield of about 65% to about 95% (e.g., 85% to 90%, 80% to 95%, or 85% to 90%) relative to the 3-benzyl-5-bromopyrazin-2-amine (2), at a purity of for example, 90% to 95% (e.g., 92% to 95%). The 3-benzyl-5-(4-methoxyphenyl)pyrazin-2-amine (5) can be isolated by diluting the reaction mixture with water and extracting with ethyl acetate. The ethyl acetate extract can be removed from the extract under reduced pressure to provide 3-benzyl-5-(4-methoxyphenyl)pyrazin-2-amine (5).

The 3-benzyl-5-(4-methoxyphenyl)pyrazin-2-amine (5), or salt thereof, regardless of whether obtained with a palladium (0) or palladium (II) catalyst, can be isolated by precipitation of the 3-benzyl-5-(4-methoxyphenyl)pyrazin-2-amine (5) as a hydrochloride salt. Precipitation is advantageous as it can eliminate column chromatography, which can be laborious, costly, and time-consuming; and/or can also increase yield relative to column chromatography. In some embodiments, isolating the 3-benzyl-5-(4-methoxyphenyl)pyrazin-2-amine (5) does not include chromatography (e.g., liquid chromatography), does not include recrystallization, or does not include chromatography and recrystallization. In some embodiments, the reaction mixture from the reaction of 3-benzyl-5-bromopyrazin-2-amine (2) with (4-methoxyphenyl)boronic acid is diluted with aqueous sodium chloride solution (e.g., an about 20% (e.g., 20%) by weight sodium chloride solution) and extracted with ethyl acetate. The ethyl acetate extract can then be treated with HCl aqueous solution (e.g., an about 3N (e.g., 3N) HCl$_{(aq)}$ solution) and the 3-benzyl-5-(4-methoxyphenyl)pyrazin-2-amine hydrochloride salt product (5) can be isolated by filtration with a purity of about 75% to about 95% (e.g., 75% to 95%).

The 3-benzyl-5-(4-methoxyphenyl)pyrazin-2-amine (5), or salt thereof, can then be deprotected to provide 4-(5-amino-6-benzylpyrazin-2-yl)phenol (7) (coelenteramine). In some embodiments, the deprotection includes exposing the 3-benzyl-5-(4-methoxyphenyl)pyrazin-2-amine (5), or salt thereof, to an acid (e.g., HBr and acetic acid). For example, the HBr can have an HBr concentration of 48% in water, and the aqueous HBr can be mixed with acetic acid in a ratio of from about 1:2 (e.g., from about 1:1.5, from about 1:1.25) to about 1:1 (e.g., to about 1:1.25, or to about 1:1.5). The deprotection can occur at a temperature of from about 100° C. (e.g., from about 105° C., from about 110° C., from about 115° C.) to about 120° C. (e.g., to about 115° C., to about 110° C., to about 105° C.) for a duration of from about 5 hours (e.g., from about 8 hours, from about 10 hours, from about 12 hours, or from about 14 hours) to about 18 hours (e.g., to about 14 hours, to about 12 hours, to about 10 hours, or to 8 hours), for example, from 8 to 10 hours, at atmospheric pressure. After the deprotection reaction, the reaction mixture can be cooled, extracted with an organic solvent (such as ethyl acetate), and the organic solvent can be removed under reduced pressure. The residue can then be refluxed with a hydrocarbon (such as cyclohexane), filtered, isolated, and dried to provide 4-(5-amino-6-benzylpyrazin-2-yl)phenol (7) (coelenteramine). The 4-(5-amino-6-benzylpyrazin-2-yl)phenol (7) (coelenteramine) can be obtained in an yield of from about 70% (e.g., from about 75%, from about 80%, or from 85%) to about 90% (e.g., to about 85%, to about 80%, or to about 75%), for example, from 75% to 80%, at a purity of from about 85% (e.g., from about 87%, from about 90%, or from about 92%) to about 95% (e.g., to about 92%, (e.g., to about 90%, or to about 87%), for example, a purity of about 90%, relative to 3-benzyl-5-(4-methoxyphenyl)pyrazin-2-amine (5).

Protected 1,1-diethoxy-3-(4-hydroxyphenyl)propan-2-one Synthesis

In some embodiments, the silyl protected 1,1-diethoxy-3-(4-hydroxyphenyl)propan-2-one is 3-(4-((tert-butyldimethylsilyl)oxy)phenyl)-1,1-diethoxypropan-2-one (23). The 3-(4-((tert-butyldimethylsilyl)oxy)phenyl)-1,1-diethoxypropan-2-one (23) can be synthesized by: i) reacting 4-hydroxybenzaldehyde (8) with tert-butyldimethylsilyl chloride to provide 4-((tert-butyldimethylsilyl)oxy)benzaldehyde (20a); ii) reacting the 4-((tert-butyldimethylsilyl)oxy)benzaldehyde with sodium borohydride to provide (4-((tert-butyldimethylsilyl)oxy)phenyl)methanol (20b); iii) reacting the (4-((tert-butyldimethylsilyl)oxy)phenyl)methanol with methanesulfonyl chloride in the presence of a base (e.g., triethylamine) to provide tert-butyl(4-(chloromethyl)phenoxy)dimethylsilane (21); iv) reacting the tert-butyl(4-(chloromethyl)phenoxy)dimethylsilane with magnesium, to provide (4-((tert-butyldimethylsilyl)oxy)benzyl)magnesium chloride (22); and v) reacting the (4-((tert-butyldimethylsilyl)oxy)benzyl)magnesium chloride with ethyl 2,2-diethoxyacetate to provide the 3-(4-((tert-butyldimethylsilyl)oxy)phenyl)-1,1-diethoxypropan-2-one (23).

In some embodiments, the tert-butyldimethylsilyl protected 1,1-diethoxy-3-(4-hydroxyphenyl)propan-2-one can degrade in acidic conditions, and can be stabilized in a basic environment. Thus, a base can be added to the reaction mixture and/or during purification. For example, the tert-butyl(4-(chloromethyl)phenoxy)dimethylsilane (21) can be purified by chromatography with an eluant that includes triethylamine. In some embodiments, the 3-(4-((tert-butyldimethylsilyl)oxy)phenyl)-1,1-diethoxypropan-2-one (23) is further purified by chromatography with an eluant comprising triethylamine.

The 3-(4-((tert-butyldimethylsilyl)oxy)phenyl)-1,1-diethoxypropan-2-one (23) can be provided in a yield of about 20% to about 40% (e.g., 20% to 40%, about 20% to 25%, or 20% to 25%) relative to tert-butyl(4-(chloromethyl)phenoxy)dimethylsilane (21), at a purity of about 85% to about 95% (e.g., 85% to 95%, about 90%, or 90%).

1,1-diethoxy-3-(4-hydroxyphenyl)propan-2-one (14)

1,1-diethoxy-3-(4-hydroxyphenyl)propan-2-one (14) can be made, for example, according to the reaction scheme below.

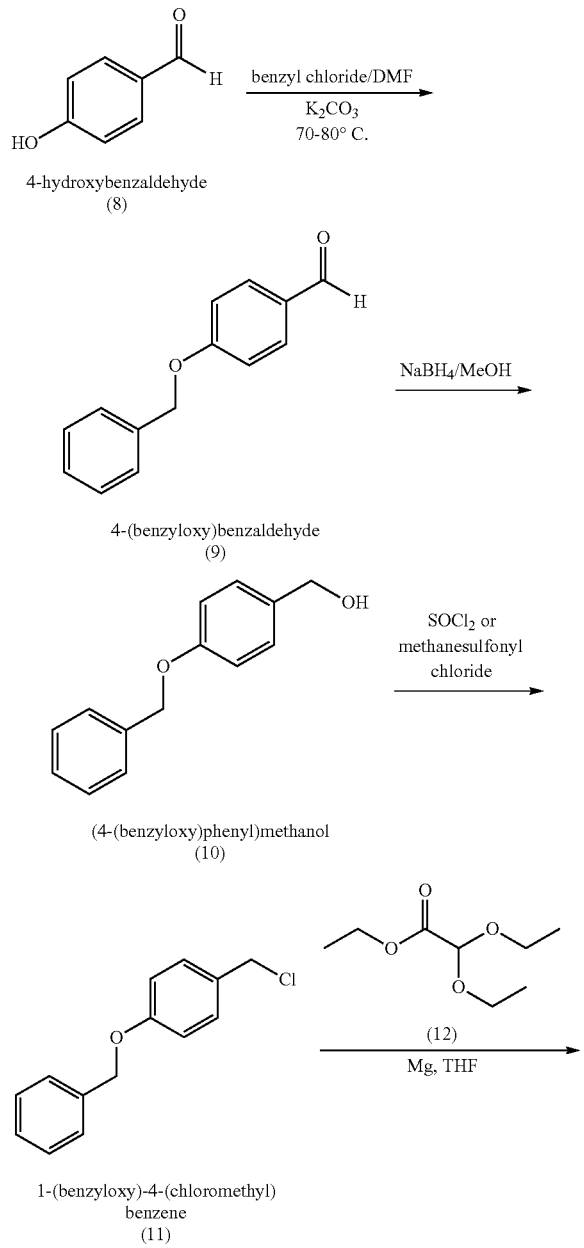

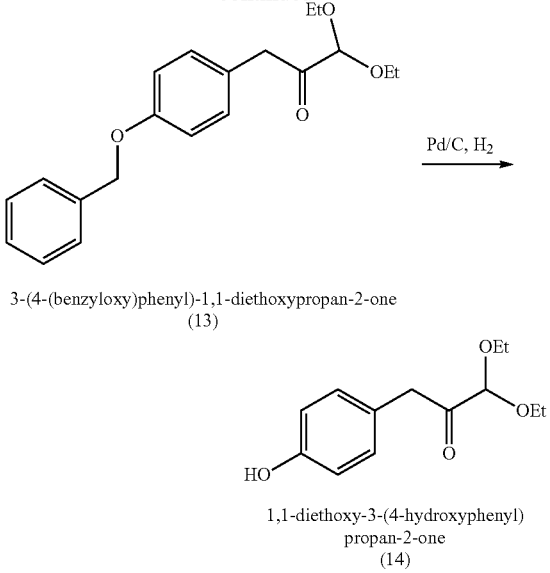

Synthesis of 3-(4-((tert-butyldimethylsilyl)oxy)phenyl)-1,1-dimethoxypropan-2-one)

In some embodiments, 4-(tert-butyldimethylsiloxy) benzyl chloride can be as synthesized above, and can be reacted in a Grignard reaction with methyl 2,2-dimethoxyacetate to provide 3-(4-((tert-butyldimethylsilyl)oxy)phenyl)-1,1-dimethoxypropan-2-one). For example, the 4-(tert-butyldimethylsiloxy) benzyl chloride can be reacted with methyl 2,2-dimethoxyacetate in a Grignard reaction with Mg, and $I_2$ and dibromoethane as Grignard initiators to provide 3-(4-((tert-butyldimethylsilyl)oxy)phenyl)-1,1-dimethoxypropan-2-one).

Synthesis of 3-(4-(benzyloxy)phenyl)-2-oxopropanal

In some embodiments, the present disclosure features a method of making 3-(4-(benzyloxy)phenyl)-2-oxopropanal, including providing 1-(benzyloxy)-4-(chloromethyl)benzene, and reacting the 1-(benzyloxy)-4-(chloromethyl)benzene in two steps to provide 3-(4-(benzyloxy)phenyl)-2-oxopropanal. The method of making 3-(4-(benzyloxy)phenyl)-2-oxopropanal does not include more than one palladium-catalyzed reaction, from an initial starting material of 4-hydroxybenzaldehyde.

The method can include a first step of reacting the 1-(benzyloxy)-4-(chloromethyl)benzene with methyl 2,2-dimethoxyacetate under Grignard conditions (e.g., ethyl bromide, magnesium, and a catalytic amount of iodine) to provide 3-(4-(benzyloxy)phenyl)-1,1-dimethoxypropan-2-one. The 3-(4-(benzyloxy)phenyl)-1,1-dimethoxypropan-2-one can be purified by silica column chromatography.

The method can include a second step of reacting the 3-(4-(benzyloxy)phenyl)-1,1-dimethoxypropan-2-one with acid (e.g., aqueous acid, such as 10% aqueous HCl)) to provide the 3-(4-(benzyloxy)phenyl)-2-oxopropanal. The 3-(4-(benzyloxy)phenyl)-2-oxopropanal can be isolated in a yield of 60 to 75% (e.g., 65% to 70%) at a purity of 85 to 95% (e.g., 90%) relative to 1-(benzyloxy)-4-(chloromethyl)benzene.

In some embodiments, the intermediate 1-(benzyloxy)-4-(chloromethyl)benzene can be made, for example, by the following procedure. A mixture of 4-hydroxybenzaldehyde (8), benzyl chloride, and anhydrous potassium carbonate in N,N-dimethyl formamide can be formed, heated to a temperature of about 40-80° C. for a duration of from, for example, 5 hours to 3 days, under atmospheric pressure. After reaction completion, the mixture can be cooled to room temperature, charged with water, and centrifuged or filtered to isolate the resulting 4-(benzyloxy)benzaldehyde.

The 4-(benzyloxy)benzaldehyde can then be reduced with sodium borohydride to provide (4-(benzyloxy)phenyl)methanol. Briefly, the sodium borohydride can be added at a temperature of about 45 to 50° C. dropwise to a solution of 4-(benzyloxy)benzaldehyde in methanol. The reaction mixture can then be cooled (e.g., to about 15° C.), acidified (e.g., with acetic acid), stirred with water, and the product can be isolated by filtration. The resultant product can be heated with an organic solvent (e.g., n-hexane), filtered, and dried to provide (4-(benzyloxy)phenyl)methanol.

The (4-(benzyloxy)phenyl)methanol can then be reacted with thionyl chloride to provide 1-(benzyloxy)-4-(chloromethyl)benzene (11). For example, a mixture of (4-(benzyloxy)phenyl)methanol in dichloromethane and N,N'-dimethylformamide can be formed, to which thionyl chloride can be added slowly at a temperature of from about 30 to about 35° C. After stirring the reaction for a duration of from about 30 minutes to about 2 hours, the solvent can be removed, and the residue can be extracted with water and an organic solvent, such as ethyl acetate. After separating the organic layer, the pH of the layer can be adjusted to about 8 to 9 with an aqueous base, such as a soda ash aqueous solution, then the organic layer can be separated again, washed with a sodium chloride aqueous solution, and the organic layer is then separated and concentrated under reduced pressure. The residue can then be washed with an organic solvent, such as n-hexane, and the product can be isolated by filtration and dried to obtain the intermediate 1-(benzyloxy)-4-(chloromethyl)benzene.

Coelenterazine

In some embodiments, the coelenterazine is obtained by coupling the 4-(5-amino-6-benzylpyrazin-2-yl)phenol (7) with silyl-protected 1,1-diethoxy-3-(4-hydroxyphenyl)propan-2-one or silyl-protected 1,1-dimethoxy-3-(4-hydroxyphenyl)propan-2-one to provide coelenterazine, or a salt thereof. Alternatively, in some embodiments, the coelenterazine is obtained by coupling 4-(5-amino-6-benzylpyrazin-2-yl)phenol (7) with 1,1-diethoxy-3-(4-hydroxyphenyl)propan-2-one (14) to provide coelenterazine, or a salt thereof. The coupling step, whether with silyl-protected 1,1-diethoxy-3-(4-hydroxyphenyl)propan-2-one, silyl-protected 1,1-dimethoxy-3-(4-hydroxyphenyl)propan-2-one, or with 1,1-diethoxy-3-(4-hydroxyphenyl)propan-2-one (14), can be conducted in the presence of dioxane, water, and HCl (e.g., at a ratio of about 90:5:5 dioxane to water to HCl; or at an HCl at 35%-38% concentration (i.e., concentrated HCl) to water ratio about 10: about 1 (e.g., 10:1) to about 1: about 1 (e.g., 1:1), where the dioxane: (HCl+$H_2O$) ratio is about 9:1); and/or can be conducted at a temperature of about 60 to about 90° C. (e.g., 60 to 90° C.) and at a pressure of about 1 atm (e.g., 1 atm); and/or can proceed for a duration of about 16 hours to about 28 hours (e.g., 16 to 28 hours).

In some embodiments, whether the 4-(5-amino-6-benzylpyrazin-2-yl)phenol (7) is coupled with silyl-protected 1,1-diethoxy-3-(4-hydroxyphenyl)propan-2-one, silyl-protected 1,1-dimethoxy-3-(4-hydroxyphenyl)propan-2-one, or with 1,1-diethoxy-3-(4-hydroxyphenyl)propan-2-one (14), the coupling reaction can be conducted in a solvent mixture of dioxane, methanol, and isopropyl alcohol. The methanol and the isopropyl alcohol can each independently be in the solvent mixture at a concentration of 3% or more (e.g., 5% or more, 7% or more, or 9% or more and/or 10% or less (e.g., 9% or less, 7% or less, or 5% or less) by volume. In certain embodiments, the methanol and the isopropyl alcohol are each independently in the solvent mixture at a concentration of about 5% (e.g., 5%) by volume. In some embodiments, the 4-(5-amino-6-benzylpyrazin-2-yl)phenol (7) is reacted in the solvent mixture of dioxane, methanol, and isopropyl alcohol with silyl-protected 1,1-diethoxy-3-(4-hydroxyphenyl)propan-2-one, such as 3-(4-((tert-butyldimethylsilyl)oxy)phenyl)-1,1-diethoxypropan-2-one (23). Without wishing to be bound by theory, it is believed that methanol can favor the reaction kinetics and yield by increasing the solubility of the 4-(5-amino-6-benzylpyrazin-2-yl)phenol (7) in the solvent mixture, thereby increasing its availability for reaction with silyl-protected 1,1-diethoxy-3-(4-hydroxyphenyl)propan-2-one, silyl-protected 1,1-dimethoxy-3-(4-hydroxyphenyl)propan-2-one, or with 1,1-diethoxy-3-(4-hydroxyphenyl)propan-2-one (14). In some embodiments, the coupling reaction can be conducted at a temperature of about 60 to about 90° C. (e.g., about 70° C. to 85° C., about 80° C., or 80° C.) and at a pressure of about 1 atm (e.g., 1 atm); and/or can proceed for a duration of about 24 hours to about 36 hours (e.g., 24 to 36 hours, or 36 hours).

In some embodiments, the 4-(5-amino-6-benzylpyrazin-2-yl)phenol (7) is coupled with silyl-protected 1,1-diethoxy-3-(4-hydroxyphenyl)propan-2-one (e.g., 3-(4-((tert-butyldimethylsilyl)oxy)phenyl)-1,1-diethoxypropan-2-one (23)), silyl-protected 1,1-dimethoxy-3-(4-hydroxyphenyl)propan-2-one, or with 1,1-diethoxy-3-(4-hydroxyphenyl)propan-2-one (14) at a molar ratio of about 1:1.3 to about 1:2. In certain embodiments, the 4-(5-amino-6-benzylpyrazin-2-yl)phenol (7) is coupled with silyl-protected 1,1-diethoxy-3-(4-hydroxyphenyl)propan-2-one (e.g., 3-(4-((tert-butyldimethylsilyl)oxy)phenyl)-1,1-diethoxypropan-2-one (23)) at a molar ratio of about 1:1.3 to about 1.2 (e.g., about 1:1.3, or 1:1.3).

In certain embodiments, whether the 4-(5-amino-6-benzylpyrazin-2-yl)phenol (7) is coupled with silyl-protected 1,1-diethoxy-3-(4-hydroxyphenyl)propan-2-one, silyl-protected 1,1-dimethoxy-3-(4-hydroxyphenyl)propan-2-one, or with 1,1-diethoxy-3-(4-hydroxyphenyl)propan-2-one (14), the coupling reaction is monitored by reverse phase HPLC and stopped when 4-(5-amino-6-benzylpyrazin-2-yl)phenol (7) stops depleting, or when coelenterazine starts to decompose. Without wishing to be bound by theory, it is believed that the reverse phase HPLC monitoring can be important, as the coelenterazine can start to decompose or degrade after the coelenteramine stops depleting.

In some embodiments, stopping the reaction mixture includes cooling the reaction mixture (e.g., to room temperature, about 23° C., or 23° C.), and optionally stirring the reaction mixture with activated carbon and silica. The coelenterazine or a salt thereof can then be isolated by filtering the reaction mixture (if activated carbon and silica are used), by removal of solvents (e.g., under reduced pressure), trituration with ethyl acetate, followed by filtration to obtain the solid coelenterazine. In some embodiments, the coelenterazine is isolated as a salt, such as a hydrochloride salt.

In some embodiments, when silyl-protected 1,1-diethoxy-3-(4-hydroxyphenyl)propan-2-one or silyl-protected 1,1-dimethoxy-3-(4-hydroxyphenyl)propan-2-one is used as one of the starting materials in the coupling reaction, the coelenterazine or a salt thereof is obtained in a yield of about 50% to about 70% (e.g., 50% to 70%) relative to the 4-(5-amino-6-benzylpyrazin-2-yl)phenol (7), at a purity of about 55% to about 70% (e.g. 55% to 70%).

In some embodiments, when 1,1-diethoxy-3-(4-hydroxyphenyl)propan-2-one (14) is used as one of the starting materials in the coupling reaction, coelenterazine or a salt thereof is obtained in a yield of about 60% to about 70% (e.g., 60% to 70%) relative to the 4-(5-amino-6-benzylpyrazin-2-yl)phenol (7), at a purity of about 60% to about 75% (e.g., 60% to 75%). In some embodiments, the coelenterazine (or salt thereof) is obtained at a purity of 60% to 65% in the isolated composition. Without wishing to be bound by theory, it is believed that the isolated coelenterazine, or salt thereof, is stabilized (e.g., protected from degradation) by the presence of an amount of 4-(5-amino-6-benzylpyrazin-2-yl)phenol (7) (coelenteramine). Thus, the isolated composition can include coelenterazine (or salt thereof) at an amount of 60% to 65% by weight and 4-(5-amino-6-benzylpyrazin-2-yl)phenol (7) (coelenteramine). In some embodiments, the isolated composition consists essentially of coelenterazine (or salt thereof) at an amount of 60% to 65% by weight and 4-(5-amino-6-benzylpyrazin-2-yl)phenol (7) (coelenteramine); such that impurities present in the composition do not substantially contribute (e.g., contribute more than 10%, more than 5%, or more than 1%) to the luminescence of the coelenterazine, or salt thereof.

The relative amount of coelenterazine (or salt thereof) to 4-(5-amino-6-benzylpyrazin-2-yl)phenol (7) (coelenteramine) in the isolated composition can be assessed by liquid chromatography-mass spectrometry (LC-MS). For example, a 1 mg/ml methanolic solution of the isolated coelenterazine composition can be diluted ten times into an injection solvent consisting of 70:30 reagent water:acetonitrile (v/v), each supplemented with 0.05% formic acid. The diluted solution including the isolated coelenterazine composition is separated by LC on a C-18 reverse phase column using a gradient elution. In some embodiments, the separation provides a response for coelenterazine (or salt thereof) at about 1.7 min and a response for coelenteramine (7) at about 2.5 min. Tandem MS is configured to monitor the (M+H)+ parent ion of each compound which is subsequently fragmented into its characteristic daughter ion. The daughter ion intensity creates the chromatographic signal for each compound which is then integrated to produce an area for the signal. The parent ion for coelenterazine is 424.1 Da with a daughter ion at 302.2 Da. The parent ion for coelenteramine is 278.1 Da and its daughter is 132.0 Da. In some embodiments, the ratio of the coelenterazine (or salt thereof) to coelenteramine in the isolated composition is about 20:1 or more (e.g., about 24:1 or more, about 30:1 or more, about 40:1 or more, about 50:1 or more, about 60:1 or more, about 70:1 or more, about 80:1 or more, or about 90:1 or more) and/or about 100:1 or less (e.g., about 90:1 or less, about 80:1 or less, about 70:1 or less, about 60:1 or less, about 50:1 or less, about 40:1 or less, about 30:1 or less, or about 24:1 or less). In certain embodiments, the ratio of the coelenterazine (or salt thereof) to coelenteramine in the isolated composition is 24:1 or more and/or 80:1 or less. The isolated composition can be incorporated into an article, such as an absorbent article, as will be described below.

In some embodiments, the coelenterazine is obtained by coupling 4-(5-amino-6-benzylpyrazin-2-yl)phenol (coelenteramine) with 3-(4-(benzyloxy)phenyl)-2-oxopropanal to provide 8-benzyl-2-(4-(benzyloxy)benzyl)-6-(4-hydroxyphenyl)imidazo[1,2-α]pyrazin-3(7H)-one; and deprotecting the 8-benzyl-2-(4-(benzyloxy)benzyl)-6-(4-hydroxyphenyl) imidazo [1,2-α] pyrazin-3 (7H)-one to provide 8-benzyl-2-(4-hydroxybenzyl)-6-(4-hydroxyphenyl)imidazo[1,2-α] pyrazin-3(7H)-one (coelenterazine).

Coupling the 4-(5-amino-6-benzylpyrazin-2-yl)phenol (coelenteramine) with the 3-(4-(benzyloxy)phenyl)-2-oxopropanal can occur in a solvent mixture that includes dioxane, water, and HCl (e.g., concentrated HCl, 36% HCl). The coupling reaction can be conducted at a temperature of 75° C. to 90° C. (e.g., 80° C. to 85° C.) for 12 to 36 hours (e.g., 24 hours) in an inert atmosphere.

In some embodiments, deprotecting the 8-benzyl-2-(4-(benzyloxy)benzyl)-6-(4-hydroxyphenypimidazo[1,2-α] pyrazin-3(7H)-one includes a first deprotection step of exposing the 8-benzyl-2-(4-(benzyloxy)benzyl)-6-(4-hydroxyphenyl)imidazo[1,2-α]pyrazin-3(7H)-one to acid, such as HCl (e.g., concentrated HCl, 36% HCl). The reaction mixture can include an organic solvent, such as dioxane. The acid can be present in an amount equal to or in excess of the volume of the solvent mixture in the preceding coupling step. An intermediate deprotected product can be obtained, for example, by filtering the reaction mixture, collecting the solid residue, and drying the solid residue before proceeding to the following step. The first deprotection step can be conducted at a temperature of 25° C. to 40° C. (e.g., 30 to 35° C.), for a duration of from 30 minutes (e.g., from 1 hour) to 2 hours (e.g., to 1.5 hours). The intermediate deprotected product (i.e., the solid residue) can be washed with an organic solvent (e.g., toluene) before filtering and drying.

Deprotecting the 8-benzyl-2-(4-(benzyloxy)benzyl)-6-(4-hydroxyphenyl)imidazo[1,2-α]pyrazin-3(7H)-one can include a second deprotection step of exposing the dried intermediate deprotected product to acid, such as HCl (e.g., concentrated HCl, 36% HCl). The reaction mixture can include an organic solvent, such as dioxane. The second deprotection step can include heating the intermediate deprotected product in HCl and the organic solvent to a first temperature of about 50° C. to 75° C. (e.g., from 60° C. to 70° C., from 55° C. to 65° C., from 60° C. to 62° C.) for a duration of 6 to 24 hours, then at a second higher temperature (e.g., higher than the first temperature by 5° C. to 15° C., by 5° C. to 10° C., by 10° C. to 15° C.) to provide coelenterazine. To isolate the coelenterazine, the HCl and organic solvent can be removed under reduced pressure to provide a residue, the residue can be washed with organic solvents such as ethyl acetate, then dichloromethane, and hexane. The residue can be dried under reduced pressure, at room temperature or up to a temperature of about 50° C. (e.g., 40-45° C.) to provide the final coelenterazine. The coelenterazine can be obtained in a yield of 70% or more (e.g., 70% to 95%, 70% to 85%, 80% to 95%, 80% to 85%, or 80%) at a purity of from 55% to 70% (e.g., 55% to 65%, or 60% to 65%) relative to 4-(5-amino-6-benzylpyrazin-2-yl)phenol.

The 3-(4-(benzyloxy)phenyl)-2-oxopropanal and the coelenteramine used in the coupling reaction to provide coelenterazine can be made by the methods describe above.

Representative Syntheses

In some embodiments, the coelenterazine of the present disclosure can be made according to Schemes A, B, and C, below. Scheme A illustrates the synthesis of coelenteramine (Intermediate I), Scheme B illustrates the synthesis of silyl-protected 1,1-diethoxy-3-(4-hydroxyphenyl)propan-2-one (Intermediate II), and Scheme C illustrates the coupling of coelenteramine and silyl-protected 1,1-diethoxy-3-(4-hydroxyphenyl)propan-2-one to generate coelenterazine.

Scheme A. Synthesis of Intermediate I.

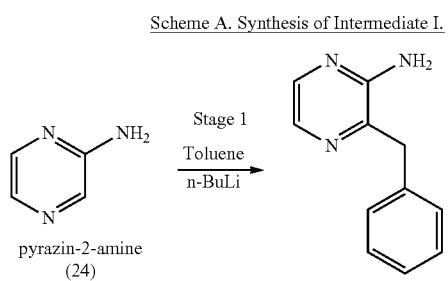

pyrazin-2-amine
(24)

Stage 1
Toluene
n-BuLi 3-benzylpyrazin-2-amine
(25)

Stage 2
NBS
CHCl₃

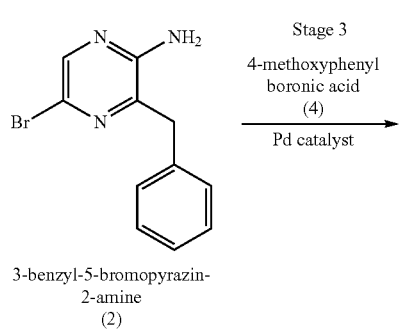

3-benzyl-5-bromopyrazin-2-amine
(2)

Stage 3
4-methoxyphenyl boronic acid
(4)
Pd catalyst

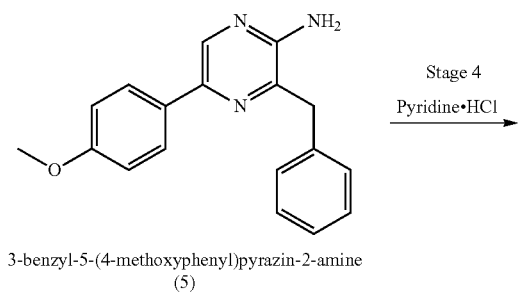

3-benzyl-5-(4-methoxyphenyl)pyrazin-2-amine
(5)

Stage 4
Pyridine•HCl

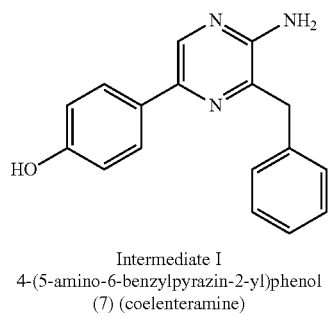

Intermediate I
4-(5-amino-6-benzylpyrazin-2-yl)phenol
(7) (coelenteramine)

Scheme B. Synthesis of Intermediate II.

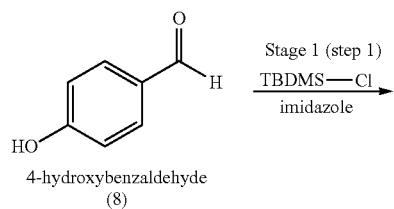

4-hydroxybenzaldehyde
(8)

Stage 1 (step 1)
TBDMS—Cl
imidazole

-continued

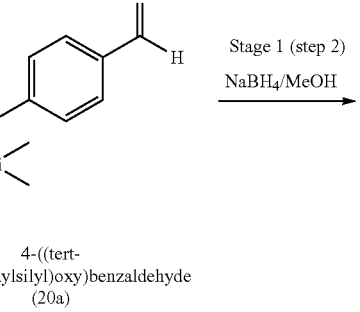

4-((tert-butyldimethylsilyl)oxy)benzaldehyde
(20a)

Stage 1 (step 2)
NaBH₄/MeOH

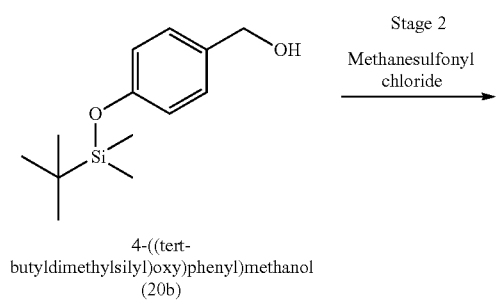

4-((tert-butyldimethylsilyl)oxy)phenyl)methanol
(20b)

Stage 2
Methanesulfonyl chloride

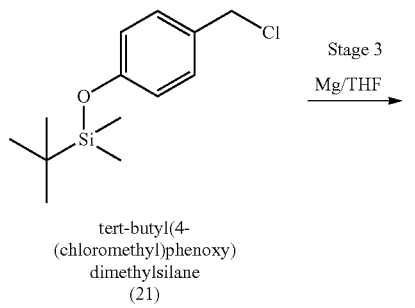

tert-butyl(4-(chloromethyl)phenoxy)dimethylsilane
(21)

Stage 3
Mg/THF

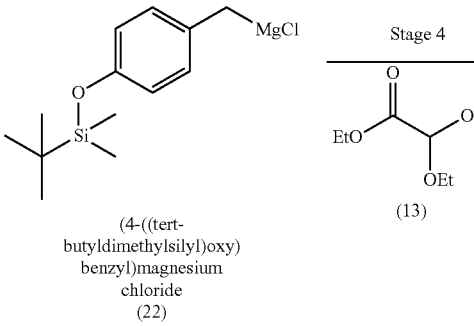

(4-((tert-butyldimethylsilyl)oxy)benzyl)magnesium chloride
(22)

Stage 4

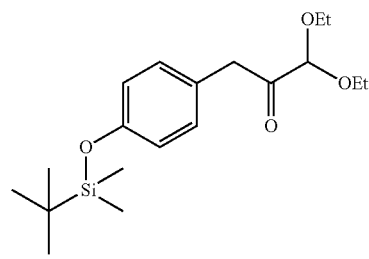

Intermediate II
3-(4-((tert-butyldimethylsilyl)oxy)phenyl)-1,1-diethoxypropan-2-one
(23)

Scheme C. Synthesis of coelenterazine.

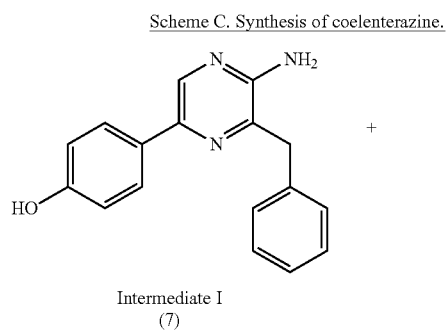

Intermediate I
(7)

+

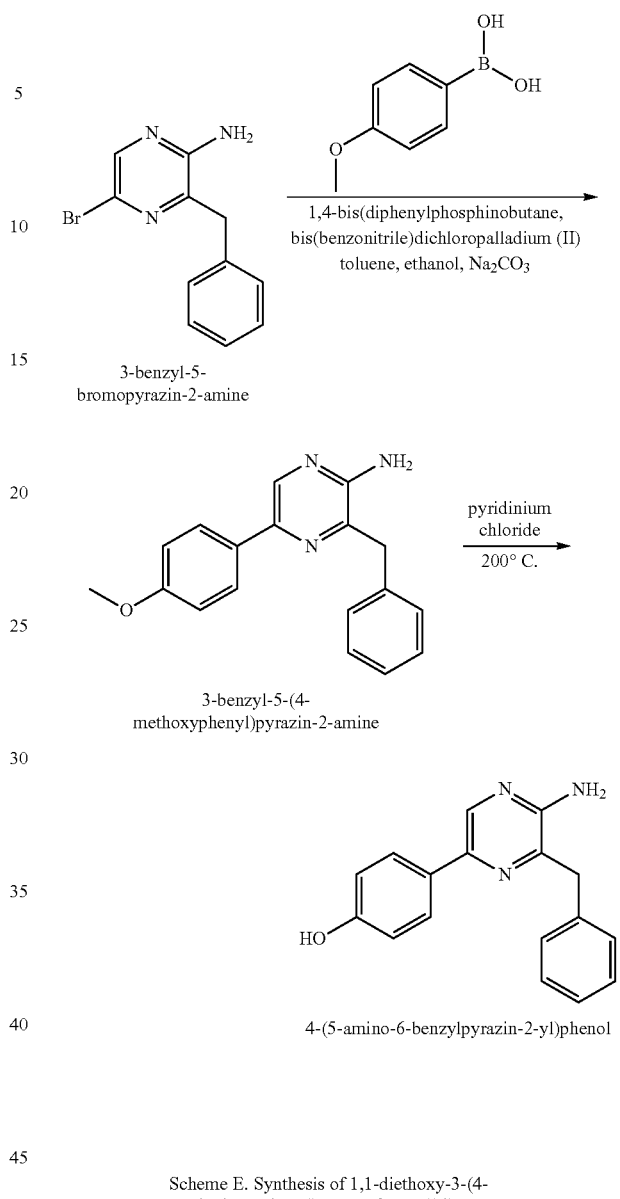

3-benzyl-5-bromopyrazin-2-amine 3-benzyl-5-(4-methoxyphenyl)pyrazin-2-amine 4-(5-amino-6-benzylpyrazin-2-yl)phenol Intermediate II
(23)

coelenterazine
(16)

In some embodiments, the coelenterazine of the present disclosure can be made according to Schemes D, E, and F, below. Scheme D illustrates the synthesis of coelenteramine, Scheme E illustrates the synthesis of 1,1-diethoxy-3-(4-hydroxyphenyl)propan-2-one (14), and Scheme F illustrates the coupling of coelenteramine and 1,1-diethoxy-3-(4-hydroxyphenyl)propan-2-one (14) to generate coelenterazine (16).

Scheme D. Synthesis of coelenteramine.

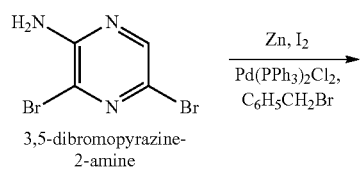

3,5-dibromopyrazine-2-amine

Scheme E. Synthesis of 1,1-diethoxy-3-(4-hydroxyphenyl)propan-2-one (14).

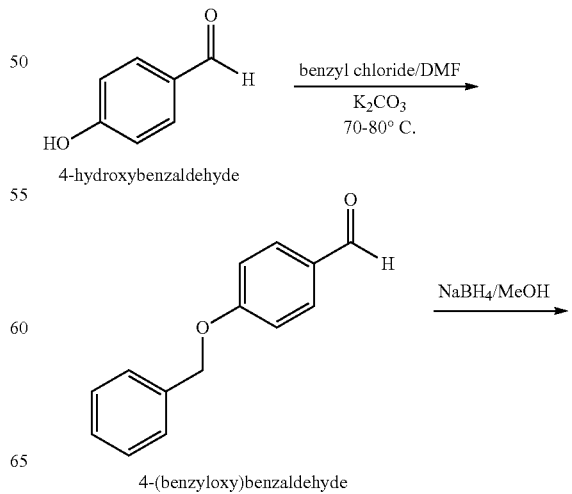

4-hydroxybenzaldehyde 4-(benzyloxy)benzaldehyde

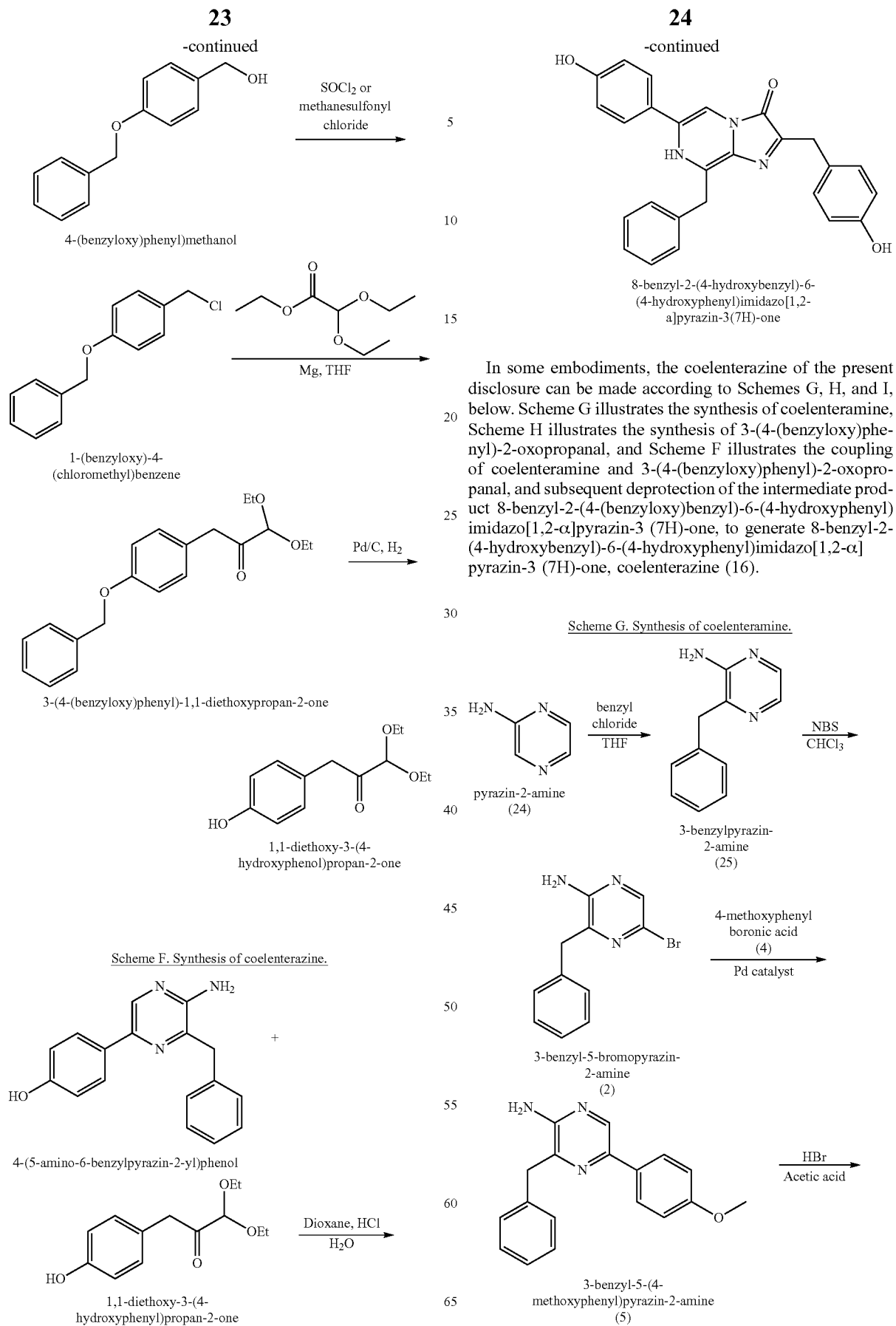

In some embodiments, the coelenterazine of the present disclosure can be made according to Schemes G, H, and I, below. Scheme G illustrates the synthesis of coelenteramine, Scheme H illustrates the synthesis of 3-(4-(benzyloxy)phenyl)-2-oxopropanal, and Scheme F illustrates the coupling of coelenteramine and 3-(4-(benzyloxy)phenyl)-2-oxopropanal, and subsequent deprotection of the intermediate product 8-benzyl-2-(4-(benzyloxy)benzyl)-6-(4-hydroxyphenyl)imidazo[1,2-α]pyrazin-3 (7H)-one, to generate 8-benzyl-2-(4-hydroxybenzyl)-6-(4-hydroxyphenyl)imidazo[1,2-α]pyrazin-3 (7H)-one, coelenterazine (16).

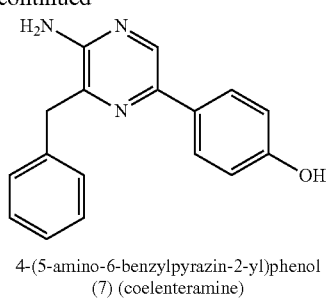
4-(5-amino-6-benzylpyrazin-2-yl)phenol (7) (coelenteramine)
Scheme H. Synthesis of 3-(4-(benzyloxy)phenyl)-2-oxopropanal
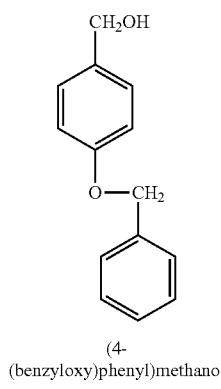
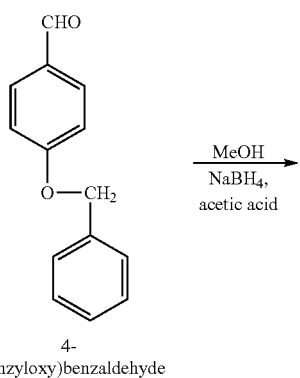
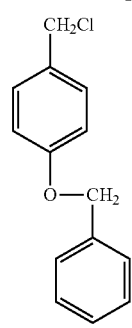
1-(benzyloxy)-4-(chloromethyl)benzene
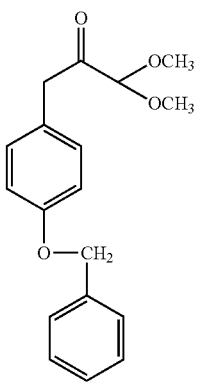
3-(4-(benzyloxy)phenyl)-1,1-dimethoxypropan-2-one
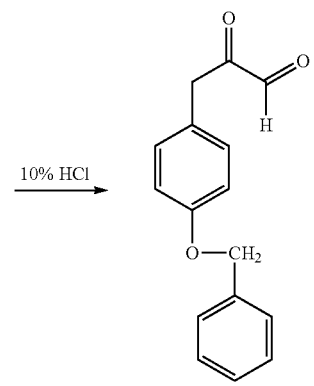
3-(4-(benzyloxy)phenyl)-2-oxopropanal
Scheme I. Synthesis of coelenterazine
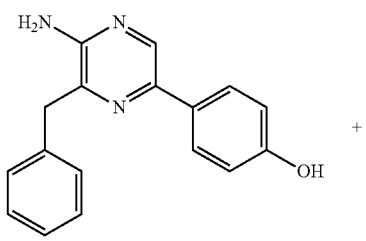
4-(5-amino-6-benzylpyrazin-2-yl)phenol
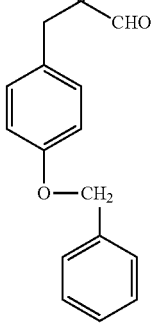
3-(4-(benzyloxy)phenyl)-2-oxopropanal -continued

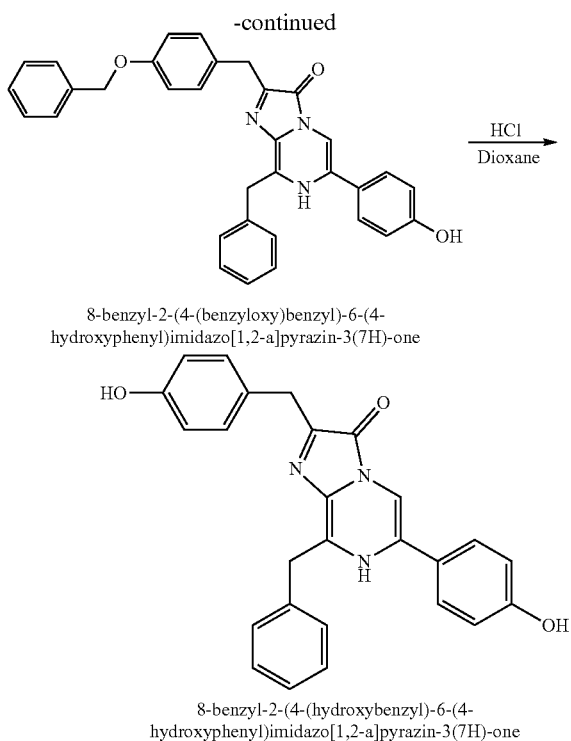

8-benzyl-2-(4-(benzyloxy)benzyl)-6-(4-hydroxyphenyl)imidazo[1,2-a]pyrazin-3(7H)-one 8-benzyl-2-(4-(hydroxybenzyl)-6-(4-hydroxyphenyl)imidazo[1,2-a]pyrazin-3(7H)-one Absorbent Articles The coelenterazine, or salt thereof, made according to the methods of the present disclosure can be incorporated into an absorbent article.

In some embodiments, the present disclosure features an absorbent article, including the coelenterazine, or salt thereof, synthesized by the methods of the present disclosure.

Materials and structural elements for absorbent articles that include one or more components of a chemiluminescent system are described, for example, in U.S. Provisional Application No. 62/692,502, titled "Chemiluminescent Wetness Indicator for Absorbent Products" and filed on Jun. 29, 2018; US Provisional Application No. 62/753,024, titled "Chemiluminescent Wetness Indicator for Absorbent Products" and filed on Oct. 30, 2018; and U.S. application Ser. No. 16/457,732, titled "Chemiluminescent Wetness Indicator for Absorbent Products" and filed on Jun. 28, 2019; the entire content of each of which is incorporated herein by reference.

Chemiluminescent System

The chemiluminescent system is configured to produce light upon contact with an aqueous system. The aqueous system initiates the chemiluminescence reaction in order to produce light. As used herein, the term "aqueous system" refers to water or water-containing compositions. In the context of this disclosure, such water-containing compositions are generally in the form of body fluid, such as urine, menses, fecal matter, and so forth. The occurrence of the release of bodily fluid (or the fluid itself) is referred to herein as an "insult," or "liquid insult" or "fluid insult." Accordingly, the chemiluminescent systems of the present disclosure produce light upon insult of an article in which the system is incorporated.

In being configured to produce light upon contact with an aqueous system, the chemiluminescent system includes at least one compound or material that luminesces when contacted with an aqueous system. In one embodiment, water initiates the chemiluminescence.

In one embodiment, the chemiluminescent system includes two or more materials that luminesce when contacted with an aqueous system. In this embodiment, there are two or more materials that together do not luminesce without the presence of the aqueous system.

Representative chemiluminescent systems that include two or more materials include bioluminescent systems, such as a system that includes a luciferin and a luciferase.

Bioluminescence is light that is produced by a chemical reaction that occurs within the body or in the secretions of certain type of organisms. Bioluminescence involves the combination of two types of substances in a light-producing reaction: a luciferin and a luciferase. Luciferin is the compound that actually produces the light, for example, the luciferin can be coelenterazine. Luciferase is an enzyme that catalyzes the reaction. In some cases the luciferase is a protein known as a photoprotein, and the light making process requires a charged ion (e.g., a cation such as calcium) to activate the reaction. Photoprotein is a variant of luciferase in which factors required for light emission (including luciferin and oxygen) are bound together as one unit. Often, the bioluminescence process requires the presence of a substance such as oxygen or adenosine triphosphate (ATP) to initiate the oxidation reaction. The reaction rate for the luciferin is controlled by the luciferase or photoprotein. The luciferin-luciferase reaction can also create byproducts such as inactive oxyluciferin and water.

Luciferin and luciferase are generic names rather than specific materials. For example, the luciferin coelenterazine (natural form) is common in marine bioluminescence but variants can be chemically synthesized, and these various forms are collectively called luciferins. In another example, dinoflagellates (marine planktons) that obtain food through photosynthesis use a luciferin that resembles the chlorophyll structure.

The mechanism of light production through a chemical reaction differentiates bioluminescence from other optical phenomenon such as fluorescence or phosphorescence.

For example, fluorescent molecules do not emit their own light. They need an external photon source to excite the electrons to a higher energy state. On relaxation from the high energy state to their natural ground state, they release their acquired energy as a light source, but usually at a longer wavelength. Since the excitation and relaxation occurs simultaneously, fluorescent light is seen only when illuminated (excited).

The term phosphorescence technically refers to a special case of optically excited light emission where the relaxation from the excited state to ground state, unlike the fluorescence, is not immediate, and the photon emission persists for seconds to minutes after the original excitation.

The technical distinction between bioluminescence and fluorescence is sometimes blurred in a practical context but technically they are two distinct phenomena. In most cases, a bioluminescent can be an autofluorescent but the reverse is not true for a fluorescent; the latter still requires photon for excitation to emit light. In some cases a bioluminescent cnidarians or crustaceans or fish can contain a fluorescent protein like Green Fluorescent Protein (GFP) and the light emitted from the bioluminescent would act as photons to excite the GFP. The GFP in turn under relaxed state would emit a light of different wave length (most probably of higher wave length) than the wavelength of the bioluminescent light that it has received as photon. In this example, the GFP may be excited by a blue light emitted by the bioluminescent (wavelength about 470 nm, or 470 nm) but in turn would emit a green light under its relaxed state (wavelength of about 510 nm to about 520 nm, or 510 nm to 520 nm).

Bioluminescent systems can be incorporated into fluff pulp compositions, fiber matrices, or absorbent articles in any manner that produces the desired chemiluminescence.

In one embodiment, the fluff pulp composition or absorbent product comprises a luciferin selected from the group consisting of coelenterazine, dinoflagellate luciferin, bacterial luciferin, fungal luciferin, firefly luciferin, and vargulin. With regard to coelenterazine, there are many variants, any of which can be used in the fluff pulp composition.

Certain embodiments of coelenterazine consistent with this disclosure comprise one or more of native coelenterazine, methyl coelenterazine, coelenterazine 400a (2-2'(4-dehydroxy)) coelenterazine, coelenterazine e, coelenterazine f, coelenterazine h, coelenterazine coelenterazine n, coelenterazine cp, coelenterazine ip, coelenterazine fcp, and coelenterazine hep. As a further example, the coelenterazine may be one or more of native coelenterazine, coelenterazine 400a, methyl coelenterazine, coelenterazine f, coelenterazine cp, coelenterazine fcp, and coelenterazine hep. As yet a further example, the coelenterazine may be one or more of coelenterazine 400a, methyl coelenterazine and coelenterazine fcp. As yet a further example, the coelenterazine may be one or more of coelenterazine 400a, methyl coelenterazine, and coelenterazine hep. In yet another example, the coelenterazine may be may be one or more of coelenterazine 400a and coelenterazine hep.

In one embodiment, the luciferin has a concentration of 0.0005% to 0.002%, by weight of the fluff pulp. In one embodiment, the luciferin has a concentration of 0.0005% to 0.0015%, by weight of the fluff pulp. In one embodiment, the luciferin has a concentration of 0.0005% to 0.001%, by weight of the fluff pulp.

In some embodiments, the luciferin can be incorporated in any component of an absorbent article. For example, the luciferin (e.g., coelenterazine, or a coelenterazine salt of the present disclosure) can be incorporated into an absorbent article in an amount of from about 0.01 to about 100 mg (e.g., from about 0.01 to about 75 mg, from about 0.01 to about 50 mg, from about 0.01 to about 25 mg, from about 0.01 to about 10 mg, or from about 0.01 to about 5 mg), or 0.01 to 100 mg (e.g., from 0.01 to 75 mg, from 0.01 to 50 mg, from 0.01 to 25 mg, from 0.01 to 10 mg, or from 0.01 to 5 mg).

In one embodiment, the fluff pulp composition or absorbent product comprises luciferase selected from the group consisting of Gaussia luciferase (Gluc), Renilla luciferase (RLuc), dinoflagellate luciferase, firefly luciferase, fungal luciferase, bacterial luciferase, and vargula luciferase. Certain embodiments of the luciferase consistent with this disclosure comprise one or more of Gaussia luciferase, Renilla luciferase, dinoflagellate luciferase, and firefly luciferase. As a further example, the luciferase may be one or more of Gaussia luciferase, Renilla luciferase, dinoflagellate luciferase, and firefly luciferase. In yet a further example, the luciferase may be one or more of Gaussia luciferase and Renilla luciferase.

In one embodiment, the luciferase has a concentration of about 0.005% to about 0.04% (e.g., 0.005% to 0.04%) by weight of the fluff pulp. In one embodiment, the luciferase has a concentration of about 0.005% to about 0.02% (e.g., 0.005% to 0.02%) by weight of the fluff pulp. In one embodiment, the luciferase has a concentration of about 0.005% to about 0.01% (e.g., 0.005% to 0.01%) by weight of the fluff pulp.

In some embodiments, the luciferase can be incorporated in any component of an absorbent article. For example, the luciferase (e.g., GLuc) can be incorporated into an absorbent article in an amount of from about 0.2 mg to about 40 mg (e.g., from about 0.2 mg to about 30 mg, from about 0.2 mg to about 20 mg, from about 0.2 mg to about 15 mg, from about 0.2 mg to about 10 mg, from about 0.2 mg to about 5 mg, or from about 0.2 to about 2 mg); or from 0.2 mg to 40 mg (e.g., from 0.2 mg to 30 mg, from 0.2 mg to 20 mg, from 0.2 mg to 15 mg, from 0.2 mg to 10 mg, from 0.2 mg to 5 mg, or from 0.2 to 2 mg).

In one embodiment, the chemiluminescent system comprises coelenterazine as the luciferin and Gaussia or Renilla luciferase.

Representative luciferins include those of the coelenterazine family. Coelenterazine in its native form as well as its analogs have different luminescent characteristics due to variation in their structural moieties. Given structural variations within the coelenterazine family, some are good substrates for certain luciferases, whereas some are not. Below is a brief description of native coelenterazine and representative analogs.

Coelenterazine (native form) is a luminescent enzyme substrate for Renilla (reniformis) luciferase (Rluc). Renilla luciferase/coelenterazine has also been used as the bioluminescence donor in bioluminescence resonance transfer (BRET) studies.

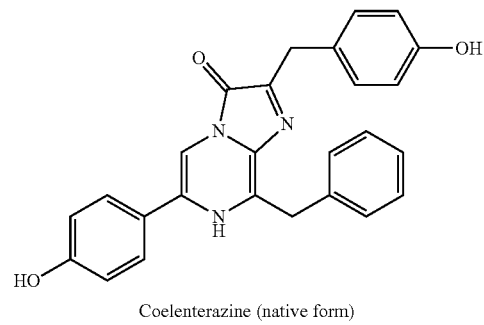 [SMILES: O=c1c(Cc2ccc(O)cc2)nc2c(Cc3ccccc3)[nH]c(-c3ccc(O)cc3)cn1-2]

Coelenterazine (native form)

Coelenterazine 400a is a derivative of coelenterazine and is a good substrate for Renilla luciferase, but does not oxidize well with Gaussia luciferase (Gluc). It is the preferred substrate for BRET (bioluminescence resonance energy transfer) because its emission maximum of about 400 nm (e.g., 400 nm) has minimal interference with the GFP emission.

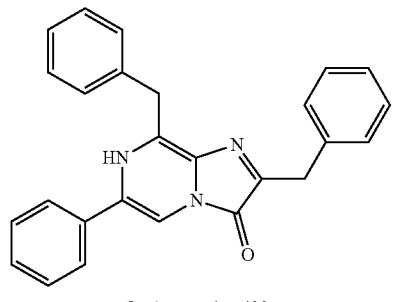

Coelenterazine 400a

Fluorescence resonance energy transfer (FRET), BRET, resonance energy transfer (RET), and electronic energy transfer (EET) are mechanisms describing energy transfer between two light-sensitive molecules (chromophores) and can define the interference of a luminescent chemical with another luminescent chemical's energy transfer. A donor chromophore, initially in its electronic excited state, may transfer energy to an acceptor chromophore through nonradiative dipole-dipole coupling. The efficiency of this energy transfer is inversely proportional to the sixth power of the distance between donor and acceptor, making FRET extremely sensitive to small changes in distance. Measurements of FRET efficiency can be used to determine if two fluorophores are within a certain distance of each other.

Such measurements are used as a research tool in fields including biology and chemistry.

Coelenterazine cp in a coelenterazine-aequorin complex generates luminescence intensity about 15 times (e.g., 15 times) higher than coelenterazine (native form).

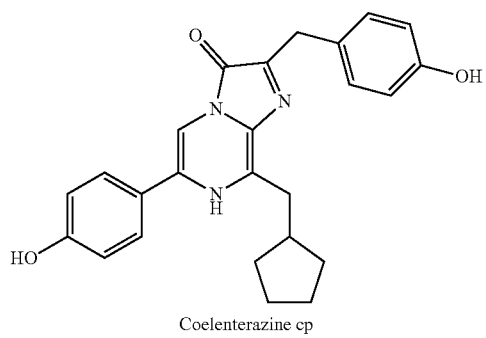 [SMILES: O=c1c(Cc2ccc(O)cc2)nc2c(CC3CCCC3)[nH]c(-c3ccc(O)cc3)cn1-2]

Coelenterazine cp

Coelenterazine f has about 20 times (e.g., 20 times) higher luminescence intensity (coelenterazine-apoaequorin complex) than the native form coelenterazine, while its emission maximum is about 8 nm (e.g., 8 nm) longer than that of the native form.

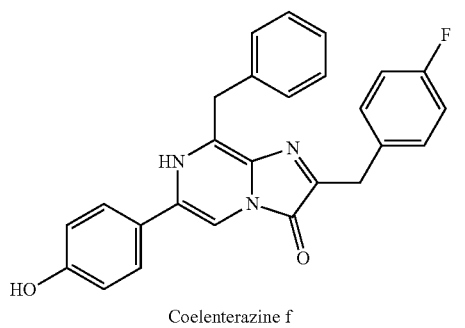 [SMILES: O=c1c(Cc2ccc(F)cc2)nc2c(Cc3ccccc3)[nH]c(-c3ccc(O)cc3)cn1-2]

Coelenterazine f

Coelenterazine fcp is an analog wherein the a-benzene structure in the coelenterazine moiety of coelenterazine f structure is replaced with a cyclic pentane (similar to coelenterazine cp). Coelenterazine fcp has luminescence intensity about 135 times (e.g., 135 times) greater than that of coelenterazine (native form).

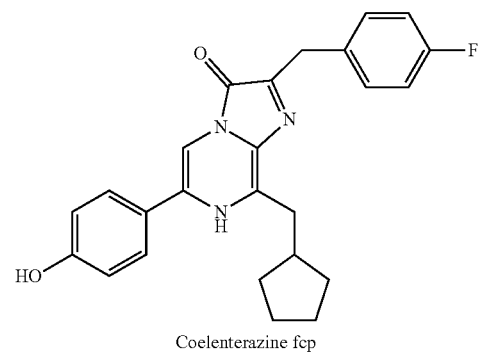 [SMILES: O=c1c(Cc2ccc(F)cc2)nc2c(CC3CCCC3)[nH]c(-c3ccc(O)cc3)cn1-2]

Coelenterazine fcp

Coelenterazine fcp complexes with aequorin to form a coelenterazine fcp-apoaequorin complex, and, as a substrate for aequorin, has a relative luminescence intensity of about 135 times (e.g., 135 times) that of native coelenterazine. However, coelenterazine fcp is a poor substrate for Renilla luciferase.

Other representative analogs of coelenterazine, as a substrate for Renilla Luciferase enzyme, are coelenterazine e, h and n. While these three analogs are good to excellent substrates for Renilla luciferase, they are poor substrates for apoaequorin.

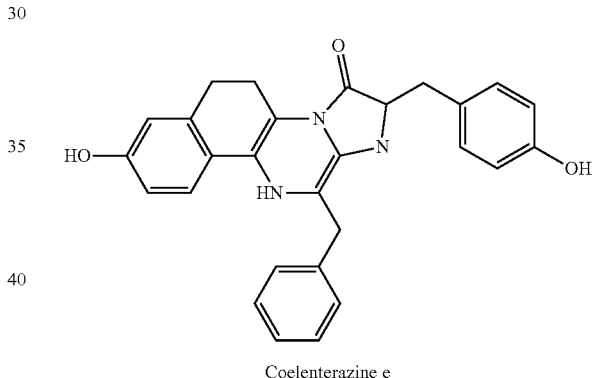

Coelenterazine e

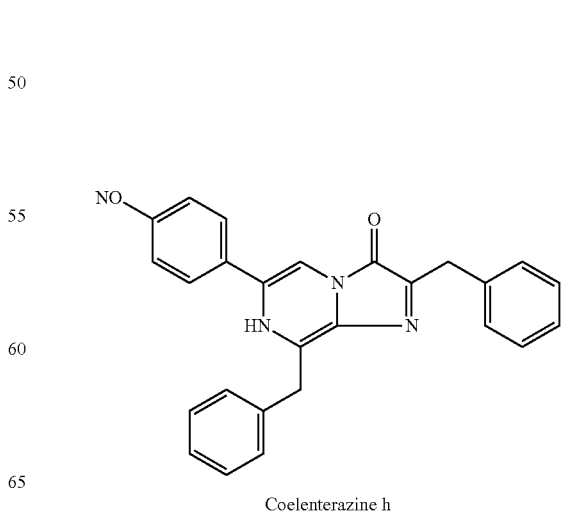

Coelenterazine h

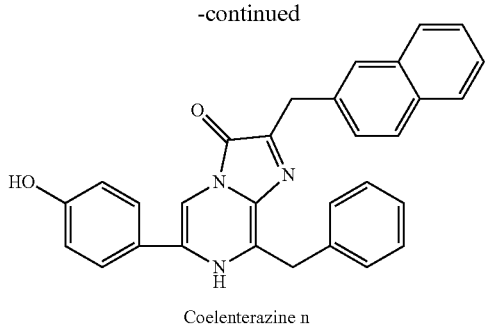

Coelenterazine n

The luminescent properties of coelenterazine analogs vary. For example, certain analogs emit less light (as measured as lumens) but with higher luminescent intensity (lumens/steradian). Table A lists the luminescent properties of coelenterazine (native form) and its analogs with Renato Luciferase. Luminescent intensity is reported as a % initial intensity. For example, an analog having an initial intensity of 900% is about 20 times (e.g., 20 times) intense as compared to the native coelenterazine with an initial intensity of about 45% (e.g., 45%).

TABLE A

Luminescent Properties of Selected Coelenterazine Analogs with *Renilla* Luciferase

| Analog | Aem (nm) | Total Light (%) | Initial Intensity (%) |
|---|---|---|---|
| native | 475 | 100 | 45 |
| e | 418, 475 | 137 | 900 |
| f | 473 | 28 | 45 |
| h | 475 | 41 | 135 |
| n | 475 | 47 | 900 |
| cp | 470 | 23 | 135 |

Light is produced by the chemiluminescent system. The light is visually detectable by a caregiver in the dark and through clothing, and as such the light has a wavelength, intensity, and duration sufficient to provide the necessary indication. These spectral characteristics of the chemiluminescent system can be tailored based on the chemiluminescent compound or compounds. For example, in bioluminescent systems, the luciferin and luciferase can be selected to produce the desired light characteristics. Depending on the bioluminescent system used, different spectral characteristics can occur. In the presence of superoxide anions and/or peroxynitrile compounds, coelenterazine can also emit light independent of enzyme (luciferase) oxidation, a process known as autoluminescence.

The chemiluminescent system can be tailored to produce particular colors of light. As noted above in Table A, even within the coelenterazine family, the emission wavelength can range from about 400 nm (violet, e.g., 400 nm) to about 475 nm (blue with green tint, e.g., 475 nm).

With regard to duration, the duration of the light emitted may be controlled by the selection of the coelenterazine (luciferin), in native form versus its analogues, and the enzyme (Luciferase), for example Gaussia versus Renilla. The ratio and the concentration of luciferin and luciferase used may also modify the duration of light emission. To give an illustrative and non-limiting example, the luciferin analogue, coelenterazine e, has a total light of 130% and initial intensity of 900% over native coelenterazine. By judiciously selecting the concentration of coelenterazine e and Renilla luciferase, the duration of the light emitted can last as long as about 8 to about 10 hours (e.g., 8 to 10 hours).

In one embodiment, the light has a duration of about 0.5 to about 6 hours (e.g., 0.5 to 6 hours). In another embodiment, the light has a duration of about 1 to about 4 hours (e.g., 1 to 4 hours). In another embodiment, the light has a duration of about 2 to about 3 hours (e.g., 2 to 3 hours).

With regard to intensity, quantum efficiency of the chemiluminescence contributes to the intensity, depth, and hue of the color of the emission.

Quantum efficiency (QE) is the fraction of photon flux used to excite a luminescence chemical to elevate it to higher energy state. Quantum efficiency is one of the most important parameters used to evaluate the quality of a detector and is often called the "spectral response" to reflect its wavelength dependence. It is defined as the number of signal electrons created per incident photon. In some cases it can exceed 100% (i.e. when more than one electron is created per incident photon). If the spectral response exceeds 100%, then the intensity and depth of the color emitted is vivid, but depending on the status of the excited state of the primary electron, the duration of the emission will be determined (i.e., the higher the excited state, the more time it takes to return to the ground (normal) state).

Spectral responsivity is a similar measurement, but it has different units; the metric being the amperes or watts (i.e., how much current comes out of the device per incoming photon of a given energy and wavelength).

Both the quantum efficiency and the spectral responsivity are functions of the photons' wavelength. For example, in the case of the luciferin coelenterazine, between the native form and one of its analogs, coelenterazine e, the latter has not only high light intensity but emits 30% more light energy than the former, because the latter upon excitation by a given quanta (hv) of incident photon generates two electrons and the primary electron at wavelength 475 has the same emission intensity as native coelenterazine but with lumen intensity about 20 times (e.g., 20 times) greater than that of the native product. Accordingly, the light emitted by the excited coelenterazine analog would be twenty times brighter than the native form but with a total light energy of about 130% (e.g., 130%) will last longer than the native form.

The wavelength determines the color of the emitted light.

In one embodiment, the fluff pulp composition includes a luciferin and a luciferase. Such a fluff pulp has both elements of the chemiluminescent system required to luminesce upon contact with an aqueous system. However, in another embodiment, the fluff pulp composition includes at least one component selected from a luciferin and a luciferase. In such an embodiment, the fluff pulp composition may include only one of a luciferin and a luciferase. Such a fluff pulp composition may be incorporated into an absorbent article such that the other one of the luciferin and the luciferase may be disposed in a top sheet or other layer of the absorbent article, such that the two components are combined only when carried by a liquid insult (e.g., water from an aqueous system passing through the top sheet into the fluff pulp composition). In one embodiment the fluff pulp composition comprises a luciferin but not a luciferase. In one embodiment the fluff pulp composition comprises a luciferase but not a luciferin.

Fluff Pulp

The fluff pulp of the fluff pulp composition can be formed from any pulp. In one embodiment, the fluff pulp is derived from a lignocellulosic fiber. In one embodiment, the fluff pulp is derived from a lignocellulosic fiber derived from wood. In one embodiment, the fluff pulp is derived from a lignocellulosic fiber derived from wood by chemical, mechanical, chemimechanical, or thermomechanical means. In one embodiment, the fluff pulp is derived from a cellulosic fiber derived from wood by chemical pulping. In one embodiment, the fluff pulp is derived from a cellulosic fiber derived from chemical pulping of wood either by alcohol pulping, organo-solve pulping, acid sulfite pulping, alkaline sulfite pulping, neutral sulfite pulping, alkaline peroxide pulping, Kraft pulping, Kraft-AQ pulping, polysulfide pulping, or polysulfide-AQ pulping.

In one embodiment, the fluff pulp is derived from a cellulosic fiber derived from chemical pulping of wood by further removing lignin from the said pulp either by alcohol pulping, organo-solve pulping, acid sulfite pulping, alkaline sulfite pulping, neutral sulfite pulping, alkaline peroxide pulping, Kraft pulping, Kraft-AQ pulping, polysulfide pulping, or polysulfide-AQ pulping for the preparation of absorbent articles (fluff pulp). In one embodiment, the fluff pulp is derived from a cellulosic fluff pulp derived from Kraft pulping. In one embodiment, the fluff pulp is derived from a cellulosic bleached fluff pulp derived from Kraft pulping. In one embodiment, the fluff pulp is derived from a cellulosic bleached fluff pulp derived from Kraft pulping of softwoods. In one embodiment, the fluff pulp is derived from a cellulosic bleached fluff pulp derived from Kraft pulping of Southern softwoods. In one embodiment, the fluff pulp is derived from a cellulosic bleached fluff pulp derived from Kraft pulping of Southern pine. In one embodiment, the fluff pulp is derived from a Southern softwood. In one embodiment, the fluff pulp is derived from Southern pine.

The fluff pulp composition can be produced from pulp in any form, such as a wet-laid sheet which is dried to achieve a moisture content ranging from about 6% to about 11% (e.g., 6% to 11%).

In another aspect, methods of preparing the fluff pulp composition are provided. The fluff pulp composition is prepared by incorporating at least one component of the chemiluminescent system into the fluff pulp.

This can be accomplished using various methods that allow the fluff pulp to be treated with one or more components of the chemiluminescent system. One challenge in the chemical treatment of fluff pulp is to maintain the chemicals in a state in which the intended chemiluminescent reaction is not prematurely triggered, for example, before the treated fluff pulp is incorporated into an absorbent article that is then subjected to a liquid insult. For a wet end application, the chemicals typically cannot be comingled with water and be applied together. Accordingly, in an illustrative example, either the luciferase or luciferin may be microencapsulated and introduced during the wet-laying process, with the non-encapsulated component applied to the sheet in a non-aqueous environment by standard methods such as coating, dipping, spraying, or printing (or combination thereof), prior to the air-laid operation during absorbent article manufacture. In another illustrative example, a two sheet system, one containing luciferase and the other containing luciferin, may be made and processed further before the air-laid operation during absorbent article manufacture. In yet other examples, one of the chemicals maybe added during the wet-laying process and the other during the subsequent processing of the pulp; or the two components may be added to the pulp during or prior to the air-laid process, such as by rinsing and/or spraying the pulp in fluffed form with non-aqueous solutions of one or both the respective components.

Absorbent Articles

In one embodiment, the fluff pulp composition; the isolated composition including the coelenterazine, or salt thereof; and/or the coelenterazine, or salt thereof, can be incorporated into absorbent articles. Representative absorbent articles include child diapers, adult diapers, adult incontinence products, feminine hygiene products, absorbent underpads, and wound care dressing articles. For example, the fluff pulp composition and/or the coelenterazine, or salt thereof, can be incorporated into one or more absorbent layers or portions of an absorbent article.

In another aspect, an absorbent article is provided. In one embodiment, the absorbent article includes a top sheet that is liquid permeable, a back sheet that is liquid impermeable, fluff pulp disposed between the top sheet and the back sheet and/or a fluffless or near fluffless non-woven fabric matrix disposed between the top sheet and the back sheet, and a chemiluminescent system configured to produce light upon contact with an aqueous system.

The chemiluminescent system (e.g., a luciferin such as coelenterazine, or a salt thereof of the present disclosure, and a luciferase) of the absorbent article is as described herein. However, the chemiluminescent system need not be disposed, in whole or in part, within the fluff pulp. As discussed above, structural and fluid distribution functions may be provided, in some configurations, by synthetic fibers, leading to the development of absorbent cores containing both fluff pulp fibers and synthetic fibers, and even "fluff-less" absorbent cores containing no fluff pulp fibers. In some embodiments, the chemiluminescent system, or parts of the chemiluminescent system, can be independently integrated in the liquid permeable top sheet, the liquid impermeable back sheet, the SAP, or another structure in the absorbent article.

In one embodiment, the chemiluminescent system comprises a luciferin and a luciferase. In one embodiment the luciferin and the luciferase are both disposed within the fluff pulp. In another embodiment, one of the luciferin and the luciferase is disposed within the fluff pulp and the other is disposed in a different layer (e.g., top sheet or ADL) of the absorbent product such that the two components are combined only when at least one of the two components is carried by a liquid insult (e.g., passing through the top sheet or ADL into the fluff pulp composition). In one embodiment the fluff pulp comprises a luciferin but not a luciferase. In one embodiment the fluff pulp comprises a luciferase but not a luciferin.

In yet another embodiment, at least one component of the chemiluminescent system is disposed on (for example, printed onto) the inner surface of the backsheet.

In one embodiment, one of the luciferin and the luciferase is disposed within the fluff pulp and the other is associated with the top sheet or another structure within an article, and configured to travel into the fluff pulp upon exposure to a liquid insult.

In one embodiment, the absorbent article further comprises a pH buffer, as disclosed herein. In one embodiment, the pH buffer is disposed within the fluff pulp. As discussed above, structural and fluid distribution functions may be provided, in some configurations, by synthetic fibers, leading to the development of absorbent cores containing both fluff pulp fibers and synthetic fibers, and even "fluff-less" absorbent cores containing no fluff pulp fibers. In some embodiments, the chemiluminescent system, or parts of the chemiluminescent system, can be independently integrated in the liquid permeable top sheet, the liquid impermeable back sheet, the SAP, or another structure in the absorbent article.

In one embodiment, the absorbent article further comprises a photoluminescent compound, as disclosed herein. In one embodiment, the photoluminescent compound is disposed within the fluff pulp.

In one embodiment, the absorbent article further comprises a photoluminescent compound and a pH buffer, as disclosed herein. In one embodiment, the photoluminescent compound and the pH buffer are disposed within the fluff pulp.

In one embodiment, the pH buffer, the photoluminescent compound, the luciferin, and the luciferase are disposed within the fluff pulp.

In one embodiment, at least one of the pH buffer, the photoluminescent compound, the luciferin, and the luciferase are not disposed within the fluff pulp. In some embodiments, at least one of the pH buffer, the photoluminescent compound, the luciferin, and the luciferase can be independently incorporated into synthetic fibers, "fluff-less" absorbent cores containing no fluff pulp fibers, in the liquid permeable top sheet, the liquid impermeable back sheet, and/or the SAP of the absorbent article. In some embodiments, the pH buffer, the photoluminescent compound, the luciferin, and/or the luciferase can migrate to an absorbent core from a different structure of the article. In some embodiments, the pH buffer, the photoluminescent compound, the luciferin, and/or the luciferase can migrate from an absorbent core to a different structure of the article.

In one embodiment, the absorbent article further includes a superabsorbent polymer (SAP), such as incorporated in the absorbent core. In such an embodiment, at least one component of the chemiluminescent system may be disposed in the SAP, such that the chemiluminescence is generated upon the fluid from an insult traveling to the absorbent core.

In one embodiment the chemiluminescent system is contained entirely within an absorbent core of the absorbent article. As the absorbent core is almost always a multi-component system there exist more than one approach to incorporate the chemiluminescent system into the absorbent core. For instance the fluff pulp fibers could be the carrier of the chemiluminescent system. Alternatively, the chemiluminescent system could be contained within superabsorbent particles incorporated into the absorbent article. In some embodiments, the absorbent core can include cellulose fibers, cellulose fiber derivatives (rayon, lyocell, etc.), non-woven cellulose fibers and/or cellulose fiber derivatives, or non-cellulose fibers, or any combination thereof.

Furthermore, if only a portion of the SAP particles or fibers contained the chemiluminescent system chemistry, a desired pattern, such as an aesthetically pleasing pattern, can be achieved.

The chemiluminescent system can be added to the fluff pulp fibers at the time of absorbent article manufacture or during an upstream process entirely separated from final product assembly. As noted above, for example, the chemiluminescent system may be sprayed onto or otherwise incorporated into a fluff pulp sheet prior to hammermilling.

In another aspect, methods of manufacturing absorbent articles are also provided.

Absorbent articles are manufactured according to general techniques known to those of skill in the art that allow the incorporation of the chemiluminescent system to be incorporated into the absorbent article in the manner disclosed herein.

The following examples are intended to be illustrative, not limiting. Example 1 describes the synthesis of coelenterazine on a 1 Kg scale. Example 2 describes the synthesis of coelenterazine on a 25 gram scale. Example 3 describes the synthesis of coelenterazine on a 100 gram scale. Example 4 describes the synthesis of coelenterazine on a multi-kilogram scale.

EXAMPLES

Example 1. Synthesis of Coelenterazine (1 Kilogram)

Synthesis of 3-benzylpyrazin-2-amine (25)

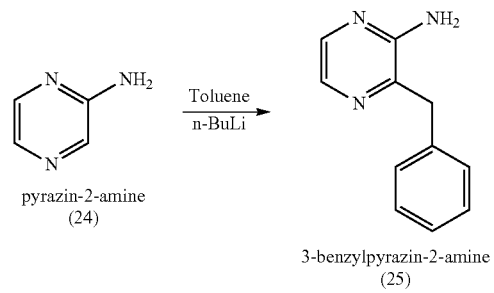

pyrazin-2-amine
(24)

3-benzylpyrazin-2-amine
(25)

A 100 L round bottom flask was charged with 10 L of toluene followed by 10 L tetramethylethylenediamine (TMEDA). The mixture was cooled at 0-5° C. with ice water. To this stirred mixture was added 20 L of n-butyl lithium (2.5 M in n-hexane) solution at 0° C. to 8° C. dropwise over 1-1½ hrs under nitrogen. After the complete addition, the reaction mixture was allowed to come to room temperature (22° C.). After 20 minutes at room temperature, the mixture slowly heated up to 60° C. (During this time butane gas was released). The reaction mixture was maintained at 60° C.±1° C. for 30 minutes and then allowed to cool to room temperature.

Meanwhile another 30 L flask was charged with tetrahydrofuran (THF) (15 L) and pyrazin-2-amine (24) (also named 2-amino pyrazine (24)) (1 Kg). The mixture was stirred at 25-35° C. for 20 minutes. This solution was added over 1-1.5 hrs to the above benzyl lithium solution using addition flask. The mixture was stirred at room temperature for 1 hr. Water (16 L) was added to the reaction mixture at 20° C. dropwise while maintaining the temperature between 20-25° C. The mixture was stirred at room temperature for 30 min, and then the organic layer was separated, and distilled off excess solvents. The residue was treated with toluene (8 L) and water (3 L) and stirred for 10 minutes. The organic layer was separated, and solvent was distilled off at reduced pressure to yield the desired 3-benzylpyrazin-2-amine (25) in 60%-65% yield. Purity 94%-95%.

Synthesis of 3-benzyl-5-bromopyrazin-2-amine (2)

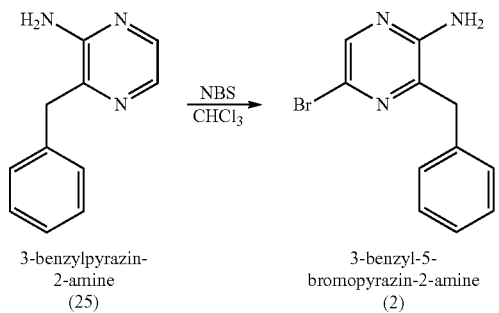

3-benzylpyrazin-
2-amine
(25)

3-benzyl-5-
bromopyrazin-2-amine
(2)

A 20 L round bottom flask was charged with chloroform (6 L) and 3-benzylpyrazin-2-amine (25) (also named 2-amino-3-benzyl pyrazine, (25)) (1 Kg), and stirred the mixture at room temperature (22° C.). N-bromosuccinimide (NBS) (800 grams) was added slowly over 1 to 1.5 hrs. After the complete addition, the mixture was stirred for 30 minutes. Water (2 L) was added and stirred for 10 minutes. The organic layer was separated and washed with water (2×1 L). The chloroform layer was concentrated under reduced pressure and the oily residue was dried under vacuum. Yield 77%-85%. Purity 93%-95%.

Synthesis of 3-benzyl-5-(4-methoxyphenyl)pyrazin-2-amine (5)

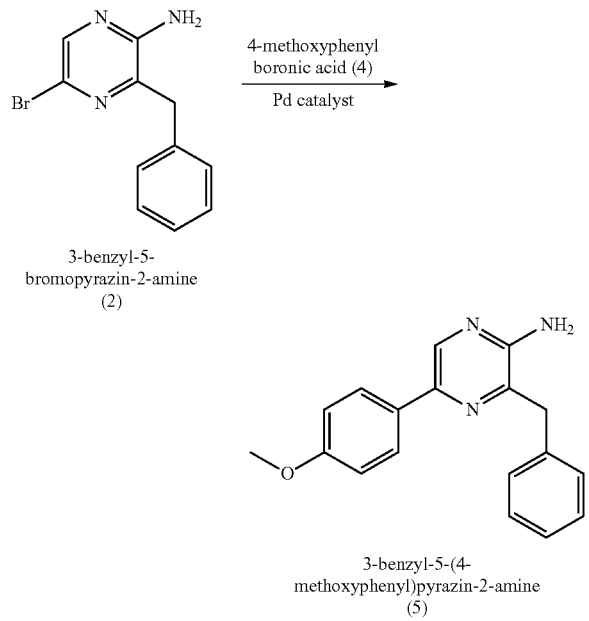

A 50 L flask was charged with 1,4-dioxane (30 L) and 3-benzyl-5-bromopyrazin-2-amine (2) (1 Kg) at room temperature. Potassium carbonate (1.6 Kg) was added followed by water (5 L). The reaction mixture was stirred for 10 minutes. 4-methoxyphenyl boronic acid (4) (600 grams) was added followed by palladium catalyst (300 grams). The reaction mixture was slowly heated up to 82° C. and stirred at 80-82° C. for 5 hrs. The mixture was cooled to room temperature and transferred to 100 L round bottomed flask, and charged with ethyl acetate (15 L) and water (15 L) at room temperature and stirred for 20 minutes. The organic layer was separated and concentrated under reduced pressure to yield the desired product. Yield 85%-90%. Purity 92%-95%.

Synthesis of 4-(5-amino-6-benzyl-pyrazin-2-yl)phenol (7)

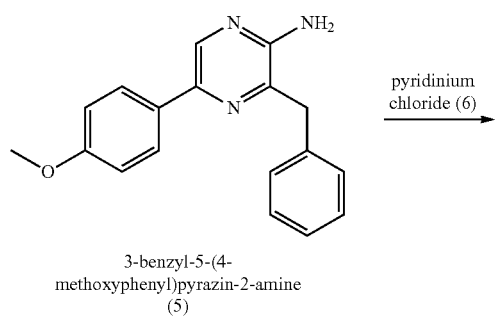

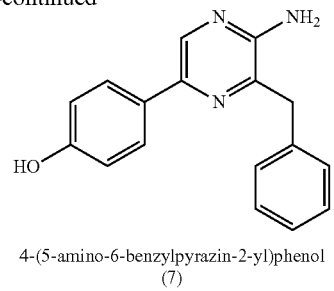

4-(5-amino-6-benzylpyrazin-2-yl)phenol (7)

A 30 L round bottom flask was charged with 3-benzyl-5-(4-methoxyphenyl)pyrazin-2-amine (5) (1 Kg), and pyridine hydrochloride (6) (6.5 Kg). The reaction mixture was slowly heated to 200° C. in an oil bath. The reaction temperature was maintained at 200-210° C. for 30 min. The mixture was cooled to 40° C. and charged with water (13 L) and ethyl acetate (15 L) at 35-40° C. The reaction mixture was stirred for 20 minutes. The ethyl acetate layer was separated and the aqueous layer was re-extracted with ethyl acetate (3 L×2). The combined ethyl acetate extracts were concentrated under reduced pressure. The residue was taken up with 2 L of ethyl acetate and refluxed. The solution was slowly cooled to 10-15° C. and the solid formed was filtered to yield the desired product. Yield 90%-95%. Purity 90%.

Alternatively, instead of using pyridinium chloride, a 30 L round bottom flask was charged with 3-benzyl-5-(4-methoxyphenyl)pyrazin-2-amine (1 Kg), NaH (1 Kg), DMF (20 L) and ethanethiol (2 Kg). The reaction mixture was slowly heated to 100° C. in an oil bath. The reaction temperature was maintained at 100-110° C. for 30 min. The mixture was cooled to 40° C. and charged with water (13 L) and ethyl acetate (15 L) at 35-40° C. The reaction mixture was stirred for 20 minutes. The ethyl acetate layer was separated, and the aqueous layer was re-extracted with ethyl acetate (3 L×2). The combined ethyl acetate extracts were concentrated under reduced pressure. The residue was taken up with 2 L of ethyl acetate and refluxed. The solution was slowly cooled to 10-15° C. and the solid formed was filtered to yield the desired product. Yield 90%-95%. Purity 90%.

In both scenarios, the product can be optionally purified by charging 1 Kg of the product and 5 L 1,4-dioxane at room temperature into a 10 L round bottom flask, adding sodium hydroxide solution (250 g sodium hydroxide in 1 L water) to the solution, charging the flask with 100 g of charcoal and 100 g silica gel at room temperature, stirring the mixture at room temperature for 20 mins, and filtering and washing the solids with 250 ml 1,4-dioxane. The filtrate was then transferred to another 20.0 L round bottom flask and 200 ml HCl slowly added to the reaction mixture to adjust the pH to 7 to 7.5 at room temperature, during which a solid precipitate was observed. The reaction mixture was then stirred at room temperature for 30 mins, filtered, and washed with 200 ml 1,4-dioxane. The isolated solid product was dried under vacuum, and in in the oven at 50-55° C. for 4 hrs. Yield 90%-95%. Purity 90%.

Synthesis of 4-(tert-butyldimethylsiloxy) benzyl alcohol (20b)

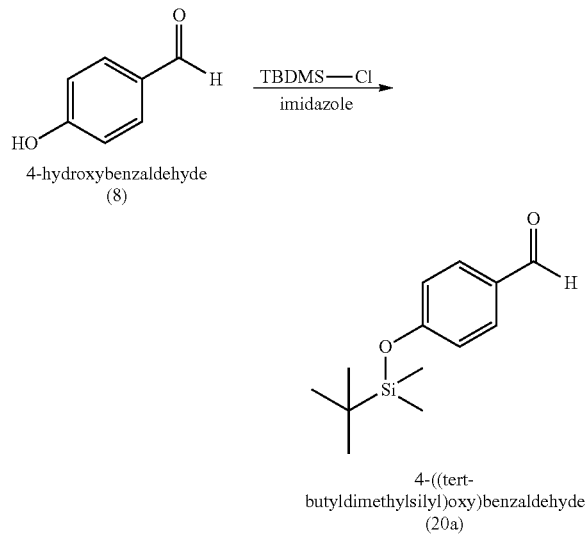

A 20 L round bottom flask was charged with dichloromethane (10 L), 4-hydroxy benzaldehyde (8) (1 Kg). N,N'-dimethylaminopyridine (50 grams) and imidazole (1.33 Kg). The reaction mixture was cooled to 20° C. and stirred. To this stirred mixture was added portion wise tert-butyldimethylsilyl chloride (TBDMS-Cl, 500 grams×3). After 1 hour, the reaction mixture was filtered, and concentrated under reduced pressure to get an oily product (20a).

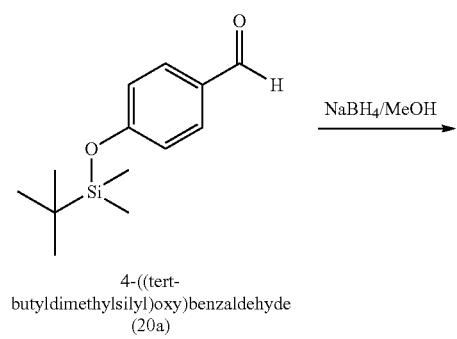

The above product (20a) was taken in a 10 L round bottom flask and dissolved in methanol (6 L). The reaction mixture was cooled to 10-15° C., and sodium borohydride (100 grams) was added with stirring. After 30 minutes the reaction pH was adjusted to 7.0 with acetic acid. After stirring for 20 minutes, methanol was distilled off to yield the desired 4-(tert-butyldimethylsiloxy) benzyl alcohol (20b). Yield 85%-90%, Purity 80%-85%.

Synthesis of 4-(tert-butyldimethylsiloxy) benzyl chloride (21)

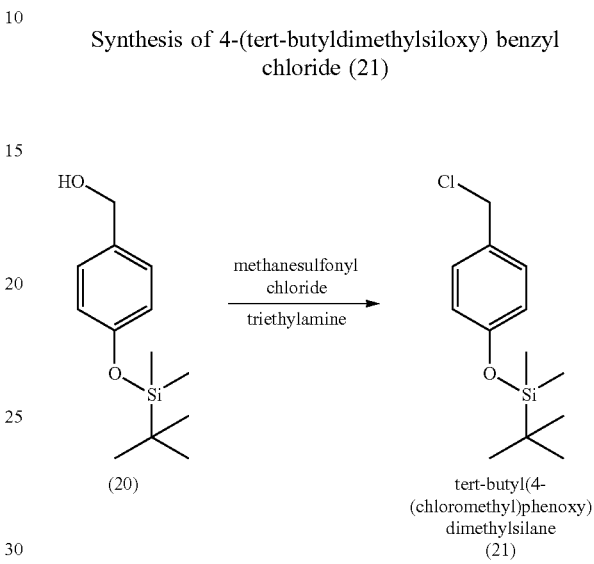

A 10 L round bottom flask was charged with 4-(tert-butyldimethylsiloxy)benzyl alcohol (20b) (1 Kg) and dichloromethane (6 L) followed by triethylamine (1.4 L). The reaction mixture was stirred for 30 minutes at room temperature. Methanesulfonyl chloride (600 mL) was added slowly at 30-35° C. in about 1-1.5 hours. After the completion of the reaction 30% aqueous sodium bicarbonate solution (400 ml) was added and stirred for 20 minutes. Dichloromethane layer was separated and washed with aqueous sodium chloride solution (2×500 ml). Dichloromethane was removed under reduced pressure. The residue was used for the next step without further purification.

Synthesis of 3-(4-((tert-butyldimethylsilyl)oxy)phenyl)-1,1-diethoxypropan-2-one (23)

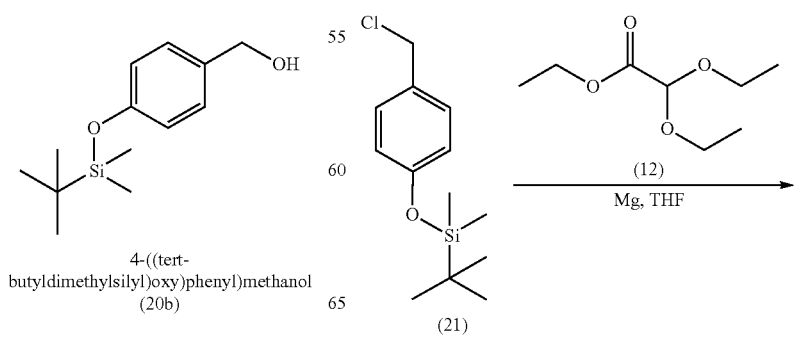

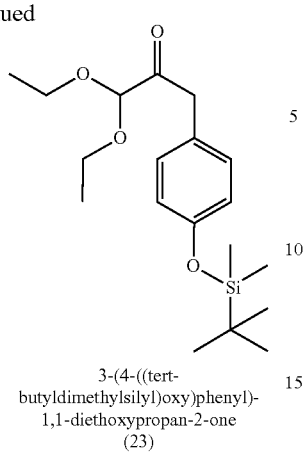

3-(4-((tert-butyldimethylsilyl)oxy)phenyl)-1,1-diethoxypropan-2-one
(23)

A 50 L round bottom flask was charged with magnesium turnings (1 Kg) and anhydrous tetrahydrofuran (3 L) followed by iodine (10 grams) and dibromoethane (50 ml). A solution of tert-butyl(4-(chloromethyl)phenoxy)dimethylsilane (21) (1.6 Kg) in anhydrous tetrahydrofuran (12 L) was added drop wise at 40-45° C. over a period of 4 hours. The reaction mixture was cooled to 35° C. Another 50 L round bottomed flask was charged with ethyl 2,2-diethoxyacetate (12) (2 Kg) and anhydrous tetrahydrofuran (10 L) and cooled to −35° C. The above prepared Grignard reaction mixture was added to this solution at −35° C. over a period of 1-1.5 hours. After the completion of the reaction, the reaction mixture was quenched with saturated aqueous ammonium chloride solution (1.2 Kg in water 7 L). The organic layer was separated, washed with saturated sodium chloride solution and the solvent was removed under reduced pressure. The oily residue was purified by column chromatography over silica gel with an eluant that includes triethylamine to yield 3-(4-((tert-butyldimethylsilyl)oxy)phenyl)-1,1-diethoxypropan-2-one (23) (0.48 Kg) Yield 20%-25%. Purity 90%.

Synthesis of coelenterazine 8-benzyl-2-(4-hydroxybenzyl)-6-(4-hydroxyphenyl)imidazo[1,2-α]pyrazin-3(7H)-one

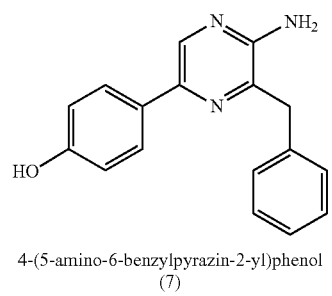

4-(5-amino-6-benzylpyrazin-2-yl)phenol
(7)

+

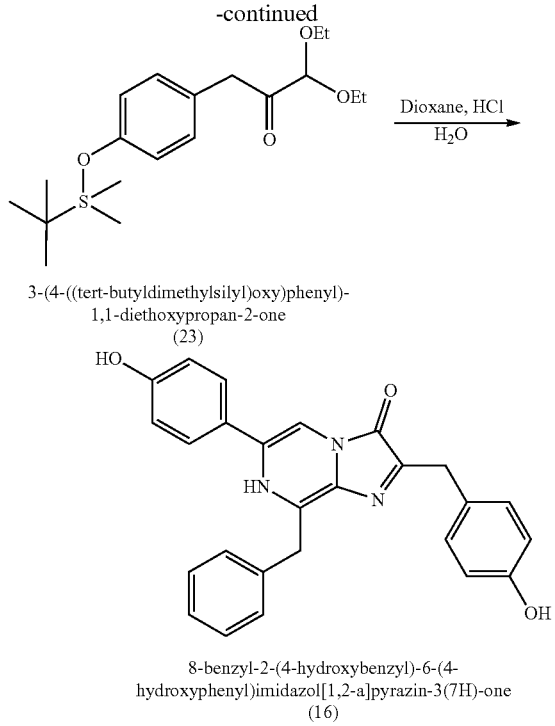

3-(4-((tert-butyldimethylsilyl)oxy)phenyl)-1,1-diethoxypropan-2-one
(23)

8-benzyl-2-(4-hydroxybenzyl)-6-(4-hydroxyphenyl)imidazo[1,2-a]pyrazin-3(7H)-one
(16)

A 30 L round bottom flask was charged with 4-(5-amino-6-benzyl-pyrazin-2-yl)phenol (7) (0.9 Kg) and 3-(4-((tert-butyldimethylsilyl)oxy)phenyl)-1,1-diethoxypropan-2-one (23) (1.4 Kg) followed by 1,4-dioxane (14 L). The reaction mixture was stirred at room temperature for 30 minutes. Concentrated hydrochloric acid (0.75 L) and water (0.75 L) was added and the reaction mixture was heated to 80-85° C. for 15 hours. The reaction mixture is cooled to 40° C. then activated carbon (100 g) and activated silica gel (100 g) are added and filtered. The solvent was removed under reduced pressure and the residue was precipitated by stirring with degassed ethyl acetate (2 L). Yield 60%-65%. Purity 60%-63%.

Example 2. Synthesis of Coelenterazine (16)

3-Benzyl-5-bromopyrazin-2-amine (2)

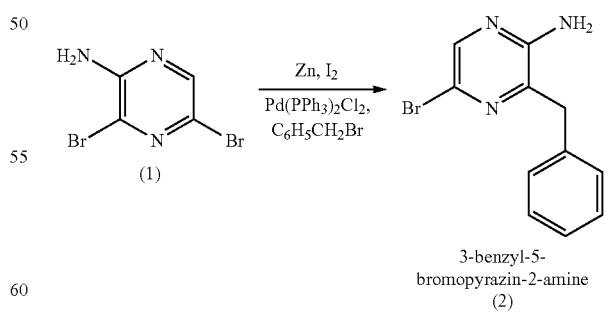

3-benzyl-5-bromopyrazin-2-amine
(2)

Zn dust and 30-mesh granular zinc (1:1, 16.05/16.05 g, 491.2 mmol, 3.5 equiv) and $I_2$ (6.23 g, 5% mol of Zn) were added to a dry 1 L 2-necked round-bottom flask under an argon atmosphere. N,N-dimethylacetamide (125 mL, freshly distilled over $CaH_2$) was added. The mixture was stirred at room temperature until the brown color of the 12 disappeared. Benzyl bromide (61.04 g, 356.9 mmol, 2.5 equiv) was added dropwise, and the mixture was stirred at 80° C. for 4 h. The mixture was cooled to room temperature and a suspension of 3,5-dibromo-2-aminopyrazine (1) (36.0 g, 140.3 mmol, 1 equiv) and PdCl$_2$ (PPh3)$_2$ (5.04 g, 0.712 mmol, 5% of pyrazine) in N, N-dimethylacetamide (150 mL) was added. The mixture was stirred continuously under an argon atmosphere for 1 day. The thin layer chromatography (TLC) (30% ethyl acetate/hexane) indicated that the reaction was complete. The reaction mixture was filtered through a short bed of celite. The filtrate was slowly poured into ice cold water (1 L), and extracted with EtOAc (3×200 mL). The combined organic layer was washed with water (200 mL), brine (200 mL), and dried over anhydrous MgSO$_4$. The organic layer was filtered and concentrated on a rotary evaporator under reduced pressure. The purification of the brown residue on a silica gel column chromatography eluting with hexane/EtOAc, 2:1 gave 3-benzyl-5-bromopyrazin-2-amine (2) as brown viscous oil, 28.0 g 74% yield. $^1$H NMR (CDCl$_3$): δ8.05 (s, 1H), 7.22-7.35 (m, 5H), 4.41 (s, 2H), 4.11 (s, 2H), 4.08 (s, 2H).

Palladium coupling reaction of p-methoxyphenyl boronic acid (4) with 3-benzyl-5-bromopyrazin-2-amine (2)

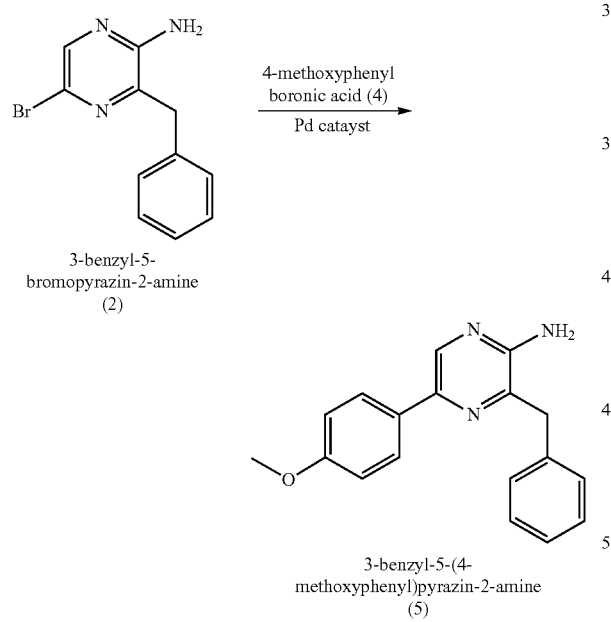

3-benzyl-5-bromopyrazin-2-amine (2)

4-methoxyphenyl boronic acid (4)
Pd catayst 3-benzyl-5-(4-methoxyphenyl)pyrazin-2-amine (5)

1,4-bis(diphenylphosphino)butane (2.71 g, 6.34 mmol) was added to a suspension of bis(benzonitrile)dichloropalladium (II) (2.03 g, 5.29 mmol) in toluene (210 mL) at room temperature under an argon atmosphere and stirred for 30 minutes. A solution of 3-benzyl-5-bromopyrazin-2-amine (2) (28.0 g, 106.0 mmol) in toluene (180 mL) was added to this mixture followed by 4-methoxyphenylboronic acid (20.94 g, 137.8 mmol), ethanol (42 mL), and 1.0 M aq. Na$_2$CO$_3$ (108 mL) were added sequentially at room temperature with stirring. The resulting mixture was heated to reflux for 4 h and then allowed to cool to room temperature. The mixture was diluted with 20% aq. NaCl solution (400 mL) and extracted with ethyl acetate (EtOAc, 3×300 mL). The combined organic layer was washed with water (200 mL), brine (200 mL), and dried over anhydrous MgSO$_4$. The organic layer was filtered and the ethyl acetate solution was treated with 2 N HCl (200 mL) to precipitate the product as its hydrochloride salt. A yellow precipitate formed immediately. The precipitated solid was isolated by filtration and dried under vacuum. The dried solid was washed with ethyl acetate (2×100 mL) to remove non polar impurities and subsequently dried under vacuum to yield 3-benzyl-5-(4-methoxyphenyl)pyrazin-2-amine hydrochloric acid salt (5), 24 g, 78% yield. $^1$H NMR (CDCl$_3$): δ8.05 (s, 1H), 7.22-7.35 (m, 5H), 4.41 (s, 2H), 4.11 (s, 2H), 4.08 (s, 2H). The LCMS analysis indicated that the product was around 99% pure.

De-methoxylation of methyl ether hydrochloride salt to phenol using pyridinium hydrochloride

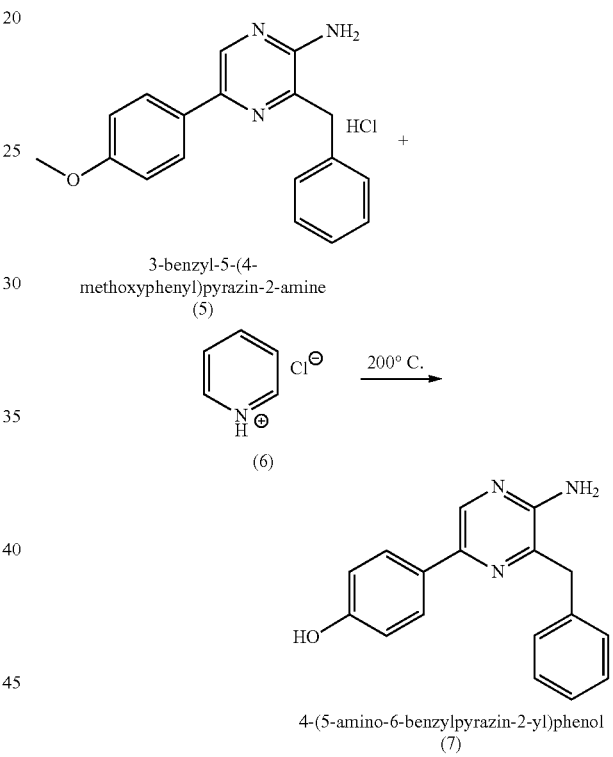

A mixture of 3-benzyl-5-(4-methoxyphenyl)pyrazin-2-amine hydrochloric acid salt (5) (20.0 g, 61.0 mmol) and pyridinium hydrochloride (6) (70.5 g, 0.61 mol) was heated at 200° C. for 2 h under an argon atmosphere. The dark brown colored mixture was cooled to room temperature, and a saturated sodium bicarbonate solution (750 ml) was added to the solid slowly followed by ethyl acetate (750 ml)). The organic layer was separated, and the aqueous layer was and extracted with EtOAc (3×200 mL). The combined ethyl acetate extracts were washed with water (2×300 mL), dried over anhydrous MgSO$_4$. The solution was filtered and concentrated on a rotary evaporator under reduced pressure. Purification of the brown reside on a silica gel column chromatography eluting with hexane-EtOAc, (3:7) gave 4-(5-amino-6-benzyl-pyrazin-2-yl)phenol (7), 14 g, 82% yield as light yellow solid., The solid was recrystallized from ethyl acetate/1% methanol to give a light brown powder. $^1$H NMR (DMSO-D6) δ9.36 (s, 1H), 8.17 (s, 1H), 7.60 (d, J=8.4

Hz, 2H), 7.13-7.22 (m, 5H), 6.68 (d, J=8.6 Hz, 2H), 6.09 (s, 2H), 3.94 (s, 2H). The LCMS analysis of the product indicated that it was around 99% pure.

4-Benzyloxybenzaldehyde (9)

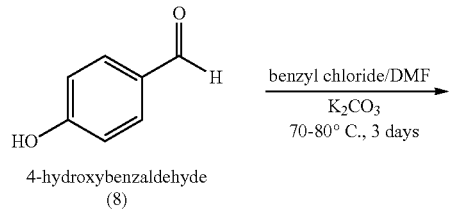

A mixture of 4-hydroxybenzaldehyde (8) (122.1 g, 1.0 mol), benzyl chloride (132.9 g, 1.05 mol), and anhydrous potassium carbonate (165.6 g, 1.2 mol) in N,N-dimethyl formamide (DMF, 1 L) was heated at 70-80° C. for 3 days with vigorous stirring. The progress of the reaction was monitored by TLC (20% ethyl acetate/hexane). The mixture was poured into ice cold water (4 L). The resulting solid was collected by filtration, washed with water (2×500 ml) and dried to yield the desired product as a white solid. Wt=210 g, and yield 96.3%.

4-Benzyloxybenzyl Alcohol (10)

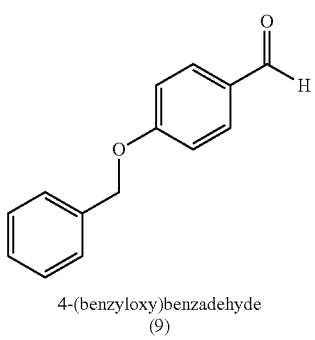

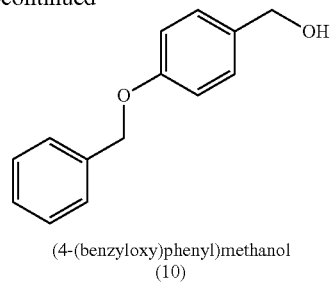

Sodium borohydride (40.0 g, 1.08 mol) was slowly added portion wise to a solution of 4-(benzyloxy)benzaldehyde (9) (218.0 g, 1.02 mmol) in a mixture of ethyl acetate/methanol (1:1, 1 L) at 0-5° C. over a period of 1 h. After the complete addition of sodium borohydride, the reaction mixture was slowly warmed to room temperature and stirred for 2 h. The progress of the reaction was monitored by TLC (20% ethyl acetate/hexane). The mixture was concentrated under reduced pressure, and the residue was partitioned between ethyl acetate (750 ml) and water (500 ml). The organic layer was separated. The aqueous layer was extracted with ethyl acetate (2×200 ml). The combined ethyl extracts were washed with water (500 ml) and dried over anhydrous MgSO₄, filtered, and concentrated under reduced pressure. The residue was recrystallized with 20% ethyl acetate/hexane to yield desired product. Wt=180.5 g, and yield 82.7%.

4-Benzyloxybenzyl Chloride (11)

a) Using thionyl chloride.

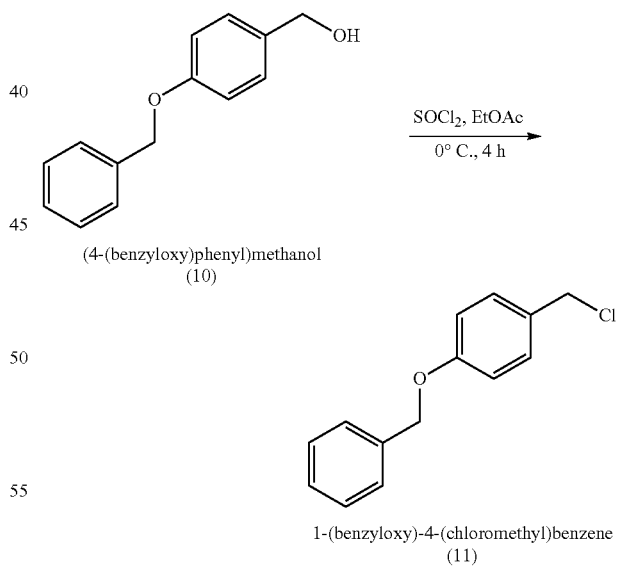

Thionyl chloride (101.2 g, 0.86 mol) was added drop wise to a cooled solution of (4-(benzyloxy)phenyl)methanol (10) (167.0 g, 0.78 mol) in ethyl acetate (600 ml) at 0° C. over 1 h. After the addition the reaction mixture was warmed to room temperature and stirred. The progress of the reaction was monitored by TLC, after 4 h reaction was complete. The reaction mixture was concentrated under reduced pressure (<50° C.). The resulting residue was recrystallized twice with hexane to yield the desire product as white solid. Wt=180 g, yield 77%. $^1$H NMR (400 MHz, CDCl$_3$): δ=4.57 (s, 2H), 5.08 (s, 2H), 6.96 (d, J=8.7 Hz, 2H), 7.32 (d, J=8.7 Hz, 2H), 7.43-7.37 (m, 5H).

b) Using cyanuric chloride:

Cyanuric chloride (1.0 g) was added to anhydrous N,N'-dimethylformamide (5 ml) at room temperature under an atmosphere of argon and stirred for 30 minutes. A white suspension was formed. A solution of (4-(benzyloxy)phenyl)methanol (1.0 g) in dichloromethane (30 ml) was added and stirred overnight. The precipitated solids were removed by filtration. The filtrate was diluted with hexane (50 ml) and washed with water, brine solution (20 ml each), dried over anhydrous magnesium sulfate. The solvent was removed under reduced pressure. The product was further purified by column chromatography over silica gel eluting with 5% ethyl acetate/hexane to give the product, Wt 650 mg Yield=59.5% c) Using methanesulfonyl chloride:

Methanesulfonyl chloride (13.74 g; 0.12 mol) was added dropwise to a solution of (4-(benzyloxy)phenyl)methanol (21.8 g; 0.10 mol) and triethylamine (15.15 g; 0.15 mol) in dichloromethane (250 ml) at 0° C. After the addition the reaction mixture was warmed to room temperature and stirred 12 h. The solvent was removed under reduced pressure. The residue was partitioned between ethyl acetate (200 ml) and water (100 ml). The ethyl acetate layer was separated, washed with water, brine solution (75 ml each), dried over anhydrous magnesium sulfate. The crude product obtained after the removal of the solvent was recrystallized from hexane to obtain 18 gram of the product. Wt=18 grams (Yield 70%).

3-[4-(Benzyloxy)phenyl]-1,1-diethoxypropan-2-one (13)

flushed, 500 mL two necked round-bottom flask. A solution of (11) (68.14 g, 0.29 mole) in THF (600 ml) was prepared and 25 ml of the solution was added at once and the flask was warmed to 40-50° C. with constant stirring until the Grignard reaction was initiated. After the initiation the remaining solution was added slowly at a rate so that the reaction mixture was warm to touch due to the heat of the reaction. After the addition mixture was stirred at room temperature for 30 min and then refluxed for 1 hour to complete the reaction. The pale yellow Grignard reagent was allowed to cool to room temperature and was then kept in an ice bath. A solution of ethyl diethoxy acetate (12) (51 g 0.29 mole,) in THF (200 mL) in a separate 1 liter round-bottom flask under an argon atmosphere and cooled to −78° C. The Grignard reagent was transferred to dropping funnel and was added drop wise into the cooled flask over 45 min. The mixture was then stirred for 6 h at −78° C. and warmed to −20° C. and stirred for 2 h. The reaction was quenched with saturated ammonium chloride solution (200 mL). The reaction mixture was extracted with ethyl acetate (500 mL). The ethyl acetate layer was washed with H$_2$O (3×200 mL), followed by saturated brine solution (2×200 mL). The organic layer was dried (anhydrous magnesium sulfate) and the solvent was removed by rotary evaporation under reduced pressure. The product was heated to 150° C. under reduced pressure to remove the impurities and unreacted starting materials. NMR of the product showed it to be sufficiently pure to carry out the next reaction. Wt=66.58 g Yield (70%)

$^1$H NMR (400 MHz, CDCl$_3$): δ=1.25 (t, J=7.3 Hz, 6H), 3.57 (m, 2H), 3.69 (m, 2H), 3.84 (s, 2H), 4.64 (s, 1H), 5.05 (s, 2H), 6.94 (d, J=8.4 Hz, 2H), 7.14 (d, J=8.4 Hz, 2H), 7.43-7.35 (m, 5H).

1,1-Diethoxy-3-(4-hydroxyphenyl)-2-propan-2-one) (14)

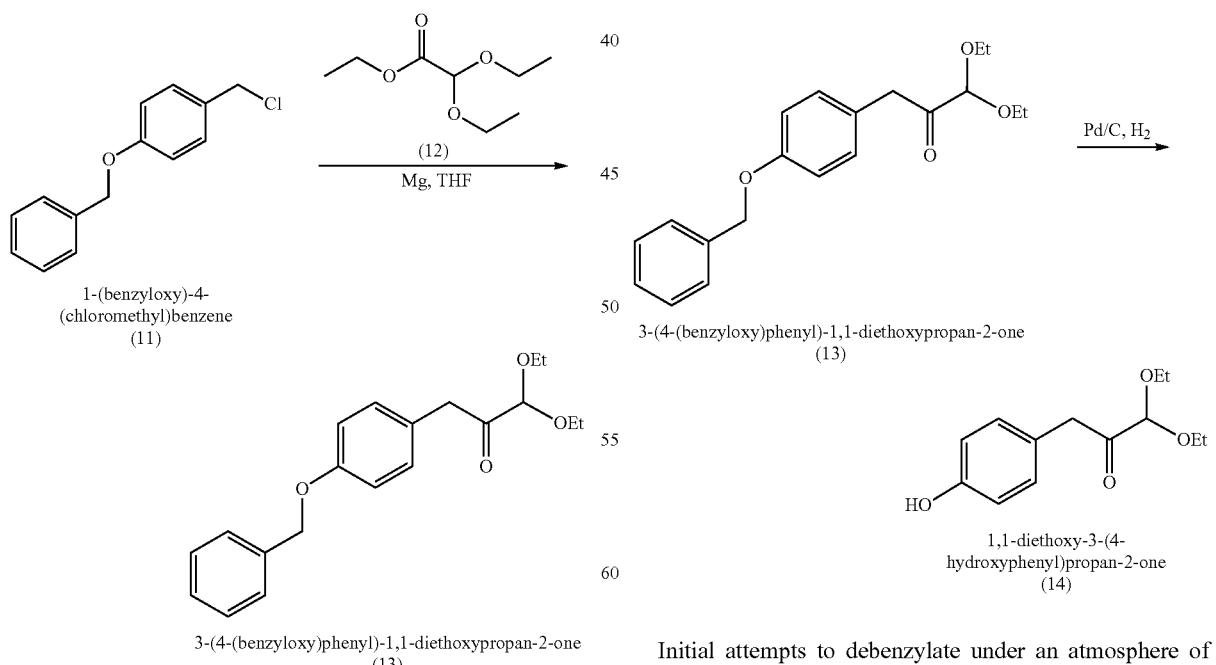

Mg turnings (10.57 g, 0.435 mole, 1.5 equiv) were suspended in dry distilled THF (100 mL) in an argon- Initial attempts to debenzylate under an atmosphere of hydrogen using palladium 10% on charcoal without the pressure reactor were not successful.

A solution of the compound (13) (66 g, 20.4 mole) in ethanol (400 mL) was placed in a Parr hydrogenation flask and 10% Pd/C (7 g) was added. The mixture was hydrogenated for 24 hours under hydrogen atmosphere at 60 Psi. The black suspension was filtered and the solvent was removed using a rotary evaporator. The product was purified by passing through a small pad of silica gel to remove any suspended carbon particles eluting with 50% ethyl acetate/hexane. The desired product was isolated over a silica gel column eluting with 30% ethyl acetate/hexane to a colorless oil, 21.7 g.

$^1$H NMR (400 MHz, CDCl$_3$): δ=1.25 (t, J=7.0 Hz, 6H), 3.55 (m, 2H), 3.71 (m, 2H), 3.82 (s, 2H), 4.64 (s, 1H), 5.11 (br s, 1H), 6.77 (d, J=8.6 Hz, 2H), 7.07 (d, J=8.6 Hz, 2H).

Coelenterazine[8-Benzyl-6-(4-hydroxyphenyl)-2-[(4-hydroxyphenyl)methyl]imidazo[1,2-α]pyrazin-3(7H)-one (16)

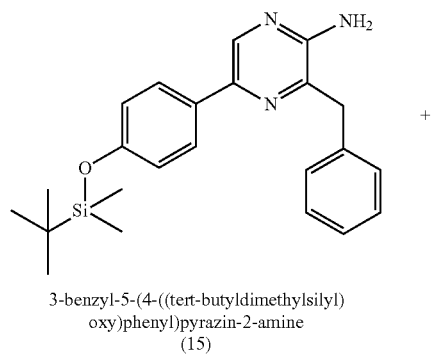

3-benzyl-5-(4-((tert-butyldimethylsilyl)oxy)phenyl)pyrazin-2-amine
(15)

+

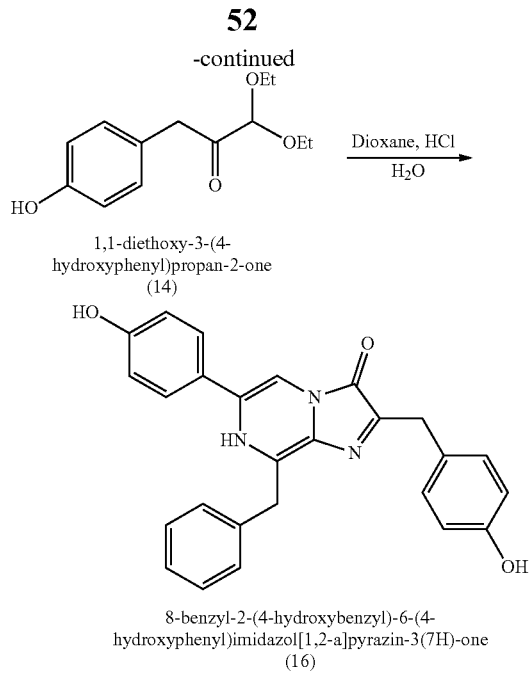

1,1-diethoxy-3-(4-hydroxyphenyl)propan-2-one
(14)

8-benzyl-2-(4-hydroxybenzyl)-6-(4-hydroxyphenyl)imidazol[1,2-a]pyrazin-3(7H)-one
(16)

The effect of dry hydrochloric acid, organic acids, vs. aqueous hydrochloric acid on the final condensation, rearrangement, and cyclization reaction of coelenterazine were evaluated. The following experiments were conducted either in ethanol or 1,4-dioxane. The results are summarized in the following Table 1.

TABLE 1

Coupling reaction conditions.

| (15) | (14) | Reaction conditions | Result* |
|---|---|---|---|
| 1 equivalent (eq) | 1 eq | Ethanol (EtOH)/dry HCl, 80° C., 8 h | — |
| 1 eq | 1 eq | EtOH/p-Toluenesulfonic acid (PTSA), 80° C., 8 h | — |
| 1 eq | 1 eq | EtOH/Trifluoroacetic acid (TFA), 80° C., 8 h | — |
| 1 eq | 1 eq | EtOH/Conc. HCl, 80° C., 8 h | ~50% conversion |
| 1 eq | 1 eq | Dioxane/Conc. HCl, 80° C., 8 h | Reaction is better than ethanol |

*The reaction mixture was analyzed by reverse phase HPLC. An authentic coelenterazine sample was used to identify the desired product.

The results from the above experiments (Table 1) indicated that the final condensation, rearrangement, and cyclization reaction of coelenterazine requires aqueous hydrochloric acid and the desired solvent is 1,4-dioxane, which proved to be better than ethanol.

After finding right solvent and acid, experiments were conducted with varying amounts of starting material (14). Starting material (15) was kept constant at 1 equivalent and the amount of starting material (14) was increased. Unreacted excess of the reagent (starting material 14) could be removed by washing with organic solvent. Furthermore, under acidic reaction conditions only pyrazinamine starting material (15) derived product will form salt but not the acetal (14). To obtain insight into the correct amount of reagents required for optimal reaction conditions, the following experiments were conducted. The results are summarized in the following Table 2.

TABLE 2

Coupling reaction starting material ratios.

| (15) | (14) | Reaction conditions | Result* |
|---|---|---|---|
| 1 eq | 1 eq | Dioxane (0.6 ml)/ 6N HCl (140 mg), water (0.1 ml), 80° C., overnight | Good reaction, some side product |
| 1 eq | 1.3 eq | Dioxane (0.6 ml)/ 6N HCl (140 mg), water (0.1 ml), 80° C., overnight | Better reaction, minimum side products |
| 1 eq | 1.7 eq | Dioxane (0.6 ml)/ 6N HCl (140 mg), water (0.1 ml), 80° C., overnight | Best reaction, minimum side products |

*The reaction mixture was analyzed by reverse phase HPLC. An authentic Coelenterazine sample was used to identify the desired product.

Coelenterazine, [8-benzyl-6-(4-hydroxyphenyl)-2-[(4-hydroxyphenyl) methyl]imidazo[1,2-α]pyrazin-3(7H)-one (16)

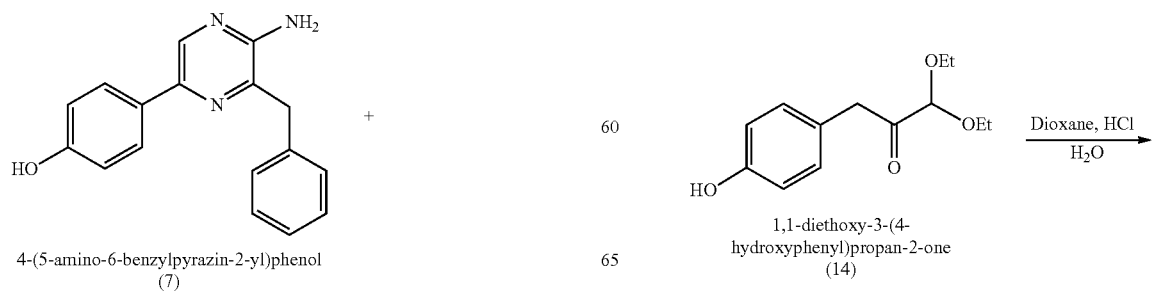

4-(5-amino-6-benzylpyrazin-2-yl)phenol (7)

1,1-diethoxy-3-(4-hydroxyphenyl)propan-2-one (14)

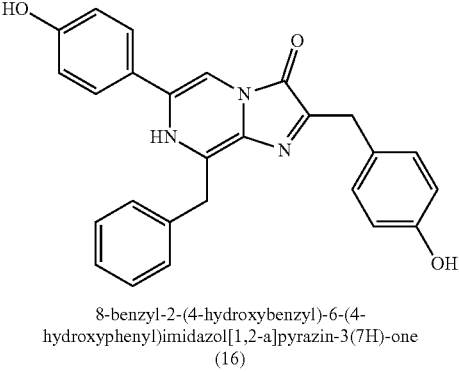

8-benzyl-2-(4-hydroxybenzyl)-6-(4-hydroxyphenyl)imidazol[1,2-a]pyrazin-3(7H)-one
(16)

1,4-dioxane (2.3 mL), water (225 μL), and conc. HCl (225 μL) taken in a 25 ml round bottomed flask was degassed and filled with argon. 4-(5-amino-6-benzyl-pyrazin-2-yl)phenol ((7), 441 mg, 1.59 mmol) was added to this mixture. A solution of 1,1-diethoxy-3-(4-hydroxyphenyl)-2-propan-2-one) ((14), 493 mg, 2.06 mmol, 1.3 eq) in 1,4-dioxane (2 mL) was added to this mixture. The resulting mixture was degassed and stirred under argon atmosphere at 78-82° C. for 14 hr. The dark brown solution was cooled to room temperature, and an aliquot was analyzed by reverse phase HPLC. The HPLC analysis indicated that the reaction mixture had little starting material. The reaction was degassed, and heating was continued for further 6 h (total 20 h). The reaction mixture was cooled to room temperature, and concentrated under reduced pressure. The dark brown residue was dried under high vacuum overnight. Ethyl acetate (40 mL) was added to the residue and triturated. The solid was allowed to settle decanted, and dried under vacuum to yield brown dry powder. Degassed ethyl acetate (40 mL) containing 1% methanol was added to the brown solid and triturated at 65° C. The solid was allowed to settle, and decanted, and dried at pump to yield brown dry powder, 720 mg, quantitative yield. The proton NMR data is identical with that of reported values. On reverse phase HPLC it co-eluted with an authentic sample. The solid was again suspended in 40 ml of degassed ethyl acetate containing 1% methanol and stirred for 15 min., and decanted.

The sample was dried at pump to yield brown solid.

TABLE 3

Mass spectra and LCMS analysis of 3 different samples.

| Sample | Coelenterazine | Coelenterazine amine | Unknown |
|---|---|---|---|
| 1 | 62% | 11% | 5.4% |
| 2 | 65% | 11% | 6.2% |
| 3 | 66% | 10% | 6.3% |

Coelenterazine, [8-Benzyl-6-(4-hydroxyphenyl)-2-[(4-hydroxyphenyl) methyl]imidazo[1,2-α]pyrazin-3(7H)-one (16): 25 g scale synthesis

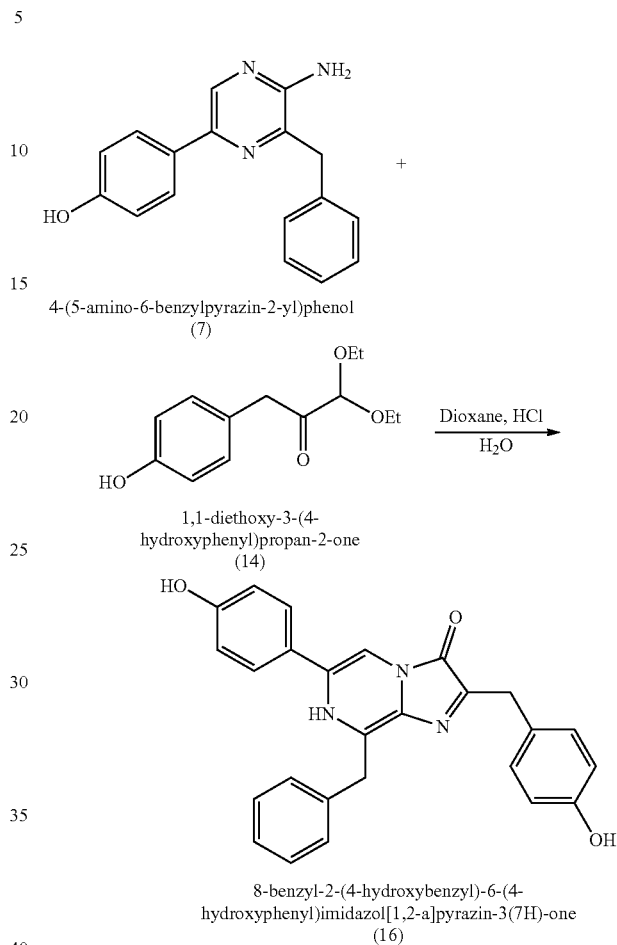

1,4-dioxane (80.0 mL), water (9.1 mL), and conc. HCl (9.1 mL) taken in 300 ml round bottomed flask was degassed and filled with argon. 4-(5-amino-6-benzyl-pyrazin-2-yl) phenol (7, 15.94 g, 59.93 mmol) was added to this mixture and stirred a degassed 1,4-dioxane (71 mL) solution of 1,1-diethoxy-3-(4-hydroxyphenyl)-2-propan-2-one) (14, 16.4 g, 68.82 mmol, 1.2 eq) was added to this suspension. The resulting mixture was degassed and stirred under argon atmosphere at 78-84° C. for 34 h (the reaction progress was monitored by reverse phase HPLC). The reaction was cooled to room temperature, and concentrated under reduced pressure. The dark brown residue was dried under high vacuum overnight. Degassed ethyl acetate (250 mL) was added to this brown residue and triturated. The solid was allowed to settle, and decanted. This process was repeated second time, and the solid was dried at pump for 24 h to yield a brown dry powder, 25.8 g, in quantitative yield.

Example 3. Synthesis of Coelenterazine HCl Salt, 100 g Scale

Starting material synthesis:

The starting material 4-(5-amino-6-benzyl-pyrazin-2-yl) phenol (7) (53.0 g), and 1,1-diethoxy-3-(4-hydroxyphenyl) propan-2-one (14) (57.0 g) were synthesized by following the procedure described previously in Example 2.

8-Benzyl-6-(4-hydroxyphenyl)-2-[(4-hydroxyphenyl)methyl]-7H-imidazo[1,2-α]pyrazin-3-one (3)

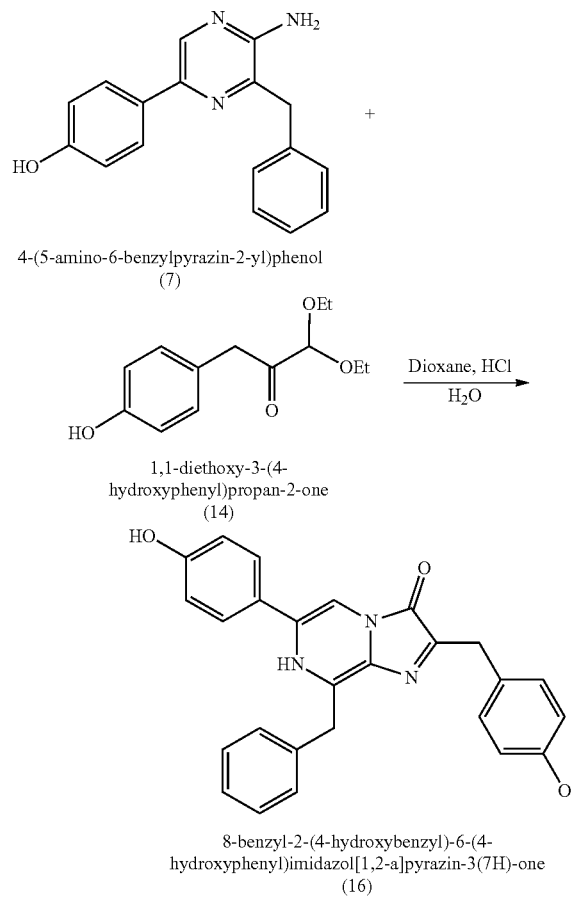

4-(5-amino-6-benzylpyrazin-2-yl)phenol
(7)

1,1-diethoxy-3-(4-hydroxyphenyl)propan-2-one
(14)

8-benzyl-2-(4-hydroxybenzyl)-6-(4-hydroxyphenyl)imidazol[1,2-a]pyrazin-3(7H)-one
(16)

A 1 L round bottom flask equipped with a stirrer bar was charged with 4-(5-amino-6-benzyl-pyrazin-2-yl)phenol (7) (53.0 g, 191.25 mmol), followed by 1,4-dioxane (275 mL). The resulting mixture was degassed and filled with argon. To this stirred mixture was added degassed 1:1 water/conc. HCl (62.0 mL). The resulting mixture was again degassed and filled with argon, and stirred at room temperature for 15 min. To this stirred suspension was added a degassed 1,4-dioxane (244 mL) solution of 1,1-diethoxy-3-(4-hydroxyphenyl)-2-propan-2-one (14) (57.0 g, 239.21 mmol, 1.25 eq). The resulting mixture was degassed and stirred under argon atmosphere at 80-85° C. for 38 h (the reaction progress was monitored by reverse phase HPLC).

The reaction was cooled to room temperature, and concentrated under reduced pressure. The resulting dark brown residue was dried under high vacuum overnight. To this was added degassed ethyl acetate (250 mL) and triturated. The solid was allowed to settle, and decanted. This process was repeated one more time. Then added a degassed ethyl acetate (200 mL) containing 1% methanol to the brown solid and triturated. The solid was allowed to settle, and decanted. The residual dark brown solid was dried at high vacuum at 40° C. for 36 h, and stored under argon atmosphere, yield 101.8 g. On reverse phase HPLC it co-eluted with an authentic sample. The proton NMR spectral data were consistent with the reported values.

Example 4. Synthesis of Coelenterazine (Multiple Kilograms)

Synthesis of 3-benzylpyrazin-2-amine (25)

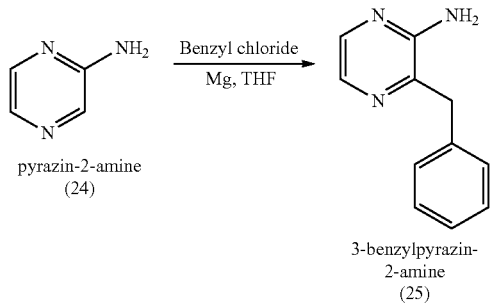 [SMILES: Nc1cnccn1 ; Nc1nccnc1Cc1ccccc1]

pyrazin-2-amine
(24)

3-benzylpyrazin-2-amine
(25)

A 100 L round bottom flask was charged with 7.5 L of THF, 2.5 kg of magnesium metal, 10 g of iodine, and 200 ml ethyl bromide. The reaction mass was initiated. After initiation, benzyl chloride in THF solution (10 L benzyl chloride dissolved in 45 L of THF) was slowly added at 20-25° C. over a period of 4 to 4.5 hours and thereafter maintained for one hour at 30-35° C. Then, 2-amino pyrazine solution (2.5 kg 2-amino pyrazine dissolved in 25 L THF at 30-35° C. in 1 to 1.5 hours) was slowly added and the reaction mass was maintained for 5-6 hours at 30-35° C. A TLC check was done, after compliance 10 L water was slowly added and the reaction mass was stirred for 20 minutes. The reaction mass was then allowed to settle for 30 minutes. The THF layer was separated and distilled out completely under vacuum below 70° C. After completing the distillation, the reaction mass was then cooled to room temperature and charged with 20 L toluene and 5 L water and stirred for 10 minutes. The reaction mass was then allowed to settle for 20 minutes and the toluene layer was separated. The toluene layer was then charged with 3 L HCl and allowed to settle for 10 minutes. Then the toluene layer was separated and kept aside. The acidic HCl layer was then adjusted to a pH of about 8-9 with 3 kg soda ash and maintained for 30 minutes. The organic layer was then separated to yield the desired mono alkylated product in 40%-45% yield, purity 94%-95%.

The present modification reduces or eliminates the use of: n-butyl lithium-in the first step of the synthesis of Example 1, where n-butyl lithium reaction in toluene has been replaced by reaction with benzyl chloride and THF (tetrahydrofuran). Thus, the present Example improves the ability to scale up the reaction chemistry and reduces the cost of the synthesis. In addition, the changes improve the overall safety of the chemistry by replacing highly reactive materials with more stable materials.

Synthesis of 3-benzyl-5-bromopyrazin-2-amine (2)

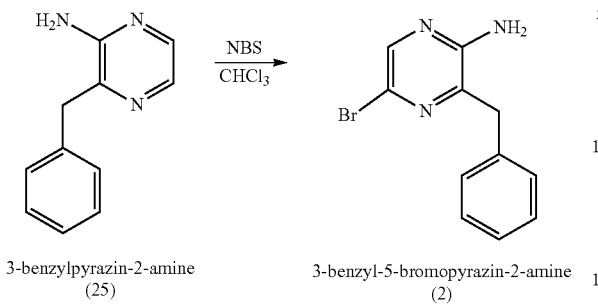
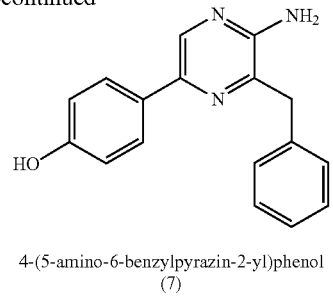

3-benzylpyrazin-2-amine (25)

3-benzyl-5-bromopyrazin-2-amine (2)

The synthesis of 3-benzyl-5-bromopyrazin-2-amine is as described above, in Example 1. Specifically, a 20 L round bottom flask was charged with chloroform (6 L) and 3-benzylpyrazin-2-amine (25) (also named 2-amino-3-benzyl pyrazine, (25)) (1 Kg), and the mixture was stirred at room temperature (22° C.). N-bromosuccinimide (NBS) (800 grams) was added slowly over 1 to 1.5 hrs. After the complete addition, the mixture was stirred for 30 minutes. Water (2 L) was added and stirred for 10 minutes. The organic layer was separated and washed with water (2×1 L). The chloroform layer was concentrated under reduced pressure and the oily residue was dried under vacuum. Yield 77%-85%. Purity 93%-95%.

Synthesis of 4-(5-amino-6-benzylpyrazin-2-yl)phenol (7)

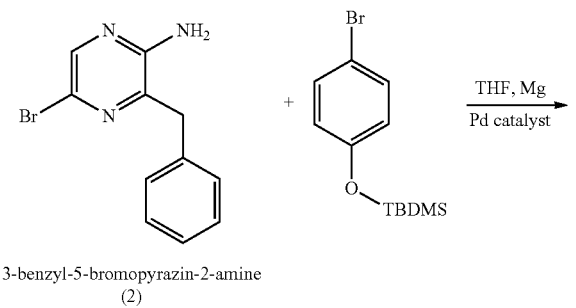

3-benzyl-5-bromopyrazin-2-amine (2)

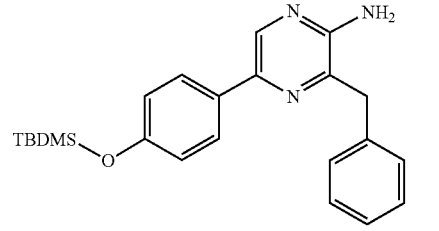

3-benzyl-5-(4((tert-butyldimethylsilyl)oxy)phenyl)pyrazin-2-amine (26)

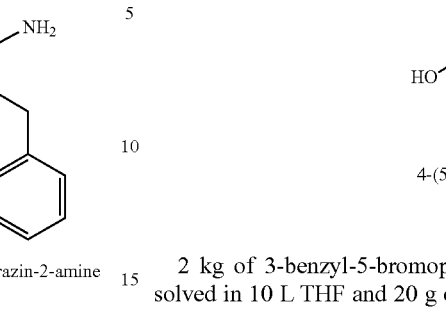

4-(5-amino-6-benzylpyrazin-2-yl)phenol (7)

2 kg of 3-benzyl-5-bromopyrazin-2-amine (2) was dissolved in 10 L THF and 20 g of palladium catalyst (significantly reduced from Example 1, 1/15 of the 300 g of palladium catalyst in Example 1) and stirred at room temperature for 30 minutes. This solution was added to the Grignard reagent prepared using para bromo-phenol 3 kg, 4 kg of TBDMS chloride (t-butyldimethylsilyl chloride), and 2.5 kg of Mg metal. The reaction mixture was heated to 50° C. for 24 hours. After the completion of the reaction providing (26), Mg metal was filtered and diluted HCl 3 L was added to reaction mixture and heated to 70° C. for 8 hours. To this reaction mixture containing (26) was added 2 L of water and the product was extracted with ethyl acetate 2 L, this was repeated three times. The combined ethyl acetate layers were washed with water 1.5 L, twice. The ethyl acetate is distilled to get the product (7) as a thick liquid with a weight of about 2.5 kg. Yield 70%-75% Purity 84%-88%.

Thus, the present example omits the use of boronic acid compounds in the synthesis, and greatly reduces the amount of expensive palladium catalyst in the reaction.

Synthesis of 4-((tert-butyl(4-(chloromethyl)phenoxy)dimethylsilane

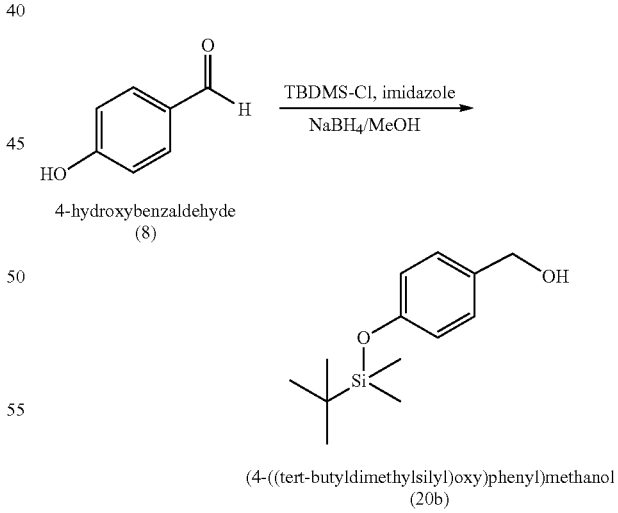

4-hydroxybenzaldehyde (8)

(4-((tert-butyldimethylsilyl)oxy)phenyl)methanol (20b)

A 20 L round bottom flask was charged with dichloromethane (10 L), 4-hydroxy benzaldehyde (8) (1 Kg). N,N'-dimethylaminopyridine (50 grams) and imidazole (1.33 Kg). The reaction mixture was cooled to 20° C. and stirred. To this stirred mixture was added portion-wise tert-butyldimethylsilyl chloride (TBDMS-Cl, 500 grams×3). After 1 hour, the reaction mixture was filtered, and concentrated under reduced pressure to get an oily product (4-((tert-butyldimethylsilyl)oxy)benzaldehyde, (20a)).

The above product (20a) was taken in a 10 L round bottom flask and dissolved in methanol (6 L). The reaction mixture was cooled to 10-15° C., and sodium borohydride (100 grams) was added with stirring. After 30 minutes the reaction pH was adjusted to 7.0 with acetic acid. After stirring for 20 minutes, methanol was distilled off to yield the desired product (20b). Yield 85%-90%, Purity 80%-85%.

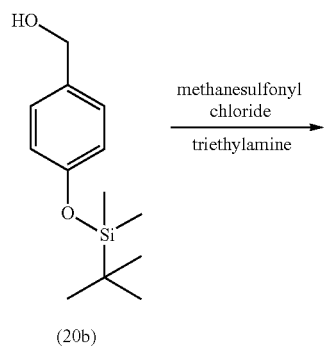

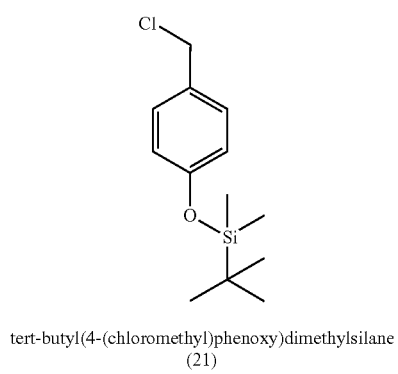

A 10 L round bottom flask was charged with 4-(tert-butyldimethylsiloxy)benzyl alcohol (20b) (1 Kg) and dichloromethane (6 L) followed by triethylamine (1.4 L). The reaction mixture was stirred for 30 minutes at room temperature. Methanesulfonyl chloride (600 mL) was added slowly at 30-35° C. in about 1-1.5 hours. After the completion of the reaction 30% aqueous sodium bicarbonate solution (400 ml) was added and stirred for 20 minutes. Dichloromethane layer was separated and washed with aqueous sodium chloride solution (2×500 ml). Dichloromethane was removed under reduced pressure. The residue containing tert-butyl(4-(chloromethyl)phenoxy)dimethylsilane (21) was used for the next step without further purification.

Synthesis of 3-(4-((tert-butyldimethylsilyl)oxy)phenyl)-1,1-dimethoxypropan-2-one) (27)

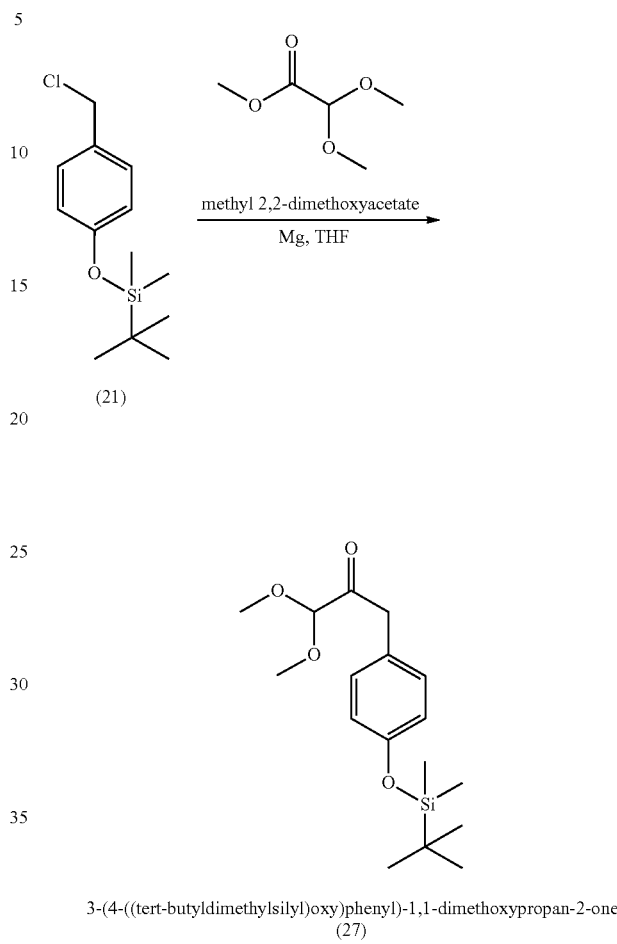

3-(4-((tert-butyldimethylsilyl)oxy)phenyl)-1,1-dimethoxypropan-2-one (27)

A 50 L round bottom flask was charged with magnesium turnings (1 Kg) and anhydrous tetrahydrofuran (3 L) followed by iodine (10 g) and dibromoethane (50 mL). A solution of tert-butyl(4-(chloromethyl)phenoxy)dimethylsilane (21) (1.6 kg) in anhydrous tetrahydrofuran (12 L) was added drop wise at 40-45° C. over a period of 4 hours. The reaction mixture was cooled to 35° C. Another 50 L round bottomed flask was charged with methyl 2,2-dimethoxyacetate (1.2 kg) and anhydrous tetrahydrofuran (10 L) and cooled to 30-35° C. The above-prepared Grignard reaction mixture was added to this solution at −10° C. over a period of 1-1.5 hours. After the completion of the reaction, the reaction mixture was quenched with saturated aqueous ammonium chloride solution (1.2 Kg in water 7 L). The organic layer was separated, washed with saturated sodium chloride solution and the solvent was removed under reduced pressure. The oily residue was purified by column chromatography over silica gel to yield 3-(4-((tert-butyldimethylsilypoxy)phenyl)-1,1-dimethoxypropan-2-one (27) (0.48 Kg) Yield 40%-45%. Purity 90%.

Synthesis of coelenterazine, 8-benzyl-2-(4-hydroxy-benzyl)-6-(4-hydroxyphenyl)imidazo[1,2-α]pyrazin-3 (7H)-one (16)

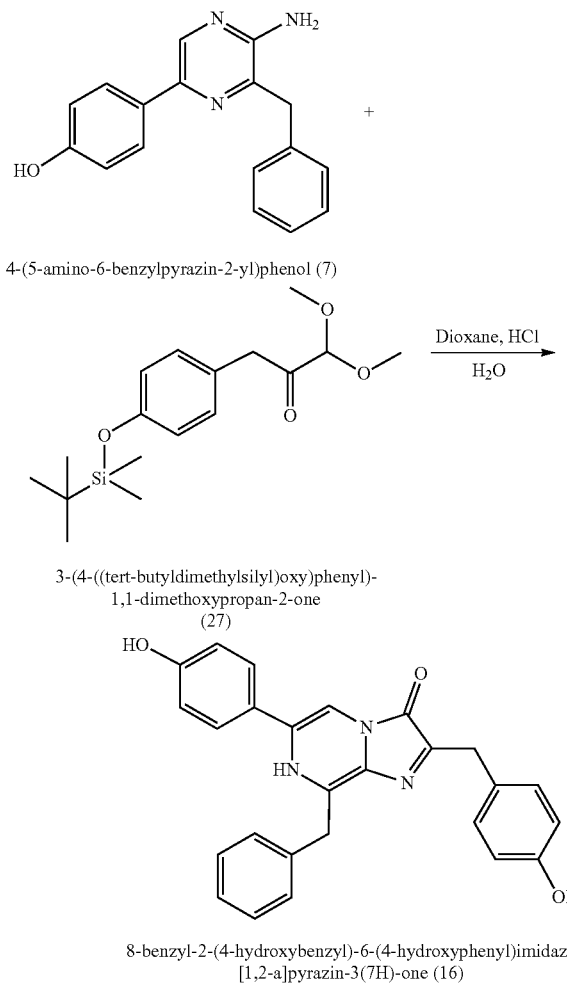

4-(5-amino-6-benzylpyrazin-2-yl)phenol (7)

3-(4-((tert-butyldimethylsilyl)oxy)phenyl)-1,1-dimethoxypropan-2-one (27)

8-benzyl-2-(4-hydroxybenzyl)-6-(4-hydroxyphenyl)imidazo[1,2-a]pyrazin-3(7H)-one (16)

A 30 L round bottom flask was charged with 4-(5-amino-6-benzyl-pyrazin-2-yl)phenol (7) (0.9 Kg) and 3-(4-((tert-butyldimethylsilyl)oxy)phenyl)-1,1-dimethoxypropan-2-one (27) (1.4 Kg) followed by 1,4-dioxane (14 L). The reaction mixture was stirred at room temperature for 30 minutes. Concentrated hydrochloric acid (0.75 L) and water (0.75 L) was added and the reaction mixture was heated to 80-85° C. for 15 hours. The reaction mixture was cooled to 40° C. then activated carbon (100 g) and activated silica gel (100 g) were added and filtered. The solvent was removed under reduced pressure and the residue (16) was precipitated by stirring with degassed ethyl acetate (2 L). Yield 60%-65%. Purity 60%-63%.

Example 5. LC-MS Characterization of Isolated Coelenterazine Compositions

The relative amount of coelenterazine to 4-(5-amino-6-benzylpyrazin-2-yl)phenol (7) (coelenteramine) in the final isolated composition from the final coupling reaction to form coelenterazine in Examples 1-3 can be assessed by liquid chromatography-mass spectrometry (LC-MS).

A 1 mg/ml methanolic solution of isolated coelenterazine compositions resulting from coupling reactions of 4-(5-amino-6-benzyl-pyrazin-2-yl)phenol (7) and 3-(4-((tert-butyldimethylsilyl)oxy)phenyl)-1,1-diethoxypropan-2-one (23), as described, for example in Example 1 above, was diluted ten times into an injection solvent consisting of 70:30 reagent water:acetonitrile (v/v), each supplemented with 0.05% formic acid. The diluted solution including the isolated coelenterazine composition was separated by LC on a C-18 reverse phase column using a gradient elution. The separation provided a response for coelenterazine at about 1.7 min and a response for coelenteramine (7) at about 2.5 min. Tandem MS was configured to monitor the (M+H)+ parent ion of each compound which was subsequently fragmented into its characteristic daughter ion. The daughter ion intensity created the chromatographic signal for each compound which was then integrated to produce an area for the signal. The parent ion for coelenterazine is 424.1 Da with a daughter ion at 302.2 Da. The parent ion for coelenteramine is 278.1 Da and its daughter was 132.0 Da. In Table 4 below, the ratio of the coelenterazine to coelenteramine in the isolated composition was between about 24:1 and 80:1.

TABLE 4

Integrated peak ratios of coelenterazine to coelenteramine as assessed by LC-MS.

| Composition | Coelenterazine integrated peak area | Coelenteramine integrated peak area | Coelenterazine/ coelentera-amine peak ratio |
| --- | --- | --- | --- |
| Isolated composition 1 | 3.63E+07 | 1.52E+06 | 24 |
| Isolated composition 2 | 3.15E+07 | 3.93E+05 | 80 |
| Isolated composition 3 | 2.72E+07 | 5.46E+05 | 50 |
| Isolated composition 4 | 2.87E+07 | 5.37E+05 | 53 |
| Isolated composition 5 | 2.91E+07 | 4.45E+05 | 65 |

Example 6. Synthesis of Coelenterazine using 4-(5-amino-6-benzylpyrazin-2-yl)phenol and 3-(4-(benzyloxy)phenyl)-2-oxopropanal 4-(5-Amino-6-benzyl-pyrazin-2-yl) phenol (coelenteramine)

3-Benzylpyrazin-2-amine

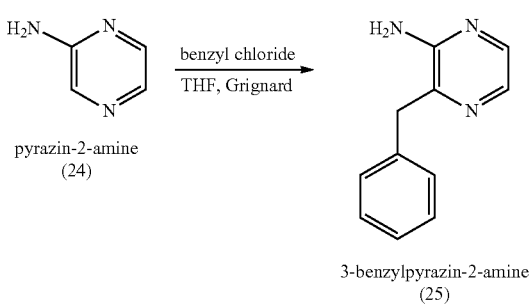 [SMILES: Nc1cnccn1 ; Nc1nccnc1Cc1ccccc1]

pyrazin-2-amine (24)

3-benzylpyrazin-2-amine (25)

A 100 L round bottom flask was charged with 7.5 L of tetrahydrofuran (THF), 2.5 kg magnesium metal, 10 g of iodine, and 200 ml ethyl bromide. The reaction mass was initiated, benzyl chloride and THF solution (10 L benzyl chloride dissolved in 45 L of THF) was slowly added at 10-20° C. over a period of 4 to 4.5 hours and thereafter maintained for 1 hour at 30-35° C. Then 2-amino pyrazine solution (2.5 kg 2-amino pyrazine dissolved in 25 L THF at 30-35° C. in 1 to 1.5 hrs) was slowly added and the reaction mass was maintained for 5-6 hours at 30-35° C. A thin layer chromatography (TLC) check was done, after compliance 10 L water was slowly added and the reaction mass was stirred for 20 minutes.

The reaction mass was then allowed to settle for 30 mins. The THF layer was separated and distilled out completely under vacuum below 70° C. After completing the distillation, the reaction mass was then cooled to room temperature and charged with 20 L toluene and 5 L water and stirred for 10 minutes. The reaction mass was then allowed to settle for 20 minutes and the toluene layer was separated. The toluene layer was then charged with 3 L HCl and allowed to settle for 10 minutes. Then the toluene layer was separated and kept aside. The acidic HCl layer was then adjusted to a pH of about 8-9 with 3 kg soda ash and maintained for 30 minutes. The organic layer was then separated to yield the desired mono alkylated product in 45-50% yield, at a purity 90-95%.

3-Benzyl-5-bromopyrazin-2-amine

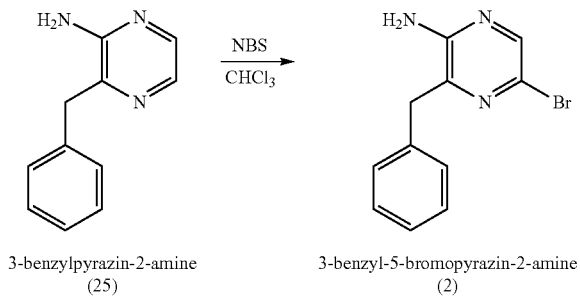

3-benzylpyrazin-2-amine (25)     3-benzyl-5-bromopyrazin-2-amine (2)

A 20 L round bottom flask was charged with chloroform (6 L) and 2-amino-3-benzyl pyrazine (1 Kg), and stirred the mixture at room temperature (22° C.). N-bromosuccinimide (800 grams) was added slowly over 1-1.5 h. After the complete addition, the mixture was stirred for 30 minutes. Water (2 L) was added and stirred for 10 minutes followed by the separation of the chloroform layer. HCl (500 ml) was added to the chloroform layer and the mixture was stirred for about 20 minutes. The product was filtered through Nutsche filter and was given a wash with chloroform (1 L). The product was dried at 35-40° C. for 6-7 hrs. Yield 70-75%. Purity 90-95%.

3-Benzyl-5-(4-methoxyphenyl)pyrazin-2-amine

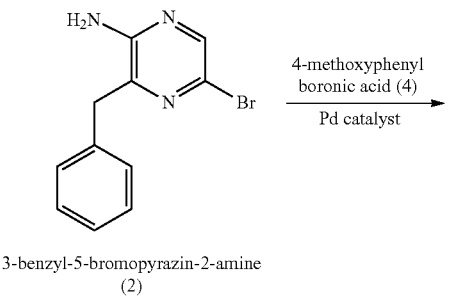

3-benzyl-5-bromopyrazin-2-amine (2)

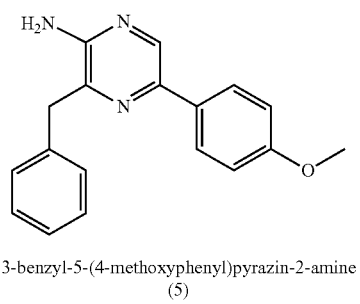

3-benzyl-5-(4-methoxyphenyl)pyrazin-2-amine (5)

A 50 L flask was charged with 1,4-dioxane (30 L) and 3-benzyl-5-bromopyrazin-2-amine (1 kg) at room temperature. Potassium carbonate (1.6 kg) was added followed by water (5 L). The reaction mixture was stirred for 10 minutes. 4-Methoxy phenyl boronic acid (600 grams) was added followed by palladium catalyst (40 grams). The reaction mixture was slowly heated up to 82° C. and stirred at 80-82° C. for 20-24 h under nitrogen. The mixture was cooled to 40° C. and transferred to 100 L round bottomed flask, and charged with ethyl acetate (15 L) and water (15 L) at room temperature and stirred for 20 minutes. The organic layer was separated and concentrated under reduced pressure to yield the desired product. Yield 85-90%. Purity 92-95%.

4-(5-Amino-6-benzyl-pyrazin-2-yl) phenol

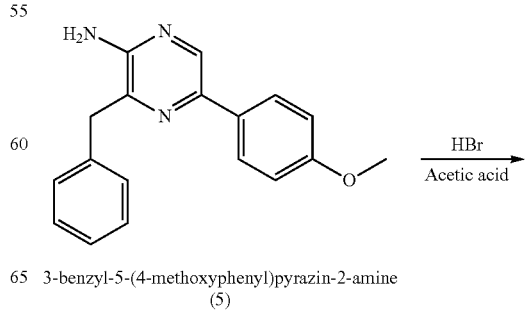

3-benzyl-5-(4-methoxyphenyl)pyrazin-2-amine (5)

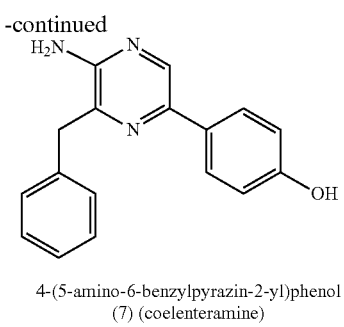

4-(5-amino-6-benzylpyrazin-2-yl)phenol
(7) (coelenteramine)

A 30 L round bottom flask was charged with 3-benzyl-5-(4-methoxyphenyl) pyrazin-2-amine (1 Kg), 4 L of 48% HBr and 7 L acetic acid. The reaction mixture was slowly heated to 110° C. in an oil bath. The reaction temperature was maintained at 108-110° C. for 8-10 hours. The mixture was cooled to 40° C. and charged with water (15 L) and ethyl acetate (15 L) at 35-40° C. The reaction mixture was stirred for 20 minutes. The pH of the mixture was adjusted to 4-4.5 using soda-ash and the mixture was stirred for 10 minutes.

The ethyl acetate layer was separated, and the aqueous layer was re-extracted with ethyl acetate (3 L×2). The combined ethyl acetate extracts were adjusted to pH 7-7.5 with soda-ash and was concentrated under reduced pressure. The residue was first cooled to 40° C. and was then taken up with 4 L of cyclohexane and refluxed. The compound was filtered through Nutsche filter and dried at 40-45° C. for 5-6 hrs. Yield: 75-80% Purity: 90%.

3-(4-(benzyloxy)phenyl)-2-oxopropanal 4-(benzyloxy)benzaldehyde

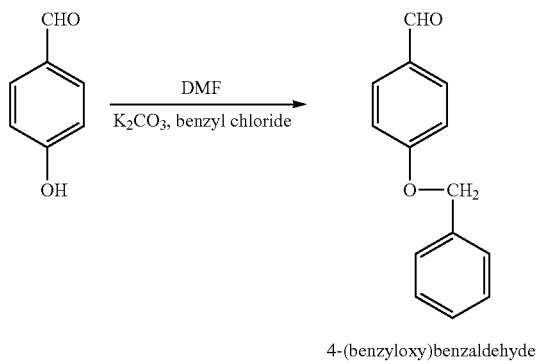

4-(benzyloxy)benzaldehyde

A 50 L round bottom flask was charged with dimethylformamide (15 L), 4-hydroxybenzaldehyde (2.5 Kg) and the mixture was stirred for 20 minutes. To this mixture, potassium carbonate (4 Kg) was added and the reaction mass was stirred for 10 minutes after which benzyl chloride (2.5 L) was added slowly for approximately 15 minutes. The mixture was stirred for 20 minutes and was slowly heated to 40° C. followed by stirring at 45-45° C. for 6-7 hrs. The mixture was cooled to 30° C. and charged with water (25 L). The mixture was cooled further to 20° C. and stirred for 30 minutes. The product obtained was centrifuged and washed with water until the product became pH neutral. The product was then dried at 30-35° C. for 5-6 hrs. Yield: 70-75% Purity: 85-90%.

(4-(benzyloxy)phenyl)methanol

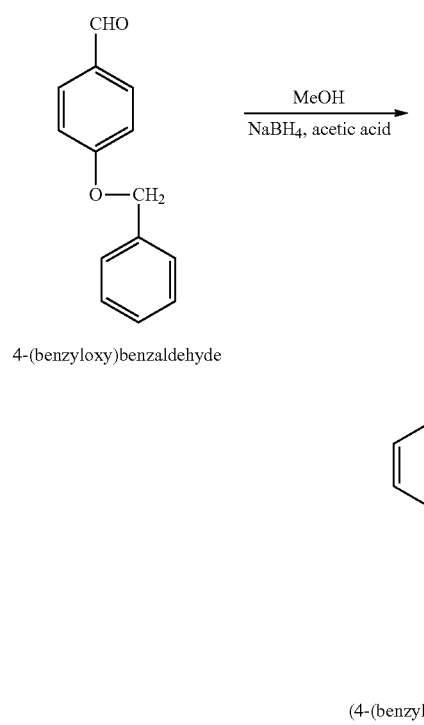

(4-(benzyloxy)phenyl)methanol

A 50 L round bottom flask was charged with 4-(benzyloxy)benzaldehyde (4 Kg) and methanol (15 L). To this mixture, sodium borohydride (0.5 Kg) was added drop-wise at 45-50° C. over 1-1½ hrs. After the addition was completed, the mixture was stirred for 30 minutes. The reaction mixture was cooled to 15° C. and was charged slowly with aqueous acetic acid (500 mL acetic acid in 500 mL water) followed by slow addition of water (25 L). This mixture was then stirred for 30 minutes at 15-20° C. The product was centrifuged and dried at 40-45° C. over 12-14 hrs. The resultant product was charged with n-hexane (10 L) and the reaction mixture was heated slowly to 50° C. The mixture was stirred at 50° C. for 1 hr after which it was cooled to 40° C. The product, (4-benzyloxy)phenyl)methanol was filtered through a Nutsche filter and it was then dried at 40-45° C. over 12 hrs. Yield: 85-90% Purity: 90-95%.

1-(benzyloxy)-4-(chloromethyl)benzene

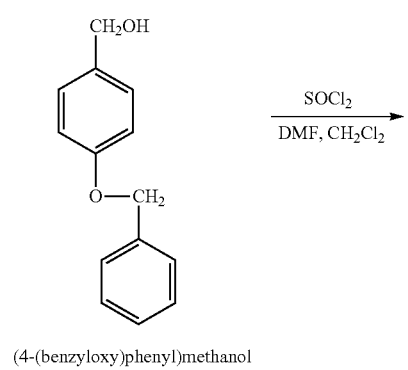

(4-(benzyloxy)phenyl)methanol

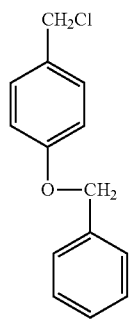

1-(benzyloxy)-4-(chloromethyl)benzene

A 50 L round bottom flask was charged with dichloromethane (20 L) and (4-(benzyloxy)phenyl)methanol (3.8 Kg) at room temperature. The mixture was stirred for 20 minutes and was charged with dimethylformamide (500 mL) followed by stirring for another 10 minutes. To this mixture, thionyl chloride (2 L) was added slowly at 30-35° C. over 1-1½ hrs. The mixture was stirred at room temperature for 1-1½ hrs. 50% of the dichloromethane was distilled normally and the remaining 50% was removed by distillation under reduced pressure. The residue was charged with water (5 L) and ethyl acetate (20 L) and this mixture was stirred for 10 minutes.

The ethyl acetate layer was separated and this layer was washed with a soda-ash solution (1 Kg soda-ash in 4 L water) to adjust the pH of the layer to 8-9. The mixture was stirred for 10 minutes. The ethyl acetate layer was separated again and was washed with a solution of common salt. (1 Kg NaCl in 3 L water). The mixture was stirred for 10 minutes. The ethyl acetate layer was separated once again and was concentrated under reduced pressure. The residue was taken up with n-hexane (10 L) and was refluxed. The product was then cooled to 10° C. and was stirred for 30 minutes. The product obtained was filtered through a Nutsche filter and was washed with n-hexane (1 L). The product, 1-(benzyloxy)-4-(chloromethyl)benzene, was dried at 40-42° C. over 5-6 hrs. Yield: 75-80% Purity: 90%.

3-(4-(benzyloxy)phenyl)-2-oxopropanal

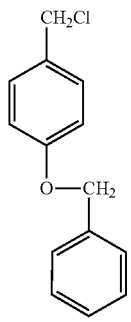

C₂H₂Br
THF, Mg, I₂
methyl 2,2-dimethoxyacetate
→

1-(benzyloxy)-4-(chloromethyl)benzene

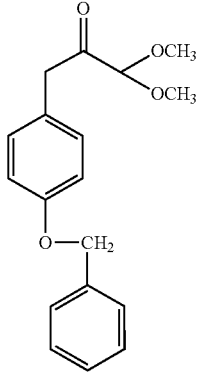

3-(4-(benzyloxy)phenyl)-1,1-dimethoxypropan-2-one

10% HCl →

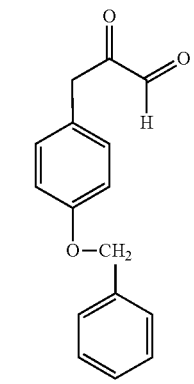

3-(4-(benzyloxy)phenyl)-2-oxopropanal

A 50 L round bottom flask was charged with anhydrous tetrahydrofuran (7.5 L) and magnesium turnings (2.5 Kg) followed by iodine (2 grams) and ethyl bromide (10 mL). To this mixture, a solution of 1-(benzyloxy)-4-(chloromethyl)benzene (3.2 Kg) in anhydrous tetrahydrofuran (40 L) was added drop wise at 40-45° C. The mixture was stirred for 1 h after which it was cooled to 20° C. To this cooled mixture, a solution of methyl 2,2-dimethoxyacetate (2.5 Kg) in anhydrous tetrahydrofuran (2.5 L) was added at 20-38° C. The mixture was stirred for 30 minutes at 40-42° C. To the Grignard reaction mass, ammonium chloride solution (2.5 Kg ammonium chloride in 10 L water) was added and this mixture was stirred for 20 minutes. The tetrahydrofuran layer was separated and was concentrated under reduced pressure. The product obtained was purified by column chromatography over silica gel. The purified product is heated to 60° C. along with 10 L of 10% HCl for 3 hours to obtain 3-(4-(benzyloxy)phenyl)-2-oxopropanal. Yield: 65-70% Purity: 90%.

8-Benzyl-2-(4-hydroxybenzyl)-6-(4-hydroxyphenyl) imidazo[1,2-α] pyrazin-3(7H)-one (coelenterazine)

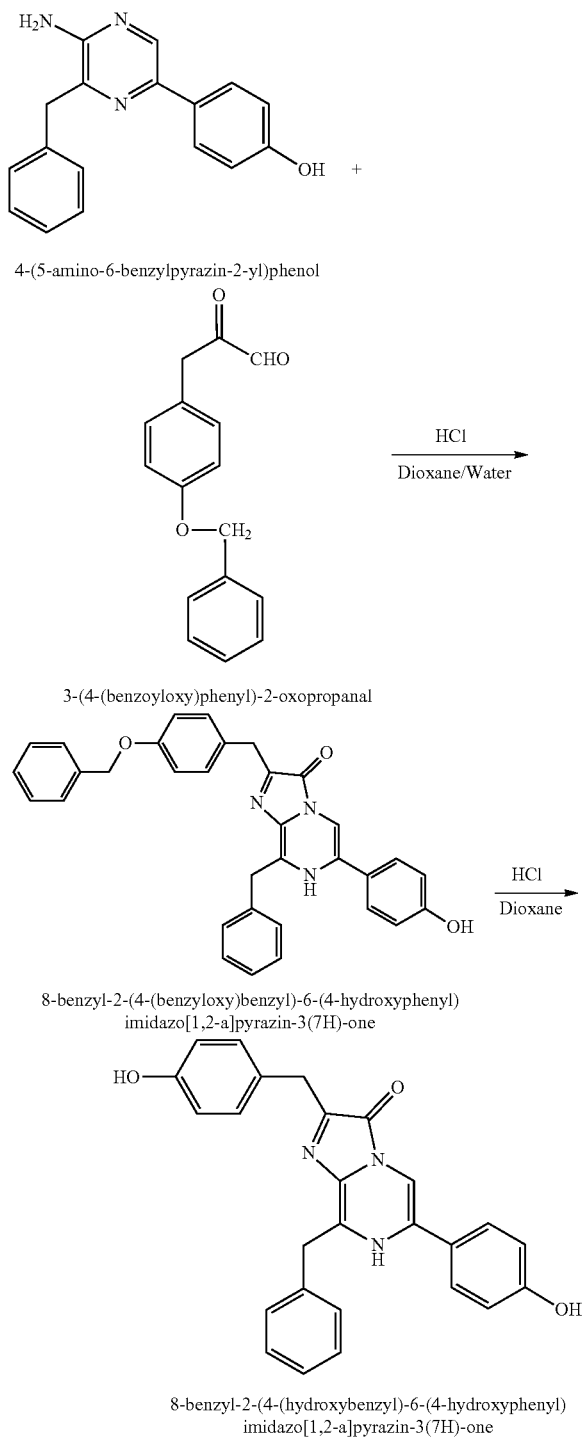

A 50 L round bottom flask was charged with 4-(5-amino-6-benzylpyrazin-2-yl)phenol (0.8 Kg) and 3-(4-(benzyloxy)phenyl)-2-oxopropanal (1.4 Kg) followed by 1,4-dioxane (10 L). The reaction mixture was stirred at room temperature for 30 minutes. Concentrated hydrochloric acid (1 L) and water (1 L) was added while nitrogen gas was being passed and the reaction mixture was heated to 80-85° C. for 24 hours in a nitrogen environment. After the completion of the reaction, the reaction mixture is cooled to 40° C. then activated carbon (200 g) and activated silica gel (100 g) are added and filtered.

Meanwhile, another 50 L round bottom flask was charged with HCl (15 L). Add slowly the above reaction mixture in to the HCl at 30-35° C. over 1-1½ hrs. The mixture was stirred for 30 minutes at 30-35° C. The product obtained was filtered through a Nutsche filter and was washed with toluene (1.5 L). The product was dried at 40-45° C. in 8-10 hrs.

The above product (1.5 Kg) was charged with dioxane-HCl (15 L) at room temperature. This mixture was stirred for 20 minutes and was then slowly heated to 60° C. The reaction mixture was stirred at 60-62° C. for 12 hrs and it was then stirred for 3 hrs at 70-72° C. The dioxane-HCl was removed completely under reduced pressure and the residue was cooled to 40° C. The residue was then charged with ethyl acetate (5 L) and the mixture was stirred for 15 minutes. The ethyl acetate layer was decanted. The residue was charged with dichloromethane (5 L) and this mixture was stirred for 35-40 minutes. Filter the compound through a Nutsche filter. To the filtrate dichloromethane (2.5 L) was added and this mixture was stirred for 25-30 minutes. The compound was filtered once again and the filtrate material was charged with n-hexane (4 L). The mixture was stirred for 20-25 minutes. The compound, 8-benzyl-2-(4-hydroxybenzyl)-6-(4-hydroxyphenyl)imidazo[1,2-α]pyrazin-3(7H)-one, was filtered once again and was washed with n-hexane (1 L). The product, 8-benzyl-2-(4-hydroxybenzyl)-6-(4-hydroxyphenypimidazo[1,2-α]pyrazin-3(7H)-one, was dried under reduced pressure at 40-45° C. over 7-8 hours. Yield: 80% Purity: 60-65%.

While illustrative embodiments have been illustrated and described, it will be appreciated that various changes can be made therein without departing from the spirit and scope of the disclosure.

The embodiments of the disclosure in which an exclusive property or privilege is claimed are defined as follows:

1. A method of making 3-(4-(benzyloxy)phenyl)-2-oxopropanal, comprising
   providing 1-(benzyloxy)-4-(chloromethyl)benzene, and
   reacting the 1-(benzyloxy)-4-(chloromethyl)benzene in two steps to provide 3-(4-(benzyloxy)phenyl)-2-oxopropanal,
   wherein a first step of the two steps comprises reacting the 1-(benzyloxy)-4-(chloromethyl)benzene with methyl 2,2-dimethoxyacetate under Grignard conditions to provide 3-(4-(benzyloxy)phenyl)-1,1-dimethoxypropan-2-one; and
   wherein a second step of the two steps comprises reacting the 3-(4-(benzyloxy)phenyl)-1,1-dimethoxypropan-2-one with aqueous acid to provide the 3-(4-(benzyloxy)phenyl)-2-oxopropanal.

2. The method of claim 1, wherein the method does not include more than one palladium-catalyzed reaction.

3. The method of claim 1, wherein reacting the 1-(benzyloxy)-4-(chloromethyl)benzene with methyl 2,2-dimethoxyacetate under Grignard conditions comprises reacting the 1-(benzyloxy)-4-(chloromethyl)benzene with methyl 2,2-dimethoxyacetate, ethyl bromide, magnesium, and a catalytic amount of iodine.

4. The method of claim 3, wherein the 3-(4-(benzyloxy)phenyl)-1,1-dimethoxypropan-2-one is purified by silica column chromatography.

5. The method of claim 1, wherein the aqueous acid is aqueous HCl.

6. The method of claim 1, wherein the 3-(4-(benzyloxy)phenyl)-2-oxopropanal is isolated in a yield of 60 to 75% at a purity of 85 to 95% relative to 1-(benzyloxy)-4-(chloromethyl)benzene.

* * * * *